United States Patent
Kung et al.

(10) Patent No.: US 10,329,626 B2
(45) Date of Patent: *Jun. 25, 2019

(54) NOL3 IS A PREDICTOR OF PATIENT OUTCOME

(71) Applicant: DANA-FARBER CANCER INSTITUTE, INC., Boston, MA (US)

(72) Inventors: Andrew Kung, Walpole, MA (US); David Ziegler, Dover Heights (AU)

(73) Assignee: Dana-Farber Cancer Institute, Inc., Boston, MA (US)

( * ) Notice: Subject to any disclaimer, the term of this patent is extended or adjusted under 35 U.S.C. 154(b) by 134 days.

This patent is subject to a terminal disclaimer.

(21) Appl. No.: 15/373,063

(22) Filed: Dec. 8, 2016

(65) Prior Publication Data

US 2017/0101688 A1 Apr. 13, 2017

Related U.S. Application Data

(63) Continuation of application No. 14/464,394, filed on Aug. 20, 2014, now Pat. No. 9,533,980, which is a continuation of application No. 12/685,411, filed on Jan. 11, 2010, now Pat. No. 8,841,067.

(60) Provisional application No. 61/143,517, filed on Jan. 9, 2009.

(51) Int. Cl.

| | | |
|---|---|---|
| *A61K 45/06* | (2006.01) | |
| *G01N 33/50* | (2006.01) | |
| *A61K 31/437* | (2006.01) | |
| *A61K 31/496* | (2006.01) | |
| *A61K 31/506* | (2006.01) | |
| *C07D 417/02* | (2006.01) | |
| *C12Q 1/6886* | (2018.01) | |
| *G01N 33/574* | (2006.01) | |

(52) U.S. Cl.
CPC .......... *C12Q 1/6886* (2013.01); *A61K 31/437* (2013.01); *A61K 31/496* (2013.01); *A61K 31/506* (2013.01); *A61K 45/06* (2013.01); *C07D 417/02* (2013.01); *G01N 33/5044* (2013.01); *G01N 33/57407* (2013.01); *G01N 33/57484* (2013.01); *C12Q 2600/106* (2013.01); *C12Q 2600/112* (2013.01); *C12Q 2600/118* (2013.01); *C12Q 2600/136* (2013.01); *C12Q 2600/158* (2013.01); *G01N 2800/52* (2013.01); *G01N 2800/7028* (2013.01)

(58) Field of Classification Search
None
See application file for complete search history.

(56) References Cited

U.S. PATENT DOCUMENTS

| | | | |
|---|---|---|---|
| 8,841,067 B2 * | 9/2014 | Kung | A61K 31/496 435/4 |
| 2004/0180002 A1 | 9/2004 | Young et al. | |
| 2010/0179163 A1 | 7/2010 | Kung et al. | |

FOREIGN PATENT DOCUMENTS

| | | |
|---|---|---|
| WO | WO 2005/097791 | 10/2005 |
| WO | WO 2007/013575 A2 | 2/2007 |
| WO | WO 2008/016893 | 2/2008 |
| WO | WO 2008/109057 | 9/2008 |

OTHER PUBLICATIONS

Adlard et al., The Lancet Oncology, 2002, 3, pp. 75-82.
Alikhani et al, J. Biol. Chem. (2005) 280, pp. 12096-12102.
Berge, S. M., et al. (1977) J. Pharm. Sci. 66 pp. 1-19.
Bilim et al., British J. Cancer, 2008, 98, pp. 941-949.
Bruns et al. Cancer Res. (2000) 60, pp. 2926-2935.
DeAngelis, N. Engl. J. Med., 344, pp. 114-123, 2001.
Fleming et al., Cancer Res., 52, pp. 4550-4553, 1992.
Garcia-Echeverria et al., Cancer Cell, Mar. 2004;5(3) pp. 231-239.
Guha et al., Int. J. Cancer 60, pp. 168-173, 1995.
Gura, Science, 1997, 278, pp. 1041-1042.
Hermanson et al., Cancer Res. 52, pp. 3213-3219, 1992.
Hoekstra et al., Clinical Cancer Research vol. 11, pp. 6908-6915, Oct. 1, 2005.
Hong et al., FEBS Lett. (2003) 543, pp. 170-173.
Ishii et al., Brain Pathol. (1999) 9, pp. 469-479.
Kaiser, Science, 2006, 313, p. 1370.
Kilic et al., Cancer Res. 60, pp. 5143-5150, 2000.
Koseki et al., Proc. Nat. Acad. Sci. (1998) 95, pp. 5156-5160.
Motzer et al., JAMA, 2006, 295, pp. 2516-2524.
Phillips et al., Cancer Cell (2006) 9, pp. 157-173.
Pritzker, Clinical Chemistry, 2002, 48, pp. 1147-1150.
Sun et al., Cancer Cell (2006) 9, pp. 287-300.
Tannock, I.F.; Hill R.P., "Experimental Chemotherapy, Ch. 19", The Basic Science of Oncology, New York, NY, 1992, pp. 338, 352-359.
Weisberg et al., Cancer Cell. Feb. 2005;7(2): pp. 129-141.
Weisberg et al., Mol. Cancer. Therapeutics, 2007, 6, pp. 1951-1961.
Ziegler et al., J. Clin. Invest., 2008, 118, pp. 3109-3122.

* cited by examiner

*Primary Examiner* — Peter J Reddig
(74) *Attorney, Agent, or Firm* — Brinks Gilson & Lione

(57) ABSTRACT

The present invention features a method for determining the prognosis for survival of a cancer patient. Methods for measuring the level of NOL3 expression in a cancer cell-containing sample from a patient, and comparing the level of NOL3 expression in the sample to a reference level of NOL3 expression are also included. A higher level of NOL3 relative to the reference level correlates with decreased survival of the patient, and an equivalent or lower level of NOL3 relative to the reference level correlates with increased survival of the patient.

17 Claims, 41 Drawing Sheets

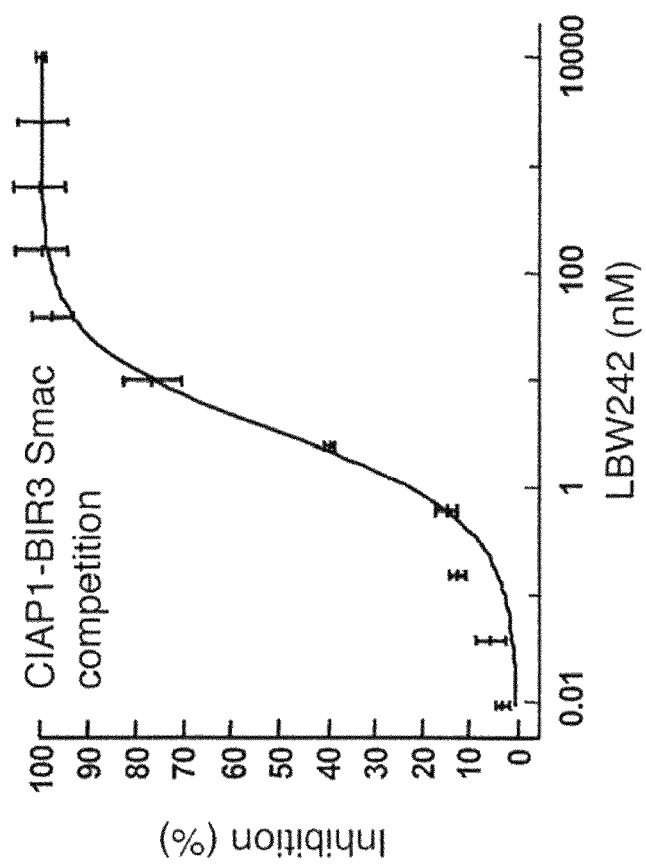

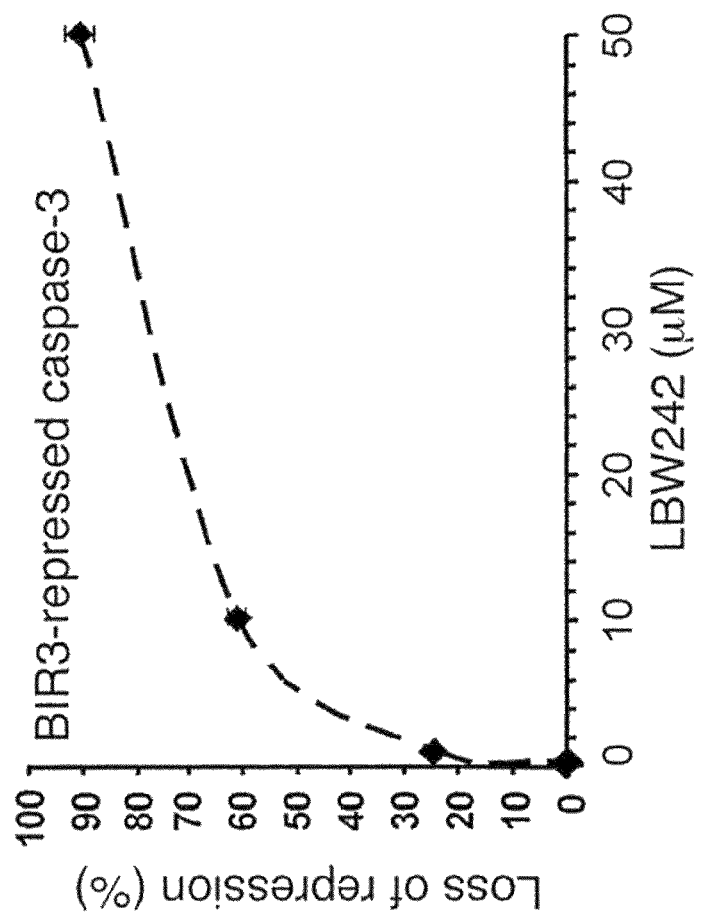

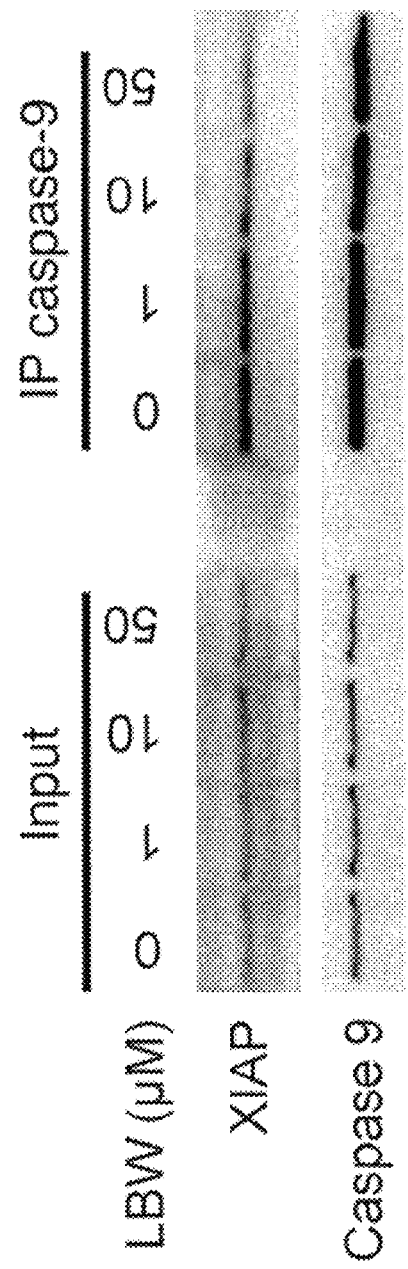

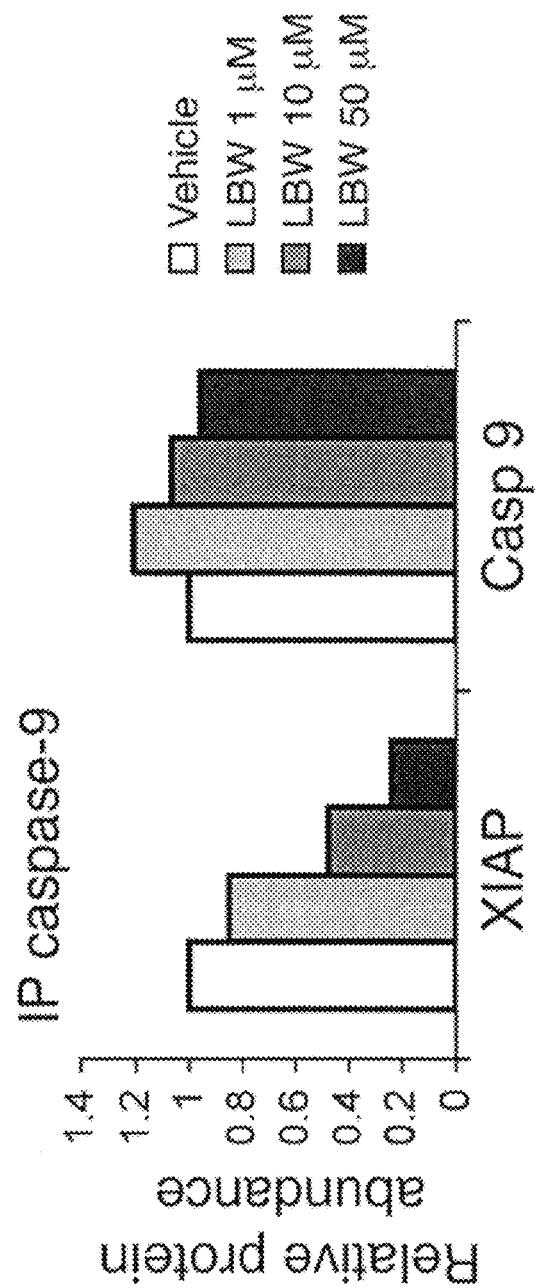

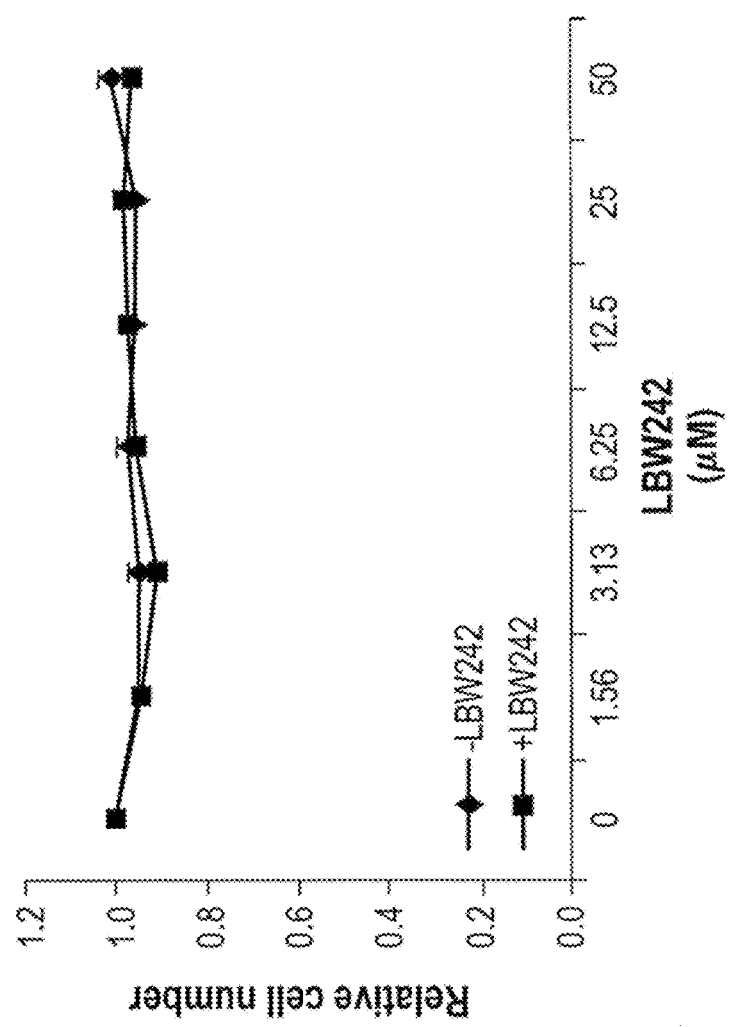

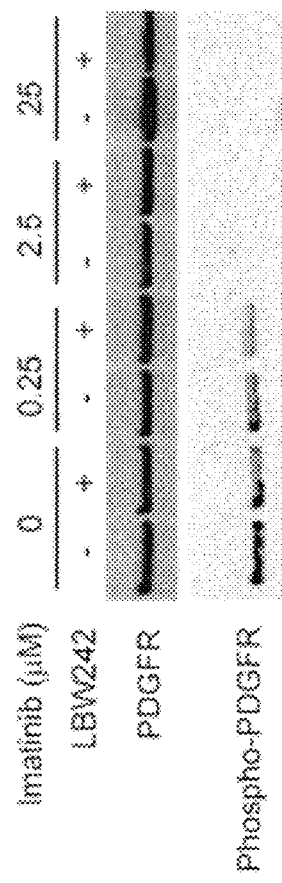

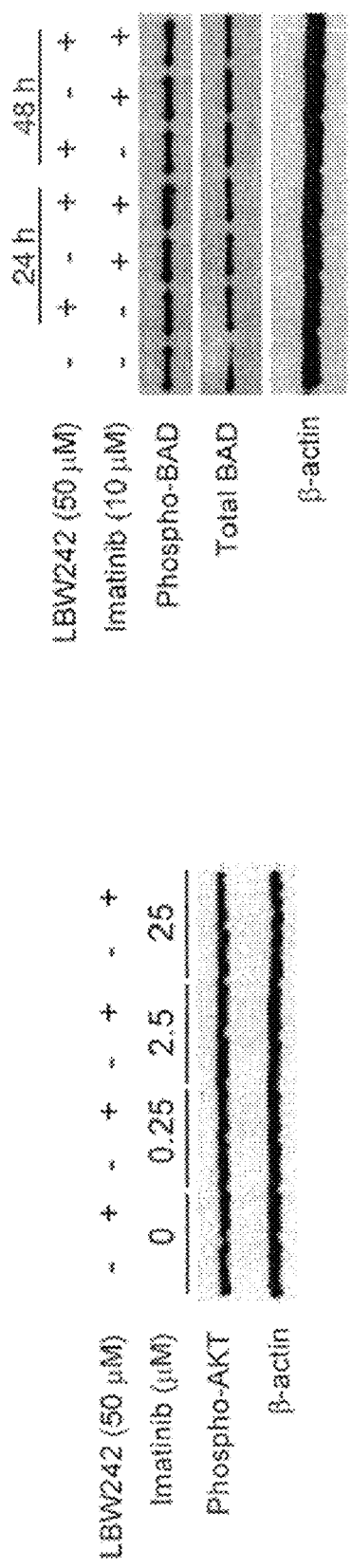

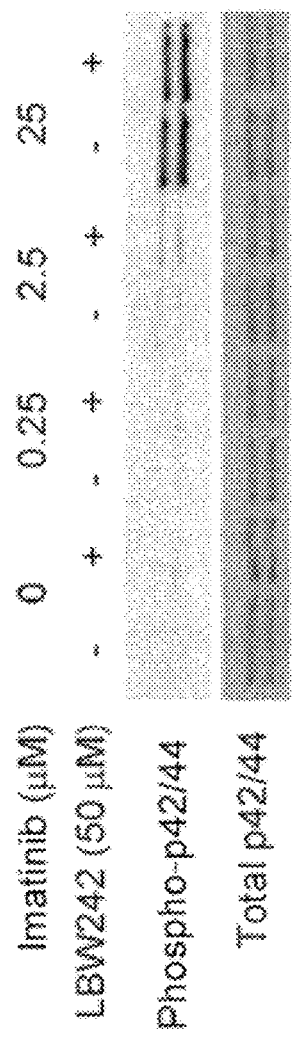

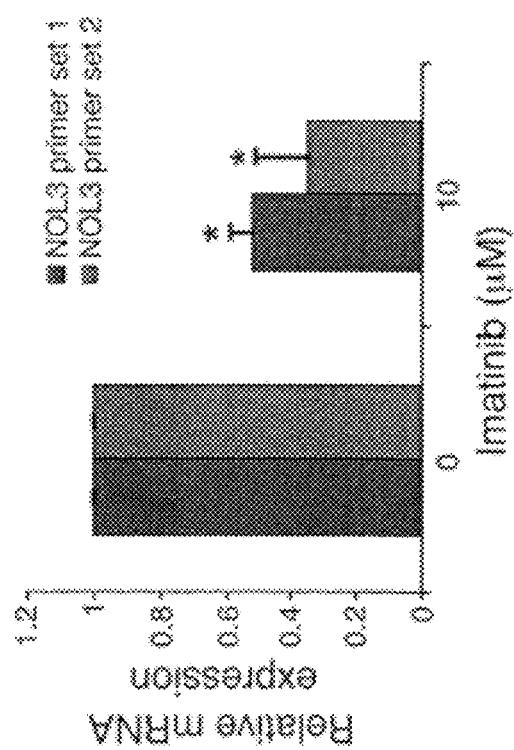

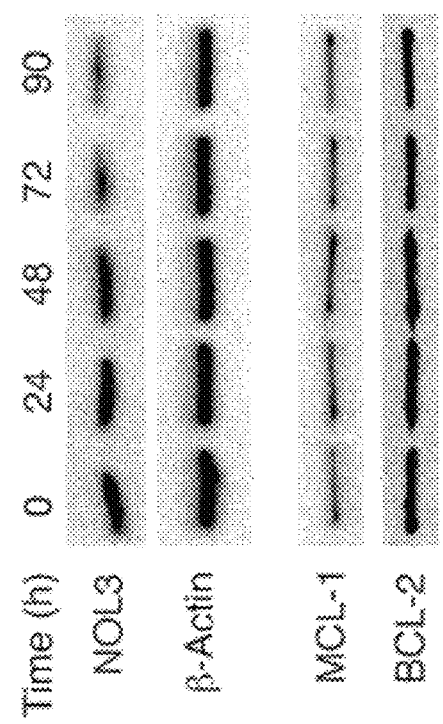

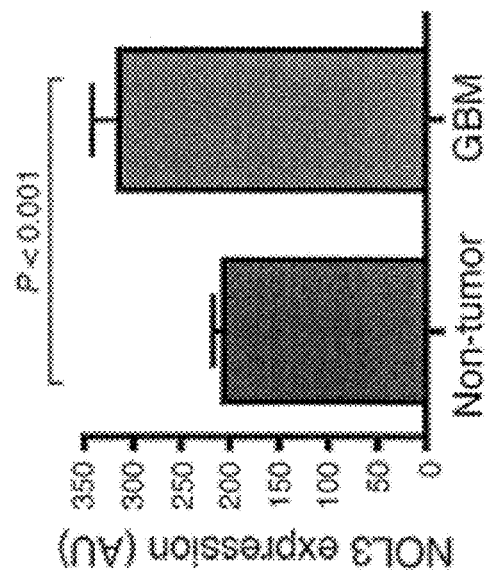

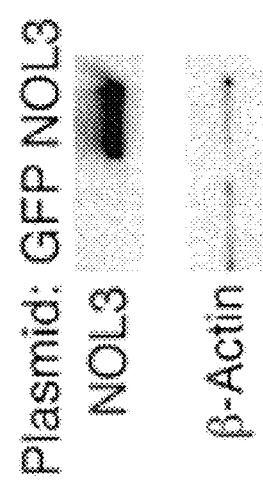

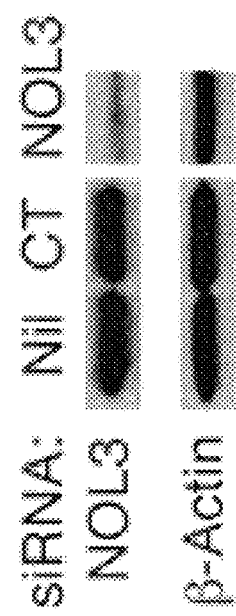

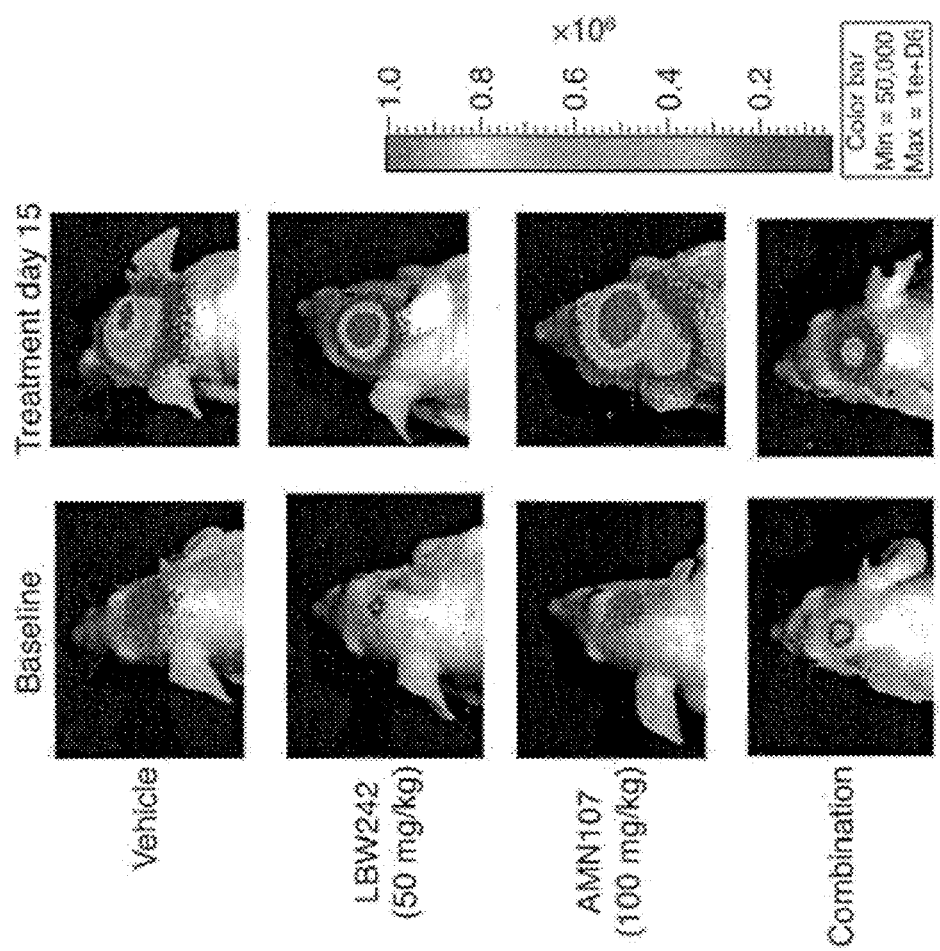

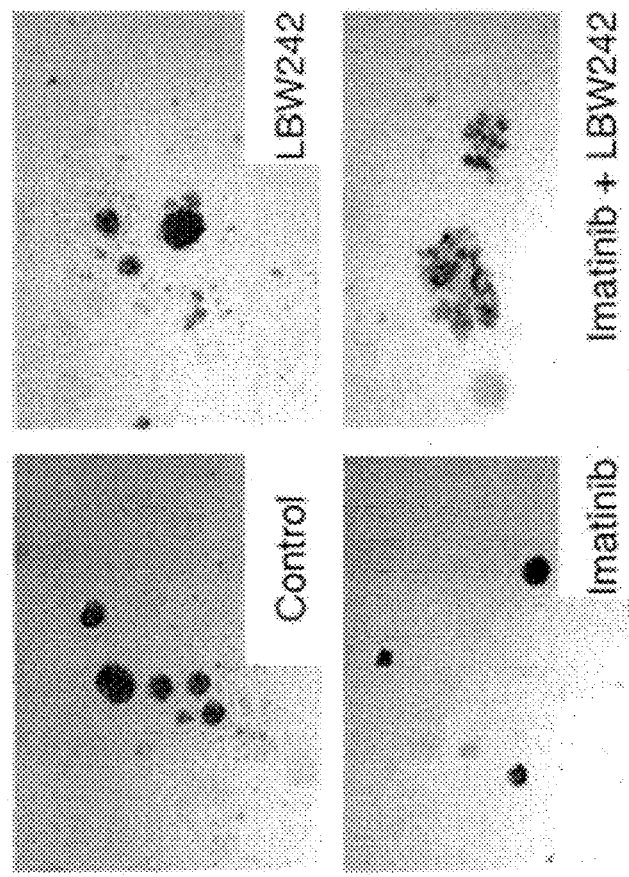

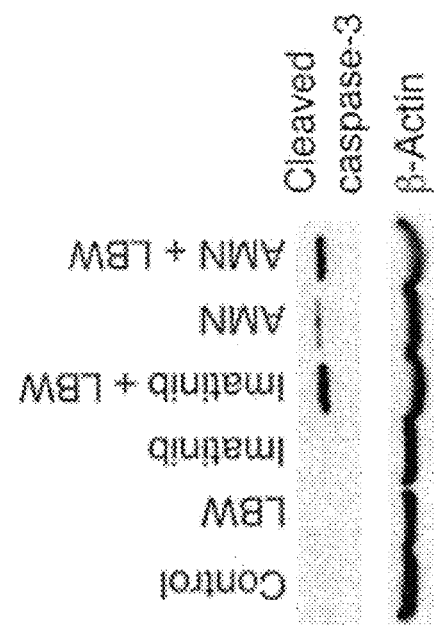

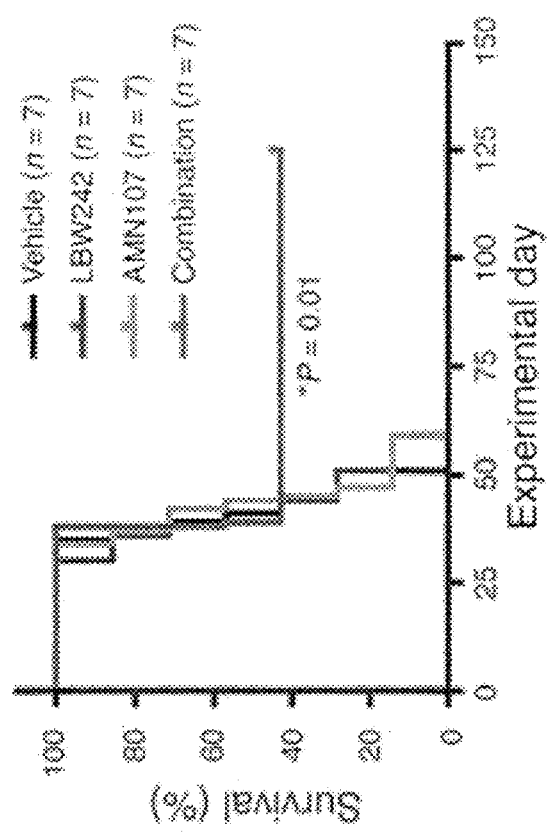

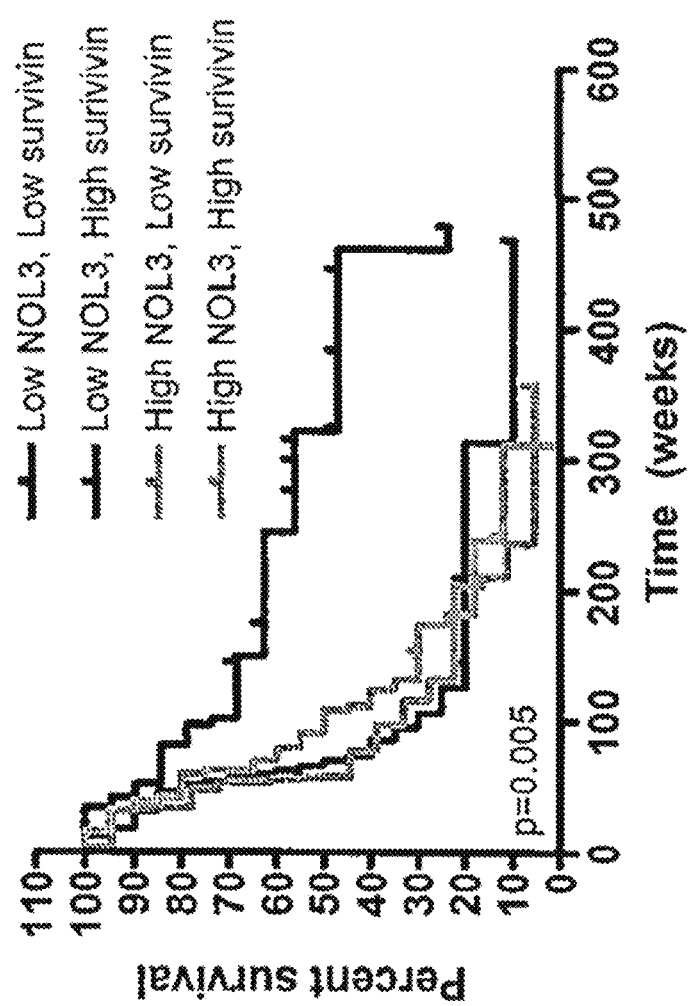

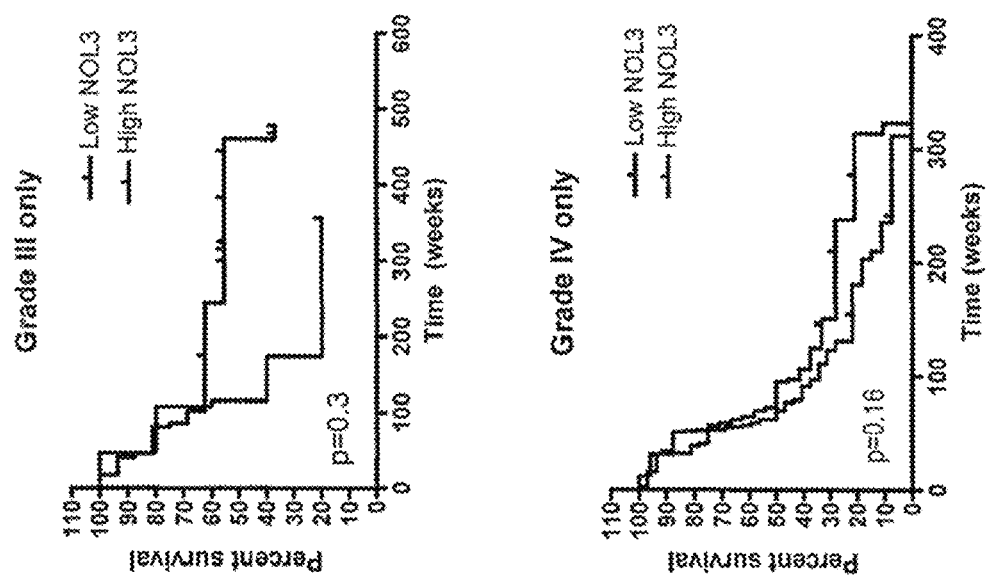

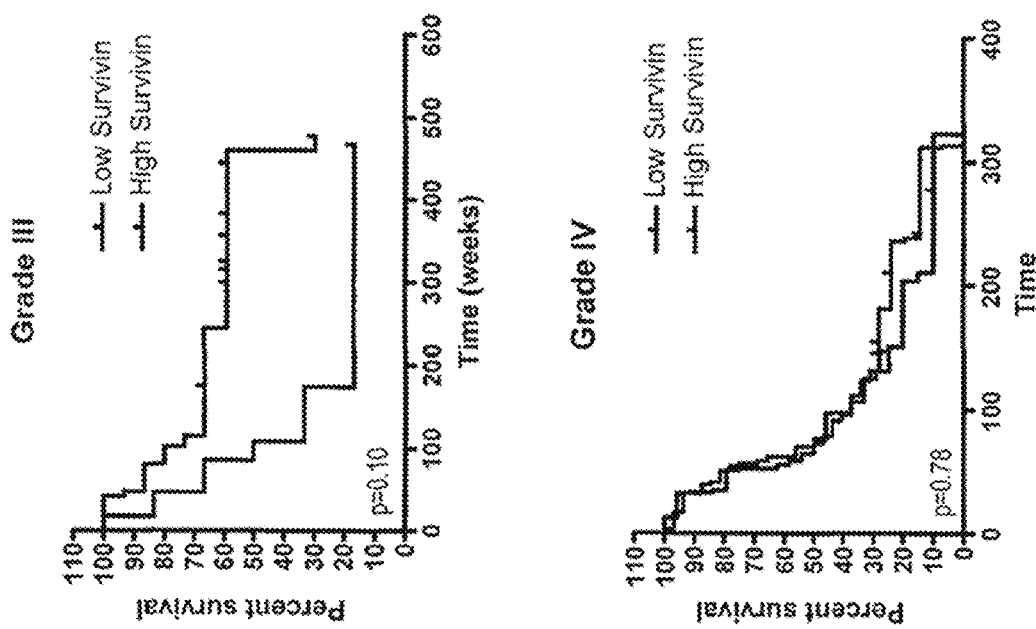

NOL3 IS A PREDICTOR OF PATIENT OUTCOME

RELATED APPLICATIONS

This application is a continuation of U.S. patent application Ser. No. 14/464,394, filed Aug. 20, 2014, issued as U.S. Pat. No. 9,533,980, which is a continuation of U.S. patent application Ser. No. 12/685,411, filed Jan. 11, 2010, issued as U.S. Pat. No. 8,841,067, with claims priority to U.S. Provisional Application No. 61/143,517, filed Jan. 9, 2009. The entire contents of this patent application is hereby incorporated herein by reference.

BACKGROUND OF THE INVENTION

The treatment of malignant gliomas remains one of the greatest challenges facing adult and pediatric oncologists today. At the most severe end of the spectrum is glioblastoma muitiforme (GBM)—among the most malignant of cancers, with a median survival of less than 12 months and an inherent resistance to both chemo- and radio-therapeutics (DeAngelis, N. Engl. J. Med. 344, 114-123, 2001). While initial treatment of GBM with surgery, radiotherapy and chemotherapy often produces some palliation of symptoms, these tumors almost universally recur with an unrelenting progression to death. Despite great advances in our understanding of the molecular causes of GBM (Kitange et al., Curr. Opin. Oncol. 15, 187-203, 2003), there has been very little improvement in outcomes for patients with GBM.

SUMMARY OF THE INVENTION

Strategies for the treatment of malignant gliomas are urgently needed. The present invention is based, at least in part, on the discovery that NOL3 expression levels have a significant impact on clinical outcome in patients having cancer. This invention is also based on the further discovery that a reduction in NOL3 expression is necessary for synergistic inhibition of tumor cell growth affected by growth factor receptor inhibitors, e.g., tyrosine kinase inhibitors, and inhibitors of inhibitor of apoptosis proteins (IAPs). In addition, reduction of NOL3 expression was shown to sensitize cells to the pro-apoptotic effects of IAP inhibitors.

Based at least in part on the above observations, the invention features, in a first aspect, a method for determining the prognosis for survival of a cancer patient, which includes measuring a level of NOL3 expression in a cancer cell-containing sample from the patient, and comparing the level of NOL3 expression in the sample to a reference level of NOL3 expression, wherein a higher level of NOL3 relative to said reference level correlates with decreased survival of the patient, and an equivalent or lower level of NOL3 relative to said reference level correlates with increased survival of the patient.

In a second aspect, the invention pertains to a method for determining the prognosis for survival of a cancer patient, which includes measuring a level of NOL3 expression in a cancer cell-containing sample from the patient, measuring the level of survivin expression in a cancer cell-containing sample from said patient, and comparing the level of NOL3 expression in the sample to a reference level of NOL3 expression, and comparing the level of survivin expression in the sample to a reference level of survivin expression, wherein a higher level of NOL3 and a higher level of survivin relative to said reference levels correlates with decreased survival of the patient, and wherein an equivalent or lower level of NOL3 and an equivalent or lower level of survivin relative to said reference levels correlates with increased survival of said patient.

In another aspect, the present invention pertains to a method of diagnosing the grade or stage of a tumor in a subject, which includes measuring a level of NOL3 expression in a cancer cell-containing sample from said subject, and comparing the level of NOL3 expression in said sample to a reference level of NOL3 expression, wherein a higher level of NOL3 relative to said reference level correlates with worsening grade or stage of said tumor.

In yet another aspect, the present invention relates to a method of identifying a compound as an anti-cancer agent, which includes treating a cell line expressing NOL3 with the compound, and determining the change in the level of NOL3 expression following treatment, wherein a compound which reduces the level of NOL3 expression is identified as an anti-cancer agent.

In a further aspect, the present invention relates to a method of predicting responsiveness to an anti-cancer agent in a subject having cancer, wherein said anti-cancer agent reduces the expression or activity of NOL3. The method includes measuring the level of NOL3 expression in a cancer cell-containing sample from the subject, and comparing the level of NOL3 expression in the sample to a reference level of NOL3 expression, wherein a higher level of NOL3 expression relative to the reference level predicts responsiveness of the subject to the anti-cancer agent.

In an additional aspect, the present invention pertains to a method of predicting responsiveness to an IAP inhibitor, which includes, measuring the level of NOL3 expression in a cancer cell-containing sample from the subject, and comparing the level of NOL3 expression in the sample to a reference level of NOL3 expression, wherein an equivalent or lower level of NOL3 expression relative to the reference level predicts responsiveness of the subject to the IAP inhibitor.

In an yet another aspect, the present invention relates to a method of selecting a subject having cancer for a treatment regimen, which includes measuring the level of NOL3 expression in a cancer cell-containing sample from the subject, comparing the level of NOL3 expression in the sample to a reference level of NOL3 expression, and selecting the subject for a treatment regimen, wherein a subject having a higher level of NOL3 expression relative to the reference level is selected for a treatment regimen comprising an agent that reduces the expression or activity of NOL3.

In an additional aspect, the present invention relates to a method of selecting a subject having cancer for a treatment regimen, which includes, measuring the level of NOL3 expression in a cancer cell-containing sample from the subject, comparing the level of NOL3 expression in the sample to a reference level of NOL3 expression, and selecting the subject for a treatment regimen, wherein a subject having an equivalent or lower level of NOL3 expression relative to the reference level is selected for a treatment regimen comprising an IAP inhibitor.

The present invention further provides a method for selecting a subject having cancer for a treatment regimen, which includes measuring the level of NOL3 expression in a cancer cell-containing sample from the subject, comparing the level of NOL3 expression in the sample to a reference level of NOL3 expression, and selecting the subject for a treatment regimen, wherein a subject having a higher level of NOL3 expression relative to the reference level is selected for a treatment regimen comprising an agent that reduces the expression or activity of NOL3. Furthermore, the method of this aspect additionally includes, treating the selected subject, wherein the treatment comprises administering to the selected subject a therapeutically effective amount of a growth factor receptor inhibitor; and, optionally treating the selected subject with a therapeutically effective amount of an IAP inhibitor.

In yet another aspect, the present invention provides a method for selecting a subject having cancer for a treatment regimen, which includes, measuring the level of NOL3 expression in a cancer cell-containing sample from the subject, comparing the level of NOL3 expression in the sample to a reference level of NOL3 expression, and selecting the subject for a treatment regimen, wherein a subject having an equivalent or lower level of NOL3 expression relative to the reference level is selected for a treatment regimen comprising an IAP inhibitor. Furthermore, the method of this aspect additionally includes, treating the selected subject, wherein the treatment comprises administering to the selected subject a therapeutically effective amount of an IAP inhibitor.

In a further aspect, the present invention provides a method of identifying a subject having cancer who is likely to benefit from treatment with an IAP inhibitor, which includes, assaying the level of NOL3 expression in a cancer cell-containing sample from the subject, assaying the level of NOL3 expression in a reference sample, and correlating an equivalent or lower level of NOL3 expression in the cancer cell containing sample relative to the level of NOL3 expression in the reference sample with a subject who is likely to benefit from treatment with an IAP inhibitor.

In another aspect, the present invention provides a method of identifying a subject having cancer who is likely to have an increased prognosis for survival, which includes, assaying the level of NOL3 expression in a cancer cell-containing sample from the subject, assaying the level of survivin expression in a cancer cell-containing sample from the subject, assaying the level NOL3 expression in a reference sample, assaying the level of survivin expression in a reference sample, and correlating an equivalent or lower level of NOL3 and an equivalent or lower level of survivin relative to the reference levels with a subject who is likely to have an increased prognosis for survival.

In a one embodiment of the above aspects, NOL3 refers to NOL3 mRNA. In another embodiment of the above aspects, NOL3 refers to NOL3 polypeptide. In yet another embodiment of the above aspects, the level of survivin expression is a level of survivin mRNA expression or a level of survivin protein expression.

In another embodiment of the above aspects, the level of NOL3 mRNA expression in a sample is determined by a technique selected from the group including Northern blot, RT-PCR, Quantitative RT-PCR (QPCR), non-PCR amplification methods (e.g., strand displacement amplification (SDA), rolling-circle amplification (RCA), multiple-displacement amplification (MDA), transcription meditated amplification (TMA), and nucleic acid sequence based amplification (NASBA)), Luminex bead analysis, in situ hybridization, and gene expression microarray analysis.

In an additional embodiment of the above aspects, the level of NOL3 polypeptide expression in a sample is determined by a technique selected from the group including Western blot, immunohistochemistry, indirect immunofluorescence, direct immunofluorescence, mass spectrometry, intracellular flow cytometry, enzyme-linked immunosorbent assay (ELISA), and antibody microarray analysis.

In a further embodiment of the above aspects, the level of survivin expression in a sample is determined by a technique selected from the group including Northern blot, RT-PCR, Quantitative RT-PCR (QPCR), in situ hybridization, gene expression microarray analysis, Western blot, immunohistochemistry, indirect immunofluorescence, direct immunofluorescence, mass spectrometry, intracellular flow cytometry, enzyme-linked immunosorbent assay (ELISA), and antibody microarray analysis.

In another embodiment of the above aspects, survival is overall survival. In a preferred embodiment of the above aspects, survival is disease-free survival or progression free survival.

In another embodiment of the above aspects, the sample is a tumor tissue sample.

In an additional embodiment of the above aspects, the reference level is obtained from a normal tissue sample.

In one embodiment of the above aspects, the cancer is a carcinoma. In a preferred embodiment of the above aspects, the carcinoma is selected from the group consisting of ovarian carcinoma, breast carcinoma, prostate carcinoma, colorectal carcinoma, and small cell lung carcinoma.

In another embodiment of the above aspects, the cancer is a glioma. In a preferred embodiment of the above aspects, the glioma is selected from the group consisting of an astrocytoma, an ependymoma, an oligodendroglioma, a mixed glioma, and glioblastoma multiforme.

In a further embodiment of the above aspects, the cancer is a sarcoma. In a preferred embodiment of the above aspects, the sarcoma is selected from the group consisting of osteosarcoma, chondrosarcoma, leiomyosarcoma, gastrointestinal stromal tumor (GIST), Ewing's sarcoma, Askin's tumor, malignant hemangioendothelioma, malignant schwannoma, and soft tissue sarcoma (e.g., alveolar soft part sarcoma, angiosarcoma, cystosarcoma phylloides, dermatofibrosarcoma, desmoid tumor, desmoplastic small round cell tumor, epithelioid sarcoma, extraskeletal chondrosarcoma, extraskeletal osteosarcoma, fibrosarcoma, hemangiopericytoma, hemangiosarcoma, Kaposi's sarcoma, liposarcoma, lymphangiosarcoma, lymphosarcoma, malignant fibrous histiocytoma, neurofibrosarcoma, rhabdomyosarcoma, and synovial sarcoma).

In yet another embodiment of the above aspects, the cancer is a hematologic malignancy. For example, the hematologic malignancy is selected from the group including acute leukemia, chronic leukemia, multiple myeloma, and lymphoma.

In one embodiment of the above aspects, the cancer comprises a high grade tumor. In a preferred embodiment of the above aspects, the tumor is selected from the group consisting of a grade III tumor, a grade IV tumor, and a recurrent tumor.

In another preferred embodiment of these aspects, a slight increase in NOL3 mRNA expression or NOL3 polypeptide expression correlates with a grade III tumor, a moderate increase correlates with a grade IV tumor, and a large increase correlates with a recurrent tumor.

In one embodiment of the above aspects, the compound of the invention is a small molecule. In another embodiment, the compound of the invention is a biologic agent. In an additional embodiment of the above aspects, the compound further inhibits growth factor receptor-mediated signaling.

In one embodiment of the above aspects, the anti-cancer agent of the invention is a small molecule. In another embodiment, the anti-cancer agent of the invention is a biologic agent. In an additional embodiment of the above aspects, the anti-cancer agent further inhibits growth factor receptor-mediated signaling. In an exemplary embodiment of the above aspects, the anti-cancer agent is an inhibitor of receptor tyrosine kinases. In another embodiment the anti-cancer agent is an epidermal growth factor receptor (EGFR) tyrosine kinase inhibitor or an insulin-like growth factor-1 receptor (IGF-1R) tyrosine kinase inhibitor; for example, the EGFR tyrosine kinase inhibitor is PKI166 (Hoekstra et al., Clinical Cancer Research Vol. 11, 6908-6915, Oct. 1, 2005, incorporated herein by reference in its entirety) and the IGF-1R tyrosine kinase inhibitor is AEW541 (Garcia-Echeverria et al., Cancer Cell. 2004 March; 5(3):231-9, incorporated herein by reference in its entirety). In a preferred embodiment of the above aspects, the anti-cancer agent is a platelet derived growth factor receptor (PDGFR) kinase inhibitor; for example, the PDGFR kinase inhibitor is imatinib.

In additional embodiment, the anti-cancer agent of the invention is identified according to the method of any one of the above aspects. In another embodiment, the present invention relates to a method of treating a cancer in a subject, comprising administering to the subject the anti-cancer agent identified according to the method of any one of the above aspects.

In one embodiment of the above aspects, the anti-cancer agent of the invention is administered in combination with an IAP (Inhibitor of Apoptosis Proteins) inhibitor.

In a preferred embodiment of the above aspects, the IAP inhibitor is LBW242. In another preferred embodiment the IAP inhibitors of the invention and methods of making them are disclosed in WO 2005/097791 and WO 2008/016893, both herein incorporated by reference in their entirety.

The present invention relates to novel compounds of formula (I):

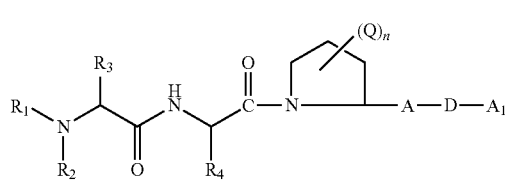

or pharmaceutically acceptable salts thereof, wherein
$R_1$ is H, $C_1$-$C_4$ alkyl, $C_2$-$C_4$ alkenyl, $C_2$-$C_4$ alkynyl or $C_3$-$C_{10}$ cycloalkyl, which $R_1$ may be unsubstituted or substituted:
$R_2$ is H, $C_1$-$C_4$ alkyl, $C_2$-$C_4$ alkenyl, $C_2$-$C_4$ alkynyl, $C_3$-$C_{10}$ cycloalkyl which $R_2$ may be unsubstituted or substituted:
$R_3$ is H, $CF_3$, $C_2F_5$, $C_1$-$C_4$ alkyl, $C_2$-$C_4$ alkenyl, $C_2$-$C_4$ alkynyl, $CH_2$—Z, or
$R_2$ and $R_3$, taken together with the nitrogen atom to which they are attached, form a heterocyclic ring, which alkyl, alkenyl, alkynyl or het ring may be unsubstituted or substituted;
Z is H, OH, F, Cl, $CH_3$, $CH_2Cl$, $CH_2F$ or $CH_2OH$;
$R_4$ is $C_{0-10}$ alkyl, $C_{0-10}$ to alkenyl, $C_{0-10}$ alkynyl, $C_3$-$C_{10}$ cycloalkyl, wherein the $C_{0-10}$ alkyl, or cycloalkyl group is unsubstituted or substituted;
A is het, which may be substituted or unsubstituted,
D is $C_1$-$C_7$ alkylene or $C_2$-$C_9$ alkenylene, C(O), O, $NR_7$, S(O)r, C(O)—$C_1$-$C_{10}$ alkyl, O—$C_1$-$C_{10}$ alkyl, S(O)r-$C_1$-$C_{10}$ alkyl, C(O) $C_{0}$-$C_{10}$ arylalkyl, $OC_0$-$C_{10}$ arylalkyl, or S(O)r $C_0$-$C_{10}$ arylalkyl, which alkyl and aryl groups may be unsubstituted or substituted;
r is 0, 1 or 2;
$A_1$ is a substituted or unsubstituted aryl or unsubstituted or substituted het which substituents on aryl and het are halo, alkyl, lower alkoxy, $NR_5R_6$, CN, $NO_2$ or $SR_5$;
each Q is independently H, $C_1$-$C_{10}$ alkyl, $C_1$-$C_{10}$ alkoxy, aryl $C_1$-$C_{10}$ alkoxy, OH, O—$C_1$-$C_{10}$ alkyl, $(CH_2)_{0-6}$—$C_3$-$C_7$ cycloalkyl, aryl, aryl $C_1$-$C_{10}$ alkyl, O—$(CH_2)_{0-6}$ aryl, $(CH_2)_{1-6}$ het, het, O—$(CH_2)_{1-6}$ het, —$OR_{11}$, C(O) $R_{11}$, —C(O)N($R_{11}$)($R_{12}$), N($R_{11}$)($R_{12}$), $SR_{11}$, S(O)$R_{11}$, S(O)$_2R_{11}$, S(O)$_2$—N($R_{11}$)($R_{12}$), or $NR_{11}$—S(O)$_2$—($R_{12}$), wherein alkyl, cycloalkyl and aryl are unsubstituted or substituted;
n is 0, 1, 2 or 3, 4, 5, 6 or 7;
het is a 5- to 7-membered monocyclic heterocyclic ring containing 1-4 heteroring atoms selected from N, O and S or an 8- to 12-membered fused ring system that includes one 5- to 7-membered monocyclic heterocyclic ring containing 1, 2 or 3 heteroring atoms selected from N, O and S, which het is unsubstituted or substituted;
$R_{11}$ and $R_{12}$ are independently H, $C_1$-$C_{10}$ alkyl, $(CH_2)_{0-6}$—$C_3$-$C_7$ cycloalkyl, $(CH_2)_{0-6}$—$(CH)_{0-1}$ (aryl)$_{1-2}$, C(O)—$C_1$-$C_{10}$ alkyl, —C(O)—$(CH_2)_{1-6}$—$C_3$-$C_7$ cycloalkyl, —C(O)—O—$(CH_2)_{0-6}$-aryl, —C(O)—$(CH_2)_{0-6}$—O-fluorenyl, C(O)—NH—$(CH_2)_{0-6}$-aryl, C(O)—$(CH_2)_{0-6}$-aryl, C(O)—$(CH_2)_{1-6}$-het, —C(S)—$C_1$-$C_{10}$alkyl, —C(S)—$(CH_2)_{1-6}$—$C_3$-$C_7$ cycloalkyl, —C(S)—O—$(CH_2)_{0-6}$-aryl, —C(S)—$(CH_2)_{0-6}$—O-fluorenyl, C(S)—NH—$(CH_2)_{0-6}$-aryl, —C(S)—$(CH_2)_{0-6}$-aryl or C(S)—$(CH_2)_{1-6}$-het, C(O)$R_{11}$, C(O)$NR_{11}R_{12}$, C(O) $OR_{11}$, S(O)$_nR_{11}$, S(O)$_mNR_{11}R_{12}$, m=1 or 2, C(S)$R_{11}$, C(S)$NR_{11}R_{12}$, C(S)$OR_1$, wherein alkyl, cycloalkyl and aryl are unsubstituted or substituted; or $R_{11}$ and $R_{12}$ are a substituent that facilitates transport of the molecule across a cell membrane, or
$R_{11}$ and $R_{12}$ together with the nitrogen atom form het, wherein the alkyl substituents of $R_{11}$ and $R_{12}$ may be unsubstituted or substituted by one or more substituents selected from $C_1$-$C_{10}$ alkyl, halogen, OH, O—$C_1$-$C_6$ alkyl, —S—$C_1$-$C_6$ alkyl, $CF_3$ or $NR_{11}R_{12}$; substituted cycloalkyl substituents of $R_{11}$ and $R_{12}$ are substituted by one or more substituents selected from a $C_2$-$C_{10}$ alkene; $C_1$-$C_6$ alkyl; halogen; OH; O—$C_1$-$C_6$ alkyl; S—$C_1$-$C_6$ alkyl, $CF_3$; or $NR_{11}R_{12}$ and substituted het or substituted aryl of $R_{11}$ and $R_{12}$ are substituted by one or more substituents selected from halogen, hydroxy, $C_1$-$C_4$ alkyl, $C_1$-$C_4$ alkoxy, nitro, CNO—C(O)—$C_1$-$C_4$alkyl and C(O)—O—$C_1$-$C_4$-alkyl
$R_5$, $R_6$ and $R_7$ are independently hydrogen, lower alkyl, aryl, aryl lower alkyl, cycloalkyl, or cycloalkyl lower alkyl, C(O)$R_5$; S(O)$R_5$, C(O)OR$_5$C(O)NR$_5R_6$, and
the substituents on $R_1$, $R_2$, $R_3$, $R_4$, Q, and A and $A_1$ groups are independently halo, hydroxy, lower alkyl, lower alkenyl, lower alkynyl, lower alkanoyl, lower alkoxy, aryl, aryl lower alkyl, amino, amino lower alkyl, diloweralkylamino, lower alkanoyl, amino lower alkoxy, nitro, cyano, cyano lower alkyl, carboxy, lower carbalkoxy, lower alkanoyl, aryloyl, lower arylalkanoyl, carbamoyl, N-mono- or N,N-dilower alkyl carbamoyl, lower alkyl carbamic acid ester, amidino, guanidine, ureido, mercapto, sulfo, lower alkylthio, sulfoamino, sulfonamide, benzosulfonamide, sulfonate, sulfanyl lower alkyl, aryl sulfonamide, halogen substituted aryl sulfonate, lower alkylsulfinyl, arylsulfinyl; aryl-lower alkylsulfinyl, lower alkylarylsulfinyl, lower alkylsulfonyl, arylsulfonyl, aryl-lower alkylsulfonyl, lower aryl alkyl lower alkylarylsulfonyl, halogen-lower alkylmercapto, halogen-lower alkylsulfonyl, phosphono (—P (=O)(OH)$_2$), hydroxy-lower alkoxy phosphoryl or di-lower alkoxyphosphoryl, (R$_9$)NC(O)—NR$_{10}$R$_{13}$, lower alkyl carbamic acid ester or carbamates or —NR$_8$R$_{14}$, wherein R$_8$ and R$_{14}$ can be the same or different and are independently H or lower alkyl, or R$_8$ and R$_{14}$, together with the N atom, form a 3- to 8-membered heterocyclic ring containing a nitrogen heteroring atoms and may optionally contain one or two additional heteroring atoms selected from nitrogen, oxygen and sulfur, which heterocyclic ring may be unsubstituted or substituted with lower alkyl, halo, lower alkenyl, lower alkynyl, hydroxy, lower alkoxy, nitro, amino, lower alkyl, amino, diloweralkyl amino, cyano, carboxy, lower carbalkoxy, formyl, lower alkanoyl, oxo, carbamoyl, N-lower or N,N-dilower alkyl carbamoyl, mercapto, or lower alkylthio; and R$_9$, R$_{10}$ and R$_{13}$ are independently hydrogen, lower alkyl, halogen substituted lower alkyl, aryl, aryl lower alkyl, halogen substituted aryl, halogen substituted aryl lower alkyl.

As used herein, the term "aryl" is defined as an aromatic radical having 6-14 ring carbon atoms, and no ring heteroatoms. The aryl group may be monocyclic or fused bicyclic or tricyclic. It may be unsubstituted or substituted by one or more, preferably one or two, substituents, wherein the substituents are as described herein. As defined herein, the aryl moiety may be completely aromatic regardless of whether it is monocyclic or bicyclic. However, if it contains more than one ring, as defined herein, the term aryl includes moieties wherein at least one ring is completely aromatic while the other ring(s) may be partially unsaturated or saturated or completely aromatic. Preferred "aryl" is phenyl, naphthyl or indanyl. The most preferred aryl is phenyl.

"Het", as used herein, refers to heteroaryl and heterocyclic compounds containing at least one S, O or N ring heteroatom. More specifically, "het" is a 5- to 7-membered heterocyclic ring containing 1-4 heteroatoms selected from N, O and S, or an 8- to 12-membered fused ring system including at least one 5- to 7-membered heterocyclic ring containing 1, 2 or 3 heteroatoms selected from N, O and S. Examples of het, as used herein, include unsubstituted and substituted pyrrolidyl, tetrahydrofuryl, tetrahydrothiofuryl, piperidyl, piperazyl, purinyl, tetrahydropyranyl, morpholino, 1,3-diazapanyl, 1,4-diazapanyl, 1,4-oxazepanyl, 1,4-oxathiapanyl, furyl, thienyl, pyrryl, pyrrolyl, pyrazolyl, triazolyl, tetrazolyl, indazolyl, oxadiazolyl, imidazolyl, pyrrolidyl, pyrrolidinyl, thiazolyl, oxazolyl, pyridyl, pyrazolyl, pyrazinyl, pyrimidinyl, isoxazolyl, pyrazinyl, quinolyl, isoquinolyl, pyridopyrazinyl, pyrrolopyridyl, furopyridyl, indolyl, benzofuryl, benzothiofuryl, benzoindolyl, benzothienyl, pyrazolyl, piperidyl, piperazinyl, indolinyl, morpholinyl, benzoxazolyl, pyrroloquinolyl, and the like. Heteroaryls are within the scope of the definition of het. Examples of heteroaryls are pyridyl, pyrimidinyl, quinolyl, thiazolyl and benzothiazolyl. The most preferred het are pyridyl, pyrimidinyl and thiazolyl. The het may be unsubstituted or substituted as described herein. It is preferred that it is unsubstituted or if substituted it is substituted on a carbon atom by halogen, especially fluorine or chlorine, hydroxy, C$_1$-C$_4$ alkyl, such as methyl and ethyl, C$_1$-C$_4$ alkoxy, especially methoxy and ethoxy, nitro, —O—C(O)—C$_1$-C$_4$ alkyl or —C(O)—O—C$_1$-C$_4$ alkyl, carbamoyl, N-mono- or N,N,-dilower alkyl carbamoyl, lower alkyl carbamic acid ester, amidino, guanidine, ureido, mercapto, sulfo, lower alkyl-thio, sulfoamino, sulfonamide, sulfonate, sulfanyl, SCN or nitro or on a nitrogen atom by C$_1$-C$_4$ alkyl, especially methyl or ethyl, —O—C(O)—C$_1$-C$_4$ alkyl or —C(O)—O—C$_1$-C$_4$ alkyl, such as carbomethoxy or carboethoxy.

When two substituents together with a commonly bound nitrogen are het, it is understood that the resulting heterocyclic ring is a nitrogen-containing ring, such as aziridine, azetidine, azole, piperidine, piperazine, morpholine, pyrrole, pyrazole, thiazole, oxazole, pyridine, pyrimidine, isoxazole, and the like, wherein such het may be unsubstituted or substituted as defined hereinabove.

Halogen is fluorine, chlorine, bromine or iodine, especially fluorine and chlorine.

Unless otherwise specified, "alkyl", either above or in combination, includes straight or branched chain alkyl, such as methyl, ethyl, n-propyl, isopropyl, n-butyl, sec-butyl, tert-butyl, n-pentyl and branched pentyl, n-hexyl and branched hexyl, and the like.

A "cycloalkyl" group means C$_3$-C$_{10}$ cycloalkyl having 3-10 ring carbon atoms and may be, e.g., cyclopropyl, cyclobutyl, cyclopentyl, cyclohexyl, cycloheptyl or cyclooctyl, cyclononyl and the like. The cycloalkyl group may be monocyclic or fused bicyclic. It is preferred that it is monocyclic. Moreover, the preferred cycloalkyl group is cyclopentyl or cyclohexyl. Most preferably, cycloalkyl is cyclohexyl. The cycloalkyl group may be fully saturated or partially unsaturated, although it is preferred that it is fully saturated. As defined herein, it excludes aryl groups. The cycloalkyl groups may be unsubstituted or substituted with any of the substituents defined below, preferably halo, hydroxy or C$_1$-C$_6$ alkyl, such as methyl.

Substituents that facilitate transport of the molecule across a cell membrane are known to those of skill in the medicinal chemistry arts [see, e.g., Gangewar S. et al., Drug Discov Today, Vol. 2, pp. 148-155 (1997); and Bundgaard H. and Moss J., Pharma Res, Vol. 7, p. 885 (1990)]. Generally, such substituents are lipophilic substituents. Such lipophilic substituents include a C$_6$-C$_{30}$ alkyl which is saturated, monounsaturated, polyunsaturated, including methylene-interrupted polyene, phenyl, phenyl which is substituted by one or two C$_1$-C$_8$ alkyl groups, C$_5$-C$_9$ cycloalkyl, C$_5$-C$_9$ cycloalkyl which is substituted by one or two C$_1$-C$_8$ alkyl groups, —X$_1$-phenyl, —X$_1$-phenyl which is substituted in the phenyl ring by one or two C$_1$-C$_8$ alkyl groups, X$_1$—C$_5$-C$_9$ cycloalkyl or X$_1$—C$_5$-C$_9$ cycloalkyl which is substituted by one or two C$_1$-C$_8$ alkyl groups; where X$_1$ is C$_1$-C$_{24}$ alkyl which is saturated, monounsaturated or polyunsaturated and straight or branched chain.

Unsubstituted is intended to mean that hydrogen is the only substituent.

Except as described herein, any of the above defined aryl, het, alkyl, alkenyl, alkynyl or cycloalkyl, may be unsubstituted or independently substituted by up to four, preferably one, two or three substituents, selected from the group consisting of: halo, such as Cl or Br; hydroxy; lower alkyl, such as C$_1$-C$_3$ alkyl; lower alkyl which may be substituted with any of the substituents defined herein; lower alkenyl; lower alkynyl; lower alkanoyl; lower alkoxy, such as methoxy; aryl, such as phenyl or naphthyl; substituted aryl, such as fluoro phenyl or methoxy phenyl; aryl lower alkyl, such as benzyl, amino, mono or di-lower alkyl, such as dimethylamino; lower alkanoyl amino acetylamino; amino lower alkoxy, such as ethoxyamine; nitro; cyano; cyano lower alkyl; carboxy; lower carbalkoxy, such as methoxy carbonyl; n-propoxy carbonyl or iso-propoxy carbonyl, lower aryloyl, such as benzoyl; carbamoyl; N-mono- or N,N di-lower alkyl carbamoyl; lower alkyl carbamic acid ester; amidino; guanidine; ureido; mercapto; sulfo; lower alkyl-thio; sulfoamino; sulfonamide; benzosulfonamide; sulfonate; sulfanyl lower alkyl, such as methyl sulfanyl; sulfoamino; aryl sulfonamide; halogen substituted or unsubstituted aryl sulfonate, such as chloro-phenyl sulfonate; lower alkylsulfinyl; arylsulfinyl; aryl-lower alkylsulfinyl; lower alkylarylsulfinyl; lower alkanesulfonyl; arylsulfonyl; aryl-lower alkylsulfonyl; lower aryl alkyl; lower alkylarylsulfonyl; halogen-lower alkylmercapto; halogen-lower alkylsulfonyl; such as trifluoromethane alkoxyphosphoryl; urea and substituted urea of the formula $(R_9)$ NC(O) N$(R_{10})$, $(R_{13})$, wherein $R_9$, $R_{10}$ and $R_{13}$ are as defined herein, such as urea or 3-trifluoro-methyl-phenyl urea; alkyl carbamic acid ester or carbamates, such as ethyl-Λ/-phenyl-carbamate; or —NR$_8$R$_{14}$, wherein R$_8$ and R$_{14}$ can be the same or different and are independently H; lower alkyl, e.g., methyl, ethyl or propyl; or R$_8$ and R$_{14}$, together with the N atom, form a 3- to 8-membered heterocyclic ring containing a nitrogen heterering atom and optionally one or two additional heterering atoms selected from the group consisting of nitrogen, oxygen and sulfur (e.g. piperazinyl, pyrazinyl, lower alkyl-piperazinyl, pyridyl, indolyl, thiophenyl, thiazolyl, benzothiophenyl, pyrrolidinyl, piperidino or imidazolinyl) where the heterocyclic ring may be substituted with any of the substituents defined hereinabove. Preferably the above mentioned alkyl, cycloalkyl, and aryl groups are independently unsubstituted or are substituted by lower alkyl, aryl, aryl lower alkyl, carboxy, lower carbalkoxy and especially halogen, —OH, —SH, —OCH$_3$, —SCH$_3$, —CN, —SCN or nitro.

As defined herein, the term "lower alkyl", when used alone or in combination, refers to alkyl containing 1-6 carbon atoms. The alkyl group may be branched or straight-chained, and is as defined hereinabove.

The term "lower alkenyl" refers to a alkenyl group which contains 2-6 carbon atoms. An alkenyl group is a hydrocarbyl group containing at least one carbon-carbon double bond. As defined herein, it may be unsubstituted or substituted with the substituents described herein. The carbon-carbon double bonds may be between any two carbon atoms of the alkenyl group. It is preferred that it contains 1 or 2 carbon-carbon double bonds and more preferably one carbon-carbon double bond. The alkenyl group may be straight chained or branched. Examples include ethenyl, 1-propenyl, 2-propenyl, 1-butenyl, 2-butenyl, 2-methyl-1-propenyl, 1,3-butadienyl and the like. The preferred alkenyl group is ethenyl.

The term "lower alkynyl", as used herein, refers to an alkynyl group containing 2-6 carbon atoms. An alkynyl group is a hydrocarbyl group containing at least one carbon-carbon triple bond. The carbon-carbon triple bond may be between any two carbon atom of the alkynyl group. It is preferred that the alkynyl group contains 1 or 2 carbon-carbon triple bonds and more preferably one carbon-carbon triple bond. The alkynyl group may be straight chained or branched. Examples include ethynyl, 1-propynyl, 2-propynyl, 1-butynyl, 2-butynyl and the like. The preferred alkynyl group is ethynyl.

As used herein, the term "aryl alkyl" refers to a aryl group connected to the main chain by a bridging alkylene group. Examples include benzyl, phenethyl, naphthylmethyl, and the like. The preferred aryl alkyl is benzyl. Similarly, cyano alkyl group refers to a cyano group connected to the main chain by a bridging alkylene group.

The term "alkyl aryl" on the other hand, refers to an alkyl group bridged to the main chain through a phenylene group. Examples include methylphenyl, ethylphenyl and the like.

As used herein, the term "lower alkanoyl" refers to a lower alkyl chain in which one of the carbon atoms is replaced by a C═O group. The C═O group may be present at one of the ends of the substituent or in the middle of the moiety. Examples include formyl, acetyl, 2-propanoyl, 1-propanoyl and the like.

The term "alkoxy" refers to an alkyl group as defined herein, connected to the main chain by an oxygen atom. Examples include methoxy, ethoxy and the like.

The term "lower thioalkyl" refers to an alkyl group, as defined herein, connected to the main chain by a sulfur atom. Examples include thiomethyl (or mercapto methyl), thio-ethyl (mercapto ethyl) and the like.

The term "lower carbalkoxy" or synonym thereto refers to an alkoxycarbonyl group, where the attachment to the main chain is through the aryl group (C(O)). Examples include methoxy carbonyl, ethoxy carbonyl and the like.

It is to be understood that the terminology C(O) refers to a —C═O group, whether it be ketone, aldehyde or acid or acid derivative. Similarly, S(O) refers to a —S═O group.

As used herein, the term S(O)r refers to the number of oxygen atoms bonded to the sulfur atom. When r=2, then S(O)r=SO$_2$, when r is 1, then S(O)r is SO; and when r=0, then S(O)r is S.

The term "C$_0$", as used herein, as part of a definition of alkyl as, e.g., C$_{0-10}$, refers to zero carbon atoms. Thus, "C$_0$-C$_{10}$ aryl alkyl" means that the aryl group is bonded directly to the main chain (C$_0$) or that there is a C$_1$-C$_{10}$ alkylene group bridging the main chain to an aryl group.

The term "(CH$_2$)$_{0-6}$" as part of definition of a larger group, e.g., (CH$_2$)$_{0-6}$ C$_3$-C$_7$ cycloalkyl, refers to a group that is not present (CH$_2$)$_0$, or to a group that contains 1-6 carbon atoms (CH$_2$)$_{1-6}$.

The term "(CH$_2$)$_{0-6}$—(CH)$_{0-1}$, (aryl)$_{1-2}$", in the definition of R$_{11}$ and R$_{12}$, is intended to mean one of the following (CH$_2$)$_{1-6}$-aryl, aryl, —CH(aryl)$_2$ or (CH$_2$)$_{1-6}$ (CH) (aryl)$_2$.

As used herein, the variable "n" refers to number of substitutents on the pyrrolidinyl (tetrahydropyrrolyl) ring. The term "n" is defined as 0-7 and it determines the number of Q substituents on the pyrrolidinyl (tetrahydro-pyrrolyl) ring. Q can only be present at the 2, 3, 4 or 5 positions of the pyrrolidinyl ring, i.e., at the carbon atoms of the pyrrolidinyl ring. Except for carbon number 2 that can allow for one substitution, each of other carbon atoms are saturated and each of them may have two substituents thereon. When n is 7, then each of the carbon atoms are bonded with Q as defined herein. Each Q may be the same or different. However, when n is 6, then one of the seven possible substituents is H, and the other five are Q, which can be the same or different. Further, when n is 5, then two of the possible substitutents are H, and the other five are independently Q, as defined herein. When n is 4, then three of the seven possible substituents are H, and the remainder are Q independently as defined herein. Where n is 3, then four of the seven possible substituents are H, and the other three are Q as defined herein. When n is 2, then two of the seven possible substituent are Q, and the remainder are H. When n is 1, then only one of the seven possible substituent is Q, and the remainder are H. Finally, when n is 0, all seven of the substituents are H.

It is to be understood that each of the Q substituents may be the same or they may be different. Where the plural form is used for compounds, salts, pharmaceutical preparations, this is intended to mean also a single compound, single pharmaceutical preparation, salt and the like.

It will be apparent to one of skill in the art that the compounds of the present invention can exist as a salt form, especially as an acid addition salt or a base addition salt. When a compound exists in a salt form, such salt forms are included within the scope of the invention. Although any salt form may be useful in chemical manipulations, such as purification procedures, only pharmaceutically acceptable salts are useful for the pharmaceutical products of the present invention.

Pharmaceutically acceptable salts include, when appropriate, pharmaceutically acceptable base addition salts and acid addition salts, for example, metal salts, such as alkali and alkaline earth metal salts, ammonium salts, organic amine addition salts, and amino acid addition salts, and sulfonate salts and the like. Acid addition salts include inorganic acid addition salts, such as hydrochloride, sulfate and phosphate; and organic acid addition salts, such as alkyl sulfonate, arylsulfonate, acetate, maleate, fumarate, tartrate, citrate and lactate and the like. Examples of metal salts are alkali metal salts, such as lithium salt, sodium salt and potassium salt; alkaline earth metal salts, such as magnesium salt and calcium salt, aluminum salt, and zinc salt and the like. Examples of ammonium salts are ammonium salts and tetramethylammonium salts and the like. Examples of organic amine addition salts are salts with morpholine and piperidine and the like. Examples of amino acid addition salts are salts with glycine, phenylalanine, glutamic acid and lysine and the like. Sulfonate salts include mesylate, tosylate and benzene sulfonic acid salts and the like.

In view of the close relationship between the compounds in free form and those in the form of their salts, including those salts that can be used as intermediates, e.g., in the purification or identification of the compounds, tautomers or tautomeric mixtures and their salts, any reference to the compounds hereinbefore and hereinafter especially the compounds of the formulae (I)-(VII), is to be understood as referring also to the corresponding tautomers of these compounds, especially of compounds of the formulae (I)-(VII), tautomeric mixtures of these compounds, especially of compounds of the formulae (I)-(VII), or salts of any of these, as appropriate and expedient and if not mentioned otherwise.

Any asymmetric carbon atom may be present in the (R)-, (S)- or (R,S)-configuration, preferably in the (R)- or (S)-configuration. Substituents at a ring at atoms with saturated bonds or substituents on carbon-carbon double bonds may, if possible, be present in cis-(=Z—) or trans (=E-) form. The compounds may thus be present as mixtures of isomers or preferably as pure isomers, preferably as enantiomerically pure diastereomers or pure enantiomers.

The present invention includes within its scope, prodrugs of the compounds of the invention. In general, such prodrugs will be functional derivatives of a compound of the invention which are readily convertible in vivo into the compound from which it is notionally derived. Conventional procedures for the selection and preparation of suitable prodrugs are described, e.g., in Design of Prodrugs, H. Bundgaard, Ed., Elsevier (1985).

The preferred $R_1$ group is H and $C_1$-$C_4$ alkyl especially methyl. $R_1$ may be unsubstituted or substituted and is most preferably unsubstituted. The most preferred values of $R_1$ is H, methyl and ethyl, and especially methyl or ethyl and most especially methyl.

$R_2$ is preferably H or $C_1$-$C_4$ alkyl, especially methyl. $R_2$ may be unsubstituted or substituted. It is most preferably unsubstituted. It is preferred that $R_2$ is hydrogen.

$R_3$ is preferably H or $C_1$-$C_4$ alkyl especially hydrogen methyl, or ethyl and most especially methyl or ethyl, and most especially methyl, which may be unsubstituted or substituted. $R_3$ may be unsubstituted or substituted as defined herein. It is preferred that it is unsubstituted methyl.

$R_4$ is preferably $C_5$-$C_7$ cycloalkyl, and more preferably cyclopentyl or cyclohexyl, isopropyl, and most preferably is cyclohexyl. One may be substituted or unsubstituted. If substituted, it is preferably substituted with lower alkyl especially methyl. However, it is preferred that $R_4$ is unsubstituted.

The pyrrolidinyl ring can have up to six independent Q substituents thereon. It is preferred that n is 0-3 and even more preferably, n is 0, 1, or 2 and even more preferably, n is 0 or 1 and most preferably n is 0. If Q is present, it is preferred that Q is lower alkyl, alkoxyl, alylthio, amino, sulfonylamino, acylamino.

A is preferably a 5- or 6-membered het, and more preferably is 5- or 6-membered heteroaryl, especially a 5 or 6-member heteroaryl ring containing at least one ring hetero atom selected from the group consisting of nitrogen, oxygen and sulfur and containing 1-4 ring heteroatoms. Preferably, it contains 1 or 2 ring heteroatoms, and more preferably contains at least 1 N ring heteroatom, and the other ring heteroatom is, if present, a nitrogen, oxygen or sulfur, and more preferably if present is nitrogen or sulfur, and most preferably, if present, is sulfur. The preferred value of A is pyridyl, pyrimidinyl, and thiazolyl. A may be unsubstituted or substituted. It is preferred that A is unsubstituted or substituted with alkyl, amino or halo.

D is preferably O or C(O), $NR_7$ or S(O)r and more preferably is O or C(O), $CH_3N$, HN or S and even more preferably is O or C(O) or $CH_3N$, HN and most preferably O or C(O).

$A_1$ is preferably a substituted aryl or an unsubstituted or substituted 5- or 6-membered het and more preferably is a substituted aryl or a 5- or 6-membered unsubstituted or substituted heteroaryl. Most preferably, $A_1$ is a substituted aryl. The most preferred value of $A_1$ is a substituted phenyl.

It is preferred that if A is aryl, it is monosubstituted, disubstituted or trisubstituted by one of the substituents enumerated hereinabove. In an embodiment, $A_1$ is substituted by halo, especially fluoro or chloro, and most preferably fluoro.

Another embodiment of the compound of formula (I) has formula (II):

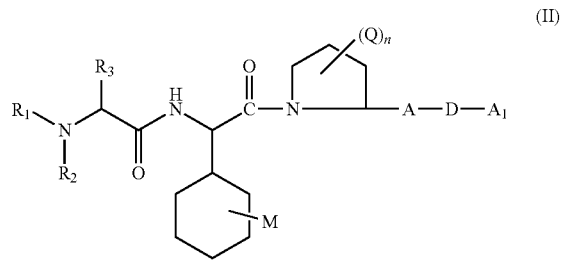

(II)

or pharmaceutically acceptable salts thereof, wherein
$R_1$, $R_2$, $R_3$, Q, n, A, D and $A_1$ are as described hereinabove; and M is a H or a substituent on the cyclohexyl group, as defined above.

It is preferred that M is H, halo; hydroxy; lower alkyl; lower alkenyl; lower alkynyl; formyl; lower alkanoyl; aryl, cycloalkyl, aryl lower alkyl, lower alkoxy; aryl lower alkyl, amino; amino, mono- or disubstituted lower alkylamino; amino lower alkyl; lower alkanoyl; amino lower alkoxy; nitro; cyano; cyano lower alkyl; carboxy; lower carbalkoxy; lower alkanoyl; arylyol; lower arylalkanoyl; carbamoyl; N-mono- or N,N-lower alkyl carbamoyl; lower alkyl carbamic acid ester; —NR$_{15}$R$_{16}$, wherein R$_{15}$ and R$_{16}$ can be the same or different and are independently H or lower alkyl; or R$_{15}$ and R$_{16}$ together with the N atom form a 3- to 8-membered heterocyclic ring containing 1-4 nitrogen, oxygen or sulfur ring atoms. The preferred value of M is hydrogen. The preferred values of R$_1$, R$_2$, R$_3$, n, Q, A, D, A$_1$ and Y described hereinabove are also applicable in this embodiment.

In an another embodiment, preferred are compounds of formula (II) or pharmaceutically acceptable salts thereof, wherein
R$_1$ is H or C$_1$-C$_4$ alkyl, which may be unsubstituted or substituted;
R$_2$ is H or C$_1$-C$_4$-alkyl, which may be unsubstituted or substituted;
R$_3$ is H or C$_1$-C$_4$ alkyl, which may be unsubstituted or substituted;
R$_4$ is cyclohexyl, isopropyl, which may be unsubstituted or substituted;
A is 5- or 6-membered nitrogen, oxygen or sulfur containing heteroaryl, which may be unsubstituted or substituted;
D is C(O), O, S(O)r or NR$_7$;
A$_1$ is aryl, which is substituted; and
n is as defined hereinabove.

The preferred definition of the various variables described hereinabove are also applicable in this embodiment. However, the preferred values of R$_1$ is H or methyl. In addition, the preferred value of R$_2$ is hydrogen or methyl. The preferred value of R$_3$ is hydrogen, ethyl or methyl.

It is preferred that n is 0, that is, the remaining substituents on the pyrrolidine ring are all hydrogens.

The preferred values of A is a 5- or 6-membered heteroaryl ring containing at least 1 nitrogen ring atom. Preferably, it contains 1 nitrogen ring atom and 4-5 carbon ring atoms or 2 ring heteroatoms and 3-4 ring carbon atoms, wherein 1 of the ring atoms is a nitrogen atom, and the other ring heteroatom is an oxygen, sulfur or nitrogen atom. Examples include pyridyl (e.g., 2-pyridyl, 3-pyridyl, or 4-pyridyl), pyrimidinyl, thiazolyl, oxazolyl and pyrrolyl, e.g., 2-pyrrolyl. In an embodiment A$_1$ is substituted aryl, especially substituted phenyl, wherein the substituents are as defined hereinabove.

The preferred values of D is C(O), O, S, NR$_7$ and most especially C(O) or O.

Another embodiment is a compound of formula (I) has formula (IV):

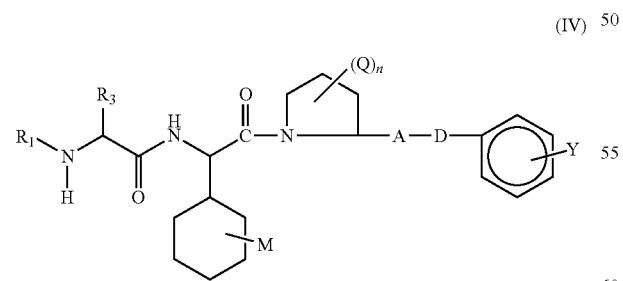

(IV)

or pharmaceutically acceptable salts thereof, wherein
R$_1$, R$_3$, Q, n, A$_1$, D, M are as defined hereinabove; and
Y is halo, lower alkoxy, NR$_5$R$_6$, CN, NO$_2$ or SR$_5$, wherein R$_5$ and R$_6$ are defined above.
In an embodiment, Y is halo. It is preferred that Y is on the para position. The preferred value of R$_1$, R$_3$, Q, n, A$_1$ and D described hereinabove are also applicable in this embodiment. It is most preferred that Y is fluorine.

A further embodiment is directed to compounds of the formula (V):

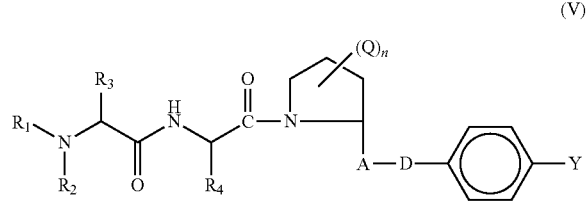

(V)

or pharmaceutically acceptable salts thereof,
wherein
R$_2$ is H;
R$_4$ is unsubstituted cyclohexyl; and
R$_1$, R$_3$, A, D and Y are as defined hereinabove.

The various values of R$_1$, R$_3$, A, D, Q, n and Y described hereinabove are also applicable. In the compound of formula (V), in an embodiment, as described hereinabove, n is 0.

In a preferred embodiment of the present invention, R$_3$ and R$_4$ have the stereochemistry indicated in formula (VI), with the definitions of the various substituents described hereinabove with respect to formulae (I)-(V) also applying to compounds of formula (VI). Thus, another embodiment of the present invention is directed to compounds of formula (VI):

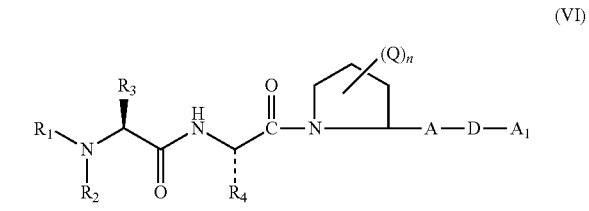

(VI)

or pharmaceutically acceptable salts thereof, wherein R$_1$, R$_2$, R$_3$, R$_4$, Q, n, A, D and A$_1$ are as defined in any of the embodiments hereinabove.

In another embodiment of the present invention, the compound of formula (VI) has the formula (VII):

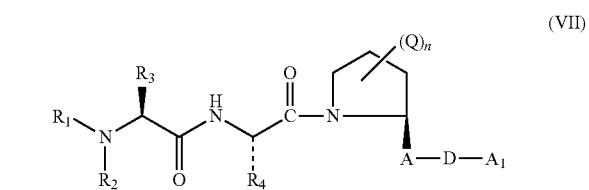

(VII)

or pharmaceutically acceptable salts thereof, wherein R$_1$, R$_2$, R$_3$, R$_4$, A, D, Q, A$_1$ and n are as defined hereinabove.

It is to be understood that the preferred values of the variables described hereinabove with respect to compounds of formulae (I)-(V) are also applicable to the compounds of formulae (VI) and (VII).

The following examples are intended to illustrate, but not further limit, the invention.

(S)—N—((S)-1-Cyclohexyl-2-{(S)-2-[4-(4-fluoro-benzoyl)-thiazol-2-yl]-pyrrolidin-1-yl}-2-oxo-ethyl)-2-methylamino-propionamide (S)—N—[S-Cyclohexyl-(ethyl-{(S)-1-[5-(4-fluoro-benzoyl)-pyridin-3-yl]-propyl}-carbamoyl)-methyl]-2-methylamino-propionamide (S)—N—((S)-1-Cyclohexyl-2-{(S)-2-[5-(4-fluoro-phenoxy)-pyridin-3-yl]-pyrrolidin-1-yl}-2-oxo-ethyl)-2-methylamino-propionamide (S)—N—((S)-1-Cyclohexyl-2-{(S)-2-[4-(4-fluoro-phenoxy)-pyridin-2-yl]-pyrrolidin-1-yl}-2-oxo-ethyl)-2-methylamino-propionamide (S)—N—[(S)-Cyclohexyl-2-((S)-2-{5-fluoro-2-[(4-fluoro-phenyl)-methylamino]-pyridin-4-yl}-pyrrolidin-1-yl)-2-oxo-ethyl]-2-methylaminopropionamide (S)—N—((S)-1-Cyclohexyl-2-{(S)-2-[4-(4-fluoro-benzoyl)-5-methyl-thiazol-2-yl]-pyrrolidin-1-yl}-2-oxo-ethyl)-2-methylaminopropionamide (S)—N—{(S)-2-[(S)-2-(4-Benzoyl-1-methyl-oxazol-2-yl)-pyrrolidin-1-yl]-1-cyclohexyl-2-oxo-ethyl}-2-methylamino-propionamide (S)—N—((S)-1-Cyclohexyl-2-{(S)-2-[4-(4-fluoro-benzoyl)-5-methyl-oxazol-2-yl]-pyrrolidin-1-yl}-2-oxo-ethyl)-2-methylaminopropionamide (S)—N—((S)-1-Cyclohexyl-2-{(S)-2-[4-(4-fluoro-benzoyl)-5-methyl-thiazol-2-yl]-pyrrolidin-1-yl}-2-oxo-ethyl)-2-methylaminopropionamide (S)—N—{S)-2-[(S)-2-(4-Benzoyl-oxazol-2-yl)-pyrrolidin-1-yl]-1-cyclohexyl-2-oxo-ethyl}-2-methylamino-propionamide (S)—N—((S)-1-Cyclohexyl-2-{(S)-2-[4-(2,4-difluoro-benzoyl)-thiazol-2-yl]-pyrrolidin-1-yl}-2-oxo-ethyl)-2-methylamino-propionamide (S)—N—((S)-1-Cyclohexyl-2-{(S)-2-[4-(1H-indole-2-carbonyl)-thiazol-2-yl]-pyrrolidin-1-yl}-2-oxo-ethyl)-2-methylamino-propionamide (S)—N—((S)-1-Cyclohexyl-2-{(S)-2-[2-(4-fluoro-phenoxy)-pyridin-4-yl]-pyrrolidin-1-yl}-2-oxo-ethyl)-2-methylamino-propionamide (S)—N—[(S)-1-((S)-2-{2-[(4-Fluoro-phenyl)-methyl-amino]-pyridin-4-yl}-pyrrolidine-1-carbonyl)-2-methyl-propyl]-2-methylaminopropionamide (S)—N—((S)-1-Cyclohexyl-2-{(S)-2-[2-(4-fluoro-benzoyl)-pyridin-4-yl]-pyrrolidin-1-yl}-2-oxo-ethyl)-2-methylamino-propionamide (S)—N—((S)-1-Cyclohexyl-2-{(S)-2-[2-(5-fluoro-pyridin-2-ylamino)-pyridin-4-yl]-pyrrolidin-1-yl}-2-oxo-ethyl)-2-methylamino-propionamide (S)—N—[(S)-1-Cyclohexyl-2-((S)-2-{3-fluoro-2-[(4-fluoro-phenyl)-methyl-amino]-pyridin-4-yl}-pyrrolidin-1-yl)-2-oxo-ethyl]-2-methylamino-propionamide (S)—N—((S)-1-Cyclohexyl-2-{(S)-2-[3-fluoro-2-(4-fluoro-benzoyl)-pyridin-4-yl]-pyrrolidin-1-yl}-2-oxo-ethyl)-2-methylaminopropionamide (S)—N—[(S)-2-((S)-2-{2-Amino-6-[N-(4-fluoro-phenyl)-hydrazino]-pyridin-4-yl}-pyrrolidin-1-yl)-1-cyclohexyl-2-oxo-ethyl]-2-methylamino-propionamide (S)—N—{(S)-1-Cyclohexyl-2-oxo-2-[(S)-2-(4-phenoxy-pyridin-2-yl)-pyrrolidin-1-yl]-ethyl}-2-methylamino-propionamide (S)—N—((S)-1-Cyclohexyl-2-{(S)-2-[6-(4-fluoro-phenoxy)-2-methyl-pyrimidin-4-yl]-pyrrolidin-1-yl}-2-oxo-ethyl)-2-methylamino-propionamide (S)—N—((S)-1-Cyclohexyl-2-{(S)-2-[4-(4-fluoro-benzoyl)-pyridin-2-yl]-pyrrolidin-1-yl}-2-oxo-ethyl)-2-methylamino-propionamide (S)—N—((S)-1-Cyclohexyl-2-{(S)-2-[6-(4-fluoro-benzoyl)-2-methyl-pyrimidin-4-yl]-pyrrolidin-1-yl}-2-oxo-ethyl)-2-methylamino-propionamide (S)—N—[(S)-1-Cyclohexyl-2-((S)-2-{5-[(4-fluoro-phenyl)-methyl-amino]-pyridin-3-yl}-pyrrolidin-1-yl)-2-oxo-ethyl]-2-methylamino-propionamide (S)—N—[(S)-1-Cyclohexyl-2-((S)-2-{4-[(4-fluoro-phenyl)-methyl-amino]-pyridin-2-yl}-pyrrolidin-1-yl)-2-oxo-ethyl]-2-methylamino-propionamide (S)—N—[(S)-1-Cyclohexyl-2-((S)-2-{6-[(4-fluoro-phenyl)-methyl-amino]-2-methyl-pyrimidin-4-yl}-pyrrolidin-1-yl)-2-oxo-ethyl]-2-methylamino-propionamide (S)—N—((S)-1-{(S)-2-[6-(4-Fluoro-benzoyl)-2-methyl-pyrimidin-4-yl]-pyrrolidine-1-carbonyl}-2-methyl-propyl)-2-methylamino-propionamide (S)—N—((S)-1-{(S)-2-[6-(4-Fluoro-benzoyl-2-methyl-pyrimidin-4-yl]-pyrrolidine-1-carbonyl}-2-methyl-propyl)-2-methylamino-propionamide (S)—N—[(S)-1-((S)-2-{6-[(4-Fluoro-phenyl)-methyl-amino]-2-methyl-pyrimidin-4-yl}-pyrrolidine-1-carbonyl)-2-methyl-propy 1]-2-methylamino-propionamide (S)—N—((S)-1-Cyclohexyl-2-{(S)-2-[6-(4-fluoro-phenylamino)-2-methyl-pyrimidin-4-yl]-pyrrolidin-1-yl}-2-oxo-ethyl)-2-methylamino-propionamide (S)—N—((S)-1-{(S)-2-[6-(4-Fluoro-phenylamino)-2-methyl-pyrimidin-4-yl]-pyrrolidine-1-carbonyl}-2-methyl-propyl)-2-methylaminopropionamide In another embodiment of the above aspects, a higher level of NOL3 mRNA expression relative to said reference level predicts responsiveness of the subject to the anti-cancer agent administered in combination with an IAP inhibitor.

In a further embodiment of the above aspects, a higher level of NOL3 polypeptide expression relative to said reference level additionally predicts responsiveness of the subject to the anti-cancer agent administered in combination with an IAP inhibitor.

In an additional embodiment of the above aspects, a subject having a higher level of NOL3 mRNA expression relative to said reference level is selected for a treatment regimen additionally comprising an IAP inhibitor.

In yet another embodiment of the above aspects, a subject having a higher level of NOL3 mRNA expression relative to said reference level is selected for a treatment regimen additionally comprising an IAP inhibitor.

In another embodiment of the above aspects, the growth-factor receptor inhibitor is imatinib.

BRIEF DESCRIPTION OF THE DRAWINGS

FIG. 1B: depicts a graph showing that LBW242 competes with full-length Smac for occupancy of the XIAP-BIR3 surface groove.

FIG. 1C: depicts a graph showing that LBW242 overcomes XIAP-BIR3-mediated repression of caspase-3 activity in a cell-free extract, resulting in activation of caspase-3 and cleavage of the fluorogenic substrate.

FIG. 1D: depicts an immunoblot showing levels of XIAP and caspase-9 in LN827 cells treated with the indicated concentration of LBW242 after immunoprecipitation of caspase-9.

FIG. 1F depicts densitometric analysis of XIAP in complex with caspase-9 after treatment with the indicated concentration of LBW242 relative to vehicle control.

FIG. 1H: depicts a graph showing the effect of LBW242 as a single agent on the growth of U87 cells.

FIG. 2C: depicts a blot showing the effect of imatinib and LBW242 on the activation state of PDGFR in LN827 cells.

FIG. 4C: depicts an immunoblot showing the effects of LBW242 and imatinib on Akt phosphorylation and BAD phosphorylation, Akt activation was assessed by Ser473 phosphorylation.

FIG. 4E: depicts a Western blot showing the effect of treatment of LN827 cells with imatinib and/or LBW242 for six hours on the phosphorylation of Erk1/2.

FIG. 5A: depicts RT-PCR analysis of NOL3 after treatment with imatinib.

FIG. 5B: depicts a Western blot of NOL3 expression after treatment with imatinib.

FIG. 5C: depicts a graph showing the comparison of NOL3 mRNA expression levels in normal brain tissue, compared with malignant glioma specimens.

FIG. 5F: depicts an immunoblot showing the ectopic expression of NOL3 after transfection of an expression plasmid.

FIG. 5H: depicts a blot showing siRNA knockdown of NOL3 in LN827 cells.

FIG. 6A: depicts images showing tumor burden in mice treated with vehicle, AMN107, LBW212 or AMN107 and LDW242.

FIG. 6D: depicts images showing human glioblastoma neurospheres treated with LBW242 and/or imatinib.

FIG. 6E: depicts an immunoblot showing caspase-3 activation in tumor neurospheres treated for 72 hours with imatinib, AMN107(AMN), and/or LBW242(LBW)

FIG. 6F: depicts a graph showing the percent survival for mice implanted with primary human glioma orthografts and treated with AMN107, LBW242, or a combination of AMN107 and LBW242.

FIG. 7: depicts a graph showing the effect of NOL3 expression on patient survival in combination with the expression levels of the IAP survivin.

FIG. 8A: depicts graphs showing that NOL3 levels do not impart a significant difference in survival when high-grade gliomas are stratified by histological grade.

FIG. 8B: depicts graphs showing that survivin levels do not impart a significant difference in survival when high-grade gliomas are stratified by histological grade.

DETAILED DESCRIPTION OF THE INVENTION

Figure 1A:
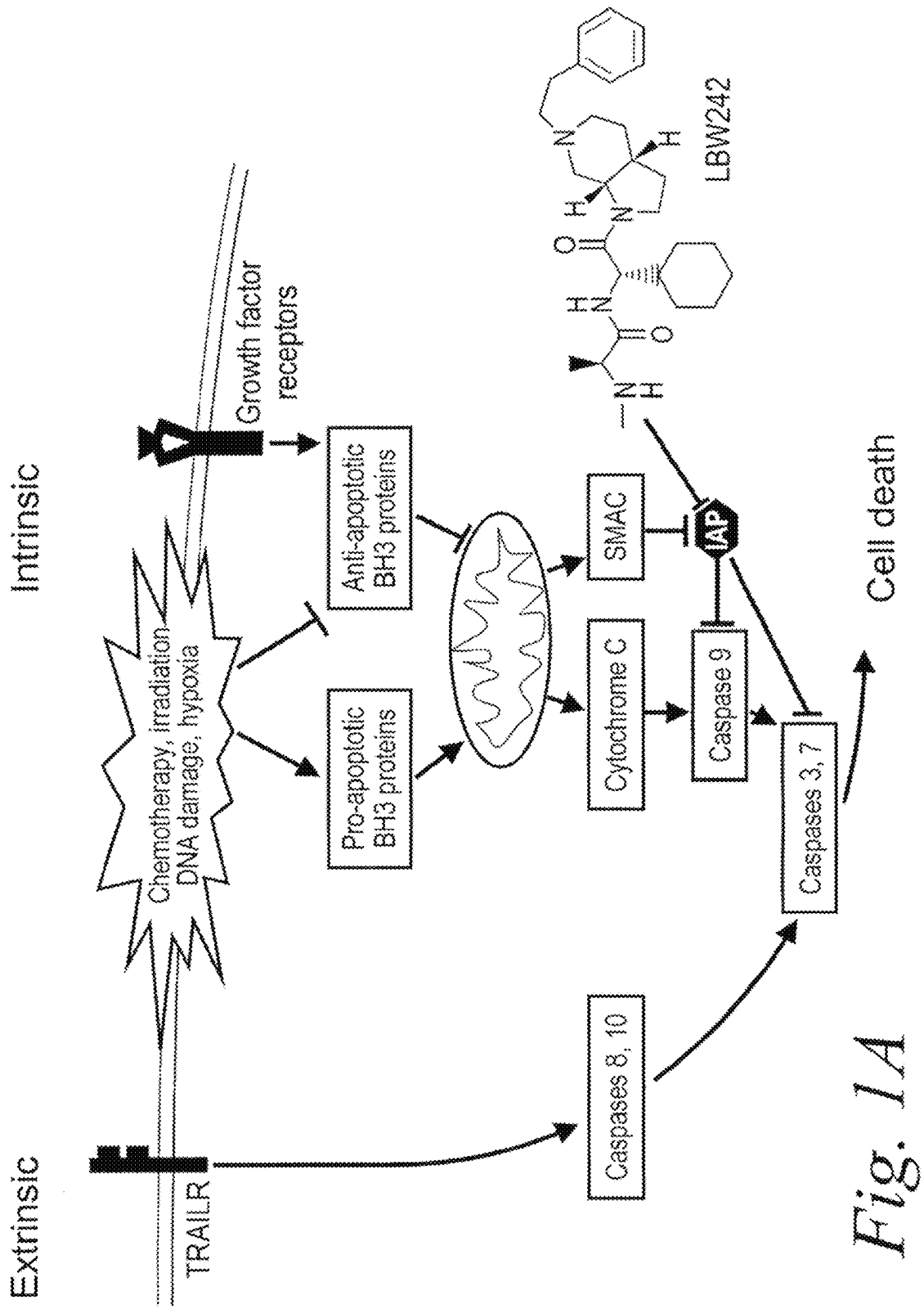
FIG. 1A: depicts the mechanism by which PDGFR and IAP inhibition synergistically results in cell death.

The present invention provides methods for determining the prognosis for survival of a cancer patient. In addition, the present invention demonstrates that anti-apoptotic proteins may be important biomakers predictive of response to treatment with anti-cancer agents, such as receptor tyrosine kinase (RTK) inhibitors, and that targeting the apoptotic pathway, in conjunction with RTK inhibition, has the potential to further improve tumor response.

The invention is based, at least in part, on the observation that the anti-apoptotic protein NOL3 is highly expressed in malignant gliomas and correlates with poor survival. In particular, RTK inhibition activates the apoptotic cascade by decreasing the expression of NOL3, but does not result in downstream caspase activation. Small molecule blockade of the Inhibitor of Apoptosis Proteins (IAP) in combination with RTK inhibition results in caspase activation and apoptosis, and has synergistic anti-tumor efficacy in vitro and in vivo in orthotopic glioma models.

In order that the present invention may be more readily understood, certain terms are first defined. Additional terms are set forth throughout the detailed description.

The term "detectable probe" includes any molecule that specifically binds to a nucleic acid sequence or to a protein that is being selected for, and which can be labeled so that the required targets can be detected. For example, the probe may be radiolabeled or chemically tagged. In another example, specific monoclonal antibodies may be used to detect proteins, and said monoclonal antibody can be labeled so that the protein of interest can be detected.

The term "favorable outcome" is intended to refer to an affirmative outcome. For example, a favorable outcome may refer to overall survival or progression-free survival. More preferably, a favorable outcome may refer to disease-free survival.

The term "cancer" is intended to refer to cells or tissue containing cells that have become malignantly transformed so that they exhibit uncontrolled growth and invasive properties. Depending on the cell type involved, the cancerous cells may form a solid tumor (carcinoma, sarcoma) or may cause various types of hematologic malignancies.

The term "tumor grade" is intended to refer to the degree of abnormality of cancer cells. In one aspect, tumor grade is a measure of differentiation. In another aspect, tumor grade is the extent to which cancer cells are similar in appearance and function to healthy cells of the same tissue type. Tumor grade may be described by four degrees of severity (i.e., grades 1, 2, 3, and 4) based on the microscopic appearance of cancer cells. For example, the cells of Grade 1 tumors are often well-differentiated or low-grade tumors, and are generally considered the least aggressive in behavior. Conversely, the cells of Grade 3 or Grade 4 tumors are usually poorly differentiated or undifferentiated high-grade tumors, and are generally the most aggressive in behavior.

Furthermore, the grading system used to assess a tumor may be different for each type of cancer. In general, tumor grade is a system used to classify cancer cells in terms of how abnormal they look under a microscope and how quickly the tumor is likely to grow and spread. Tumor grade may be determined by many factors, including the structure and growth pattern of the cells. Accordingly, the specific factors used to determine tumor grade may vary with each type of cancer.

The term "tumor stage" or "cancer stage" is intended to refer to the extent or severity of the cancer, based on factors such as the location of the primary tumor, tumor size, number of tumors, and lymph node involvement (spread of cancer into lymph nodes).

The term "cancer cell-containing sample" includes a sample of cells, tissue, or fluid taken from the diseased area of a subject with cancer. The cancer cell-containing sample may also include cancer cells or cell lines kept in culture. The cancer cell-containing sample may also include a fluid, e.g., saline, that is introduced into the subject, and then removed from the subject for analysis. The cancer cell-containing sample may further include tumor cells isolated from blood peripheral to the diseased area.

The term "normal tissue sample" includes a sample of cells, tissue, or fluid taken from a disease-free subject or from a disease-free area of a subject with cancer or a disease-free area of the cancer containing tissue of a subject with cancer. The normal tissue sample may also include normal cells kept in culture. Furthermore, the normal tissue sample may also include a fluid that was introduced into the subject, e.g., saline, and then removed from the subject for analysis.

The term "reference sample" includes a sample corresponding to normal tissue or cells take from the same individual or a different individual. For example, the reference sample may be taken from a disease-free area of the cancer containing tissue in the subject of interest or the reference sample may be taken from disease-free tissue of the subject of interest that does not correspond to the diseased-tissue. In another example, the reference sample may be taken from the tissue of a disease-free subject, either from tissue that corresponds to the diseased-tissue of the subject of interest or other normal tissue of the disease-free subject.

The term "reference level" refers to a control level of expression of a nucleotide sequence or polypeptide used to evaluate a test level of expression of a nucleotide sequence or polypeptide in a cancer cell-containing sample of a patient. For example, when the level of NOL3 in the cancer cell-containing sample of a patient is higher than the reference level of NOL3, the cells will be considered to have a high level of expression, or overproduction, of NOL3. Conversely, when the level of NOL3 in the cancer cell-containing sample of a patient are equivalent or lower than the reference level, the cells will be considered to have a normal or low level of expression of NOL3. In one aspect, the reference level may be determined by assaying the level of expression of the nucleotide sequence or polypeptide of interest in the reference sample.

The term "NOL3" refers to nucleolar protein 3 (apoptosis repressor with CARD domain). The term "NOL3" includes ARC, MYC, MYP, NOP, and NOP30. Preferably, the term "NOL3" refers to NOL3 mRNA. The term "ARC" refers to apoptosis repressor with CARD domain, the term ARC may also refer to nucleolar protein 3 (apoptosis repressor with CARD domain).

The term "NOL3" refers to NOL3 and/or ARC. Preferably, the term "NOL3" refers to NOL3 mRNA and/or NOL3 polypeptide.

The term "level of NOL3 mRNA" refers to the expression level of NOL3 mRNA in the sample of interest. In one aspect, the level of NOL3 mRNA may be assayed by a technique selected from the group including Northern blot, RT-PCT, Quantitative PCR (QPCR), non-PCR amplification methods (e.g., strand displacement amplification (SDA), rolling-circle amplification (RCA), multiple-displacement amplification (MDA), transcription meditated amplification (TMA), and nucleic acid sequence based amplification (NASBA)), Luminex bead analysis, in situ hybridization, and gene expression microarray analysis.

The term "slight increase in NOL3 mRNA" refers to a slight increase in the expression level of mRNA in a sample of interest when compared to a reference sample. For example, the slight increase in NOL3 mRNA may correspond to the difference in NOL3 mRNA expression levels between a reference sample and the expression level observed in a sample from a grade III tumor.

The term "moderate increase in NOL3 mRNA" refers to a moderate increase in the expression level of mRNA in a sample of interest when compared to a reference sample. For example, a moderate increase in NOL3 mRNA may correspond to the difference in NOL3 mRNA expression levels between a reference sample and the expression level observed in a sample from a grade IV tumor.

The term "large increase in NOL3 mRNA" refers to a large increase in the expression level of mRNA in a sample of interest when compared to a reference sample. For example, a large increase in NOL3 mRNA may correspond to the difference in NOL3 mRNA expression levels between a reference sample and the expression level observed in a recurrent tumor.

The term "level of NOL3 polypeptide" refers to the expression level of NOL3 polypeptide in the sample of interest. In one aspect, the level of NOL3 polypeptide may be assayed by a technique selected from the group including western blot, immunohistochemistry, indirect immunofluorescence, direct immunofluorescence, intracellular flow cytometry, enzyme-linked immunosorbent assay (ELISA), and antibody microarray analysis.

The term "slight increase in NOL3 polypeptide" refers to a slight increase in the polypeptide expression level in a sample of interest when compared to a reference sample. For example, the slight increase in NOL3 polypeptide may correspond to the difference in NOL3 polypeptide expression levels between a reference sample and the expression level observed in a sample from a grade III tumor.

The term "moderate increase in NOL3 polypeptide" refers to a moderate increase in the polypeptide expression level in a sample of interest when compared to a reference sample. For example, a moderate increase in NOL3 polypeptide may correspond to the difference in NOL3 polypeptide expression levels between a reference sample and the expression level observed in a sample from a grade IV tumor.

The term "large increase in NOL3 polypeptide" refers to a large increase in the polypeptide expression level in a sample of interest when compared to a reference sample. For example, a large increase in NOL3 polypeptide may correspond to the difference in NOL3 polypeptide expression levels between a reference sample and the expression level observed in a recurrent tumor.

The term "level of survivin" refers to the expression level of survivin mRNA or polypeptide. In one aspect, the level of survivin mRNA may be assayed by a technique selected from the group including Northern blot, RT-PCR, Quantitative PCR (QPCR), in situ hybridization, and gene expression microarray analysis. In another aspect, the level of survivin polypeptide may be assayed by a technique selected from the group including western blot, immunohistochemistry, indirect immunofluorescence, direct immunofluorescence, intracellular flow cytometry, enzyme-linked immunosorbent assay (ELISA), and antibody microarray analysis.

The term "higher level of NOL3" refers to an increase in the expression level of NOL3 polypeptide in the sample of interest when compared to a reference sample.

The term "survival", refers to the act or fact of living. The term "disease-free survival" is intended to refer to the lack of tumor recurrence and/or spread and the fate of a patient after diagnosis, for example, a patient who is alive without tumor recurrence. The phrase "overall survival" refers to the fate of the patient after diagnosis, regardless of whether the patient has a recurrence of the tumor.

The term "IAP inhibitor" refers to any compound that inhibits the activity of a member of the IAP family of proteins. Such compounds may include, for example, small molecules, polypeptides (i.e., Smac mimetic peptides), RNA interference molecules targeting IAP proteins (e.g., siRNA, shRNA, miRNA or antisense RNA), anti-IAP antibodies and agents that inhibits IAPs. Preferably, the IAP inhibitor is LBW-242. In another preferred embodiment, the IAP inhibitors that can be used in the instant invention, and methods of making them, are disclosed in WO 2005/097791 and WO 2008/016893, both herein incorporated by reference in their entirety.

The term "anti-cancer agent" includes compounds which inhibit or suppress the growth of cancer cells. An anti-cancer agent may also include compounds that destroy cancer cells or interfere with cell division, monoclonal antibodies that bind proteins on the cell surface, peptides that bind cell surface receptors, interferons or cytokines which induce an immune response, vaccines which generate an immune response, hormones or compounds that block certain hormones involved in cancer, compounds that inhibit or prevent the growth of new blood vessels, (i.e., angiogenesis inhibitors), agents that damage DNA (e.g., alkylating agents, for example, cisplatin, carboplatin, and oxaloplatin; anti-metabolites; and topoisomerase inhibitors), and compounds with anti-cancer properties (e.g., taxanes, vinca alkaloids, and plant alkaloids). The term "anti-cancer agent" also includes radiation therapy. An anti-cancer agent may also include an agent specific for deregulated proteins of cancer cells, such as an inhibitor of receptor tyrosine kinases, preferably imatinib.

The term "subject" includes humans, and non-human animals amenable to therapy, e.g., preferably mammals and animals susceptible to cancer, such as non-human primates, transgenic animals, dogs, cats, horses, and cows. The term "subject" also includes patients, more preferably cancer patients. The term "cancer patient" includes humans, and non-human animals that have cancer.

The term "prognosis" is intended to denote the prediction of how a patients disease will progress, whether there is a chance for recovery and how a patient may respond to treatment.

The term "responsiveness" refers to a positive reaction by a subject undergoing treatment with an anti-cancer agent, an IAP inhibitor or an anti-cancer agent and an IAP inhibitor. The term "positive reaction" includes any response that is not negative.

The term "predicting responsiveness" refers to the ability to foretell or infer whether a subject will respond in a positive manner, (e.g., whether a patient will be responsive) or a negative manner.

The term "treatment" refers to a process, manner or regimen which allows for medicinal or surgical care for an illness or injury in a subject. In certain embodiments, the treatment comprises diminishing or alleviating at least one symptom directly or indirectly associated with or caused by cancer. For example, treatment can be diminishment of one or several symptoms of cancer or complete eradication of cancer.

The term "treatment regimen" refers to a regulated course of treatment intended to preserve or restore health, or to attain some result, e.g., inhibit or suppress tumor growth. In one embodiment the treatment regimen may include administering an anti-cancer agent to a cancer patient, preferably, imatinib. In another embodiment, the treatment regimen may include administering an IAP inhibitor to a cancer patient, preferably LBW-242. In a further embodiment, the treatment regimen may include administering an anti-cancer agent and an IAP inhibitor to a cancer patient, preferably imatinib and LBW-242.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and are not intended to be limiting.

Various aspects of the invention are described in further detail in the following subsections.

Prediction of Responsiveness to Therapy for Cancer

In one aspect, the invention pertains to a method for predicting the prognosis for survival of a cancer patient. Typically, the method comprises assaying the level of NOL3/NOL3 in a cancer cell-containing sample from a cancer patient and comparing the level of NOL3 to a reference level, and predicting the prognosis for survival of the patient based on the levels of NOL3.

A variety of growth factor receptors are instrumental in the tumorigenesis of gliomas and have been validated as therapeutic targets. Malignant gliomas often exhibit overexpression of both platelet derived growth factor (PDGF) and platelet derived growth factor receptor (PDGFR), which contribute to tumor progression via an autocrine or paracrine loop (Fleming et al., *Cancer Res.* 52, 4550-4553, 1992; Guha et al., *Int. J. Cancer* 60, 168-173, 1995; Hermanson et al., *Cancer Res.* 52, 3213-3219, 1992.). Antagonism of PDGFR with the tyrosine kinase inhibitor imatinib (STI571, Gleevec) in both in vitro and in vivo glioma models has demonstrated successful inhibition of tumor growth (Kilic et al., *Cancer Res.* 60, 5143-5150, 2000.).

In addition, the Inhibitor of Apoptosis Proteins (IAPs) have been shown to be highly expressed in malignant gliomas. The IAPB represent the final molecular blockade preventing apoptosis by inhibiting the activity of caspases 3, 7 and 9. The IAP survivin has been identified in the majority of gliomas where its levels correlated inversely with prognosis.

A variety of anti-apoptotic mechanisms render glioma cells chemo- and radio-resistant, and it has been hypothesized that these anti-apoptotic mechanisms likewise confer resistance to RTK inhibition. The anti-apoptotic protein NOL3 was found to be highly expressed in malignant gliomas and its expression correlates with poor survival. It has been demonstrated that RTK inhibition activates the apoptotic cascade by decreasing the expression of NOL3, but does not result in downstream caspase activation. Small molecule blockade of the IAPs in combination with RTK inhibition results in caspase activation and apoptosis, and has synergistic anti-tumor efficacy in vitro and in vivo in orthotopic glioma models.

In one aspect, the method of the present invention relates to determining the prognosis for survival of a cancer patient. In one embodiment, the method includes measuring a level of NOL3 expression in a cancer cell-containing sample from a cancer patient and comparing the level of NOL3 expression in the sample to a reference level of NOL3. For example, a higher level of NOL3 in the sample relative to the reference level correlates with decreased survival of the patient, and an equivalent or lower level of NOL3 relative to the reference sample correlates with increased survival of the patient.

In another aspect, the method of the present invention relates to determining the prognosis for survival of a cancer patient by measuring the level of NOL3 and measuring the level of survivin in a cancer cell-containing sample from the patient. Furthermore, the method includes comparing the level of NOL3 and survivin expression to a reference level of NOL3 expression and a reference level of survivin expression. For example, a higher level of NOL3 and a higher level of survivin relative to the reference level correlates with decreased survival of the patient, and an equivalent or lower level of NOL3 and an equivalent or lower level of survivin relative to the reference level correlates with increased survival.

In one aspect, the method of the present invention provides a method of predicting responsiveness to an anticancer agent in a subject having cancer, wherein the cancer agent reduces the expression of NOL3, the method comprising: measuring the level of NOL3 expression in a cancer cell-containing sample from the subject and comparing the level of NOL3 in the sample to a reference level of NOL3. For example, a higher level of NOL3 expression relative to the reference level predicts responsiveness of the patient to the anti-cancer agent. Also, for example, a higher level of NOL3 expression relative to the reference level predicts responsiveness of the subject to the anti-cancer agent administered in combination with an IAP inhibitor.

In another aspect, the method of the present invention includes predicting the responsiveness of a subject having cancer to an IAP inhibitor by measuring the expression level of NOL3 in a cancer cell-containing sample and comparing the level of NOL3 in the sample to a reference level of NOL3. In one embodiment, an equivalent or lower level of NOL3 expression relative to the reference sample predicts responsiveness of the subject to an IAP inhibitor.

In a one aspect, the present invention provides a method for selecting a subject having cancer for a treatment regimen by the method comprising: measuring the level of NOL3 in a cancer cell containing sample from the subject, comparing the level of NOL3 expression in the sample to the reference level of NOL3 and selecting subjects having elevated NOL3 expression for a treatment regimen including a NOL3 inhibitor. Preferably, the subjects having elevated NOL3 expression are selected for a treatment regimen comprising an agent that reduces NOL3 activity and an IAP inhibitor. In one embodiment, the selected subject has an equivalent or lower level of NOL3 expression relative to the reference sample and is selected for a treatment regimen comprising an IAP inhibitor.

In one aspect, the method of the present invention provides a means for diagnosing the grade or stage of a tumor in a subject having cancer. In one embodiment the method includes measuring the level of NOL3 expression in a cancer cell-containing sample from the subject and comparing the level of NOL3 in the sample to a reference level. For example, a higher level of NOL3 relative to the reference sample correlates with worsening tumor grade.

The methods of the present invention may be used to predict prognosis for survival of a patient having any cancer. Examples of cancers that are embodied by the present invention, include but are not limited to breast, brain, ovarian, colorectal, gastric, prostate, testicular, uterine, cervical, pancreatic, skin, colon, stomach, esophagus, bladder, lung, and small cell lung cancer. In one embodiment, the subject suffers from a glioma; for example, an astrocytoma, ependymoma, oligodendroglioma, mixed glioma, and glioblastoma multiforme. In another embodiment, the subject suffers from a carcinoma; for example, ovarian carcinoma, colorectal carcinoma, and small cell lung carcinoma. In another embodiment, the subject suffers from a hematologic malignancy; for example, acute leukemia, chronic leukemia, multiple myeloma, or lymphoma.

In a further embodiment the subject suffers from a sarcoma; for example, osteosarcoma, chondrosarcoma, leiomyosarcoma, gastrointestinal stromal tumor (GIST), Ewing's sarcoma, Askin's tumor, malignant hemangioendothelioma, malignant schwannoma, and soft tissue sarcoma (e.g., alveolar soft part sarcoma, angiosarcoma, cystosarcoma phylloides, dermatofibrosarcoma, desmoid tumor, desmoplastic small round cell tumor, epithelioid sarcoma, extraskeletal chondrosarcoma, extraskeletal osteosarcoma, fibrosarcoma, hemangiopericytoma, hemangiosarcoma, Kaposi's sarcoma, liposarcoma, lymphangiosarcoma, lymphosarcoma, malignant fibrous histiocytoma, neurofibrosarcoma, rhabdomyosarcoma, and synovial sarcoma).

In the method of the invention for predicting the prognosis for survival of a cancer patient, the level of expression of NOL3 (e.g., NOL3 mRNA) can be assayed in the subject using techniques well established in the art. In a preferred embodiment, the expression level of NOL3 mRNA in the subject is assayed by obtaining a cancer cell-containing sample from the subject and detecting the level of NOL3 mRNA. Additionally or alternatively, the level of expression of NOL3 polypeptide can be assayed in the subject using techniques well established in the art. Preferably, the expression level of NOL3 polypeptide in the subject is assayed by obtaining a cancer cell-containing sample from the subject and detecting the level of NOL3 polypeptide. Furthermore, the expression level of NOL3 mRNA and/or NOL3 polypeptide can be assayed in a reference sample using techniques well established in the art. Preferably, the expression level of NOL3 mRNA and/or NOL3 polypeptide is assayed by obtaining a disease free reference sample from the subject of interest or a disease free subject and detecting the level of NOL3 mRNA and/or NOL3 polypeptide in the sample.

For example, an assay for detecting the levels of mRNA in a sample may be selected from the group including Northern blot, RT-PCR, Quantitative PCR (QPCR), in situ hybridization, and gene expression microarray analysis. In an exemplary embodiment of these aspects, a nucleotide probe that hybridizes to NOL3 mRNA can be used to detect NOL3 mRNA. In another embodiment of these aspects, a nucleotide probe which hybridizes to survivin mRNA may be used to detect survivin mRNA. Also for example, an assay for detecting the levels of a polypeptide in a sample may be selected from the group including Western blot, immunohistochemistry, indirect immunofluoresence, enzyme-linked immunosorbent assay (ELISA), and antibody microarray analysis. In an exemplary embodiment of these aspects, an antibody that binds NOL3 polypeptide may be used to detect NOL3 polypeptide. In another embodiment of these aspects, an antibody that binds survivin polypeptide may be used to detect survivin polypeptide.

The specific examples described above for detecting the expression levels of mRNA and/or a polypeptide are representative examples and are not intended to be limiting. Other suitable approaches for assaying the expression level of mRNA and/or a polypeptide are known in the art. It will be readily understood by the ordinarily skilled artisan that essentially any technical means established in the art for detecting mRNA and/or polypeptide levels in a sample can be adapted to the detection of NOL3 and/or survivin as discussed herein and applied in the methods of the current invention for predicting patient outcome.

Selection and Use of a Compound with Anti-Cancer Properties

Given the observation that the increase in NOL3 in cancer patients influences the responsiveness of the subject to therapy, one can select an appropriate compound with anti-cancer properties for the treatment of a subject based on the level of NOL3 in the subject. Accordingly, in one aspect, the above-described method for predicting prognosis for survival of a cancer patient further comprises selecting a compound with anti-cancer properties.

A compound with anti-cancer properties may include compounds that inhibit or suppress the growth of cancer cells. A compound with anti-cancer properties can also include an anti-cancer agent, compounds that destroy cancer cells or interfere with cell division, monoclonal antibodies that bind proteins on the cell surface, peptides that bind cell surface receptors, interferons or cytokines which induce an immune response, vaccines which generate an immune response, hormones or compounds that block certain hormones involved in cancer, compounds that inhibit or prevent the growth of new blood vessels, i.e., angiogenesis inhibitors. A compound with anti-cancer properties may also include an agent specific for deregulated proteins of cancer cells, such as an inhibitor of receptor tyrosine kinases, preferably imatinib.

In one aspect, the method of the present invention includes identifying a compound as an anti-cancer agent. For example, a cell line expressing NOL3 is treated with a compound and the change in NOL3 expression is determined, and a compound that reduces the level of NOL3 expression is identified as an anti-cancer agent. Preferably, the method of the present invention relates to the treatment of cancer by administering the identified compound of this aspect alone or in combination with an IAP inhibitor.

The present invention provides methods for identifying a compound as an anti-cancer agent. In one aspect, such a method includes treating a cell line expressing NOL3 with a compound; assaying for a change in NOL3 expression after treatment with the compound; and identifying a compound that reduces the level of NOL3 as an anti-cancer agent.

In one embodiment, the present invention pertains to methods of treating a subject with cancer. For example, the subject may be treated with the anti-cancer agent identified by the method of the instant application. Alternatively or additionally, the subject may be treated with other anti-cancer agents, i.e., biologic agents and/or other therapeutic anti-cancer agents, such as traditional chemotherapeutic agents, radiotherapeutic agents and/or inhibitors of receptor tyrosine kinases.

Preferably, the methods of the present invention pertain to the treatment of a cancer patient with an inhibitor of receptor tyrosine kinases. In one embodiment, treatment with an inhibitor of receptor tyrosine kinases results in the antagonism of epidermal growth factor receptor (EGFR), EGFRvIII, and/or insulin-like growth factor-1 receptor (IGF1R). In a preferred embodiment, treatment with an inhibitor of receptor tyrosine kinases results in the antagonism of platelet derived growth factor receptor (PDGFR).

In a preferred embodiment, the receptor tyrosine kinase inhibitor is selected from the group including imatinib, AMN107, AEW541 and PKI166.

In another embodiment, the present invention pertains to the treatment of a cancer patient with an anti-cancer agent and an agent that inhibits the inhibitor of apoptosis proteins (IAPs). In a preferred embodiment the inhibitor of IAPs is LBW242.

In another preferred embodiment, the present invention relates to the treatment of neoplasms, comprising the combination of a growth factor receptor inhibitor and an inhibitor of IAPs disclosed in WO 2008/109057, incorporated herein by reference in its entirety.

Preferably, the present invention pertains to the treatment of a cancer patient with an inhibitor of receptor tyrosine kinases in combination with an inhibitor of IAPs. More preferably, the present invention pertains to the treatment of a cancer patient with AMN107 and LBW242. Most preferably, the present invention pertains to the treatment of a cancer patient with imatinib and LBW242.

In one embodiment, the inhibitor of receptor tyrosine kinases is administered in doses that range from 0.1 µM to greater than or equal to 100 µM. For example, the dose may be 0.1 µM, 0.5 µM, 1.0 µM, 1.5 µM, 2.0 µM, 2.5 µM, 3.0 µM, 3.5 µM, 4.0 µM, 4.5 µM, 5.0 µM, 10.0 µM, 15.0 µM, 20.0 µM, 25.0 µM, 30.0 µM, 40.0 µM, 50.0 µM, 60.0 µM, 70.0 µM, 80.0 µM, 90.0 µM to greater than about 100.0 µM or any incremental value thereof. It is to be understood that all values and ranges between these values and ranges are meant to be encompassed by the present invention. In some embodiments the inhibitor of receptor tyrosine kinases is administered at a dose of 2.5 µM. In other embodiments, the inhibitor of receptor tyrosine kinases is administered at a dose of 10 µM. In still other embodiments, the inhibitor of receptor tyrosine kinases is administered at a dose of greater than about 20.0 µM.

In an exemplary embodiment, the inhibitor of receptor tyrosine kinases is selected from the group including AMN107, AEW541 and PKI166. In a preferred exemplary embodiment, the inhibitor of receptor tyrosine kinases is imatinib.

In one embodiment, the inhibitor of IAPs is administered in doses that range from 1.0 µM to greater than or equal to 500 µM. For example, the dose may be 1.0 µM, 5.0 µM, 10.0 µM, 15.0 µM, 20.0 µM, 25.0 µM, 30.0 µM, 35.0 µM, 40.0 µM, 45.0 µM, 50.0 µM, 60.0 µM, 70.0 µM, 80.0 µM, 90.0 µM, 100.0 µM, 150.0 µM, 200.0 µM, 250.0 µM, 300.0 µM, 350.0 µM, 400.0 µM, 450.0 µM, to greater than about 500.0 µM or any incremental value thereof. It is to be understood that all values and ranges between these values and ranges are meant to be encompassed by the present invention. In some embodiments the inhibitor of IAPs is administered at a dose of 50.0 µM. In other embodiments, the inhibitor of IAPs is administered at a dose of 60.0 µM. In still other embodiments, the inhibitor of IAPs is administered at a dose of greater than about 100.0 µM.

In a preferred exemplary embodiment, the inhibitor of IAPs is LBW242.

In another embodiment, the compounds discussed herein, i.e., inhibitors of receptor tyrosine kinases and inhibitors of IAPs, are administered at a concentration in the range from about 1 mg/kg to greater than about 500 mg/kg. For example, the concentration may be 1.0 mg/kg, 5.0 mg/kg, 10.0 mg/kg, 15.0 mg/kg, 20.0 mg/kg, 25.0 mg/kg, 30.0 mg/kg, 35.0 mg/kg, 40.0 mg/kg, 45.0 mg/kg, 50.0 mg/kg, 60.0 mg/kg, 70.0 mg/kg, 80.0 mg/kg, 90.0 mg/kg, 100.0 mg/kg, 150.0 mg/kg, 200.0 mg/kg, 250.0 mg/kg, 300.0 mg/kg, 350.0 mg/kg, 400.0 mg/kg, 450.0 mg/kg, to greater than about 500.0 mg/kg or any incremental value thereof. It is to be understood that all values and ranges between these values and ranges are meant to be encompassed by the present invention. In some embodiments the inhibitor of IAPs is administered at a concentration of 50.0 mg/kg. In other embodiments, the inhibitor of IAPs is administered at a concentration of 100.0 mg/kg. In still other embodiments, the inhibitor of IAPs is administered at a concentration of greater than about 500.0 mg/kg.

In a preferred exemplary embodiment, the inhibitor of IAPs is LBW242.

In an exemplary embodiment, the inhibitor of receptor tyrosine kinases is selected from the group including AMN107, AEW541 and PKI166. In a preferred exemplary embodiment, the inhibitor of receptor tyrosine kinases is imatinib.

For administration to a subject, a therapeutic agent typically is formulated into a pharmaceutical composition containing the therapeutic agent and a pharmaceutically acceptable carrier. Therapeutic compositions typically must be sterile and stable under the conditions of manufacture and storage. Pharmaceutical compositions also can be administered in combination therapy, i.e., combined with other agents, such as other biologic agents and/or other therapeutic agents, such as traditional chemotherapeutic agents, radiotherapeutic agents and/or inhibitors of receptor tyrosine kinases for the treatment of cancer.

The term, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound may be coated in a material to protect the compound from the action of acids and other natural conditions that may inactivate the compound.

The pharmaceutical compositions may include one or more pharmaceutically acceptable salts. A "pharmaceutically acceptable salt" refers to a salt that retains the desired biological activity of the parent compound and does not impart any undesired toxicological effects (see e.g., Berge, S. M., et al. (1977) *J. Pharm. Sci.* 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and nonaqueous carriers that may be employed in the pharmaceutical compositions include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

A therapeutic agent of the present invention can be administered via one or more routes of administration using one or more of a variety of methods known in the art. As will be appreciated by the skilled artisan, the route and/or mode of administration will vary depending upon the desired results. A preferred route of administration, particularly for therapeutic agents, is by intravenous injection or infusion. Other preferred routes of administration include intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Alternatively, a therapeutic agent of the invention can be administered via a non-parenteral route, such as a topical, epidermal or mucosal route of administration, for example, intranasally, orally, vaginally, rectally, sublingually or topically.

In a preferred embodiment, the subject to be treated with the anti-cancer agent is a human subject, more preferably a human subject that suffers from cancer. Examples of cancers that are embodied by the present invention, include but are not limited to breast, brain, ovarian, colorectal, gastric, prostate, testicular, uterine, cervical, pancreatic, skin, colon, stomach, esophagus, bladder, lung, and small cell lung cancer. In one embodiment, the subject suffers from a glioma; for example, an astrocytoma, ependymoma, oligodendroglioma, mixed glioma, and glioblastoma multiforme. In another embodiment, the subject suffers from a carcinoma; for example, ovarian carcinoma, colorectal carcinoma, and small cell lung carcinoma. In another embodiment, the subject suffers from a hematologic malignancy; for example, acute leukemia, chronic leukemia, multiple myeloma, or lymphoma.

Kits of the Invention

In another aspect, the present invention pertains to kits for carrying out the methods of the invention. For example, in one embodiment, the invention provides a kit for predicting responsiveness to an anti-cancer agent in a subject having cancer, wherein the anti-cancer agent reduces the expression or activity of NOL3. In one embodiment, the kit includes:

a) means for detecting the level of NOL3 expression in a cancer cell containing sample; and b) instructions for use of the kit to predict responsiveness to an anti-cancer agent in a subject having cancer.

In a preferred embodiment, the kit of the present invention further includes an anti-cancer agent. In another preferred embodiment, the kit of the present invention may further comprise an IAP inhibitor.

In one embodiment, the present invention provides a kit for predicting the responsiveness of a subject having cancer to an IAP inhibitor, the kit includes:

a) means for detecting the level of NOL3 expression in a cancer cell containing sample from the subject; and b) instructions for use of the kit to predict responsiveness to an IAP inhibitor in a subject having cancer.

In a preferred embodiment, the kit of the present invention further includes an IAP inhibitor. In another preferred embodiment, the kit of the present invention may further comprise an anti-cancer agent.

In an exemplary embodiment, the means for detecting the expression level of target mRNA in a subject having cancer may include a nucleic acid preparation. This nucleic acid preparation includes at least one, and may include more than one nucleic acid probe or primer, the sequence of which is designated such that the nucleic acid preparation hybridizes to the mRNA of interest. A preferred nucleic acid preparation includes at least one labeled probe so that the target mRNA can be detected. A more preferred nucleic acid preparation includes two or more primers that allow for amplification of the target mRNA. For example, suitable probes and primers comprise a sequence which hybridizes to NOL3 mRNA. Also for example, suitable probes and primers comprise a sequence which hybridizes to survivin mRNA.

Furthermore, the means for detecting the expression level of a target polypeptide in a subject having cancer comprises a reagent that detects a gene product in a cancer cell containing sample from the subject of interest and/or a reference sample. A non-limiting example of such a reagent is a monoclonal antibody specific for NOL3. Another non-limiting example of such a reagent is a monoclonal antibody specific for survivin.

The means for assaying the presence of NOL3 or survivin can also include, for example, buffers or other reagents for use in an assay for evaluating the expression level of NOL3 or survivin. The instructions can be, for example, printed instructions for performing the assay for evaluating the expression level of NOL3 or survivin.

In another example, the kit can further comprise an anti-cancer agent for treating cancer in a subject.

In a preferred embodiment, the kit includes means for detecting the expression level of NOL3 in a subject as a predictor for responsiveness to an anti-cancer agent. In this embodiment, the instructions can instruct the end user of the kit that the presence of an increased level of NOL3 relative to the reference level predicts responsiveness of the subject to the anti-cancer agent. Also in this embodiment, the instructions can instruct the end user of the kit that the presence of an increased level of NOL3 relative to the reference level predicts responsiveness of the subject to the anti-cancer agent administered in combination with an IAP inhibitor.

In another preferred embodiment, the kit includes means for detecting the level of NOL3 in a subject as a predictor for responsiveness to an IAP inhibitor. In this embodiment, the instructions can instruct the end user of the kit that an equivalent or lower level of NOL3 relative to the reference level predicts responsiveness of the subject to an IAP inhibitor.

In another embodiment, the kit includes means for detecting the expression level of NOL3 in a subject as a means for determining the prognosis for survival of a cancer patient. In this embodiment, the instructions can instruct the end user of the kit that the presence of an increased level of NOL3 relative to the reference level correlates with decreased survival of the patient. Additionally or alternatively, the instructions can instruct the end user of the kit that equivalent or lower levels of NOL3 relative to the reference level correlate with increased survival of the patient.

Additionally, the kit may include means for detecting the expression level of survivin in a subject as a means for determining the prognosis for survival of a cancer patient. In this embodiment, the instructions can instruct the end user of the kit that the presence of an increased level of survivin relative to the reference sample correlates with decreased survival of the patient. Additionally or alternatively, the instructions can instruct the end use of the kit that equivalent or lower levels of survivin relative to the reference levels correlates with increased survival of the patient.

In another aspect, the kit of the present invention includes means for diagnosing the grade or stage of a tumor in a subject. In this aspect, the instructions can instruct the end user of the kit that an increased level of NOL3 relative to the reference level correlates with worsening grade or stage of the tumor. For example, a slight increase in NOL3 correlates with a grade III tumor, a moderate increase in NOL3 correlates with a grade IV tumor, and a large increase in NOL3 correlates with a recurrent tumor.

In a another aspect, the kit of the present invention includes means for selecting a subject having cancer for a treatment regimen. In this aspect, the instructions can instruct the end user of the kit that a subject having a higher level of NOL3 relative to the reference level is selected for a treatment regime comprising an agent that reduces the expression or activity of NOL3. Also, the instructions may instruct the end user of the kit that a subject having a higher level of NOL3 subject may be selected for a treatment regimen additionally comprising an IAP inhibitor. Furthermore, the kit may comprise the agent used in the treatment regimen to reduce the activity of NOL3 and/or an IAP inhibitor.

In another aspect, the kit of the present invention includes means for selecting a subject having cancer for a treatment regimen. In this aspect, the instructions can instruct the end user of the kit that a subject having an equivalent or lower levels of NOL3 relative to the reference level is selected for a treatment regimen including an IAP inhibitor.

In still other embodiments, the kit may include a means for identifying a compound as an anti-cancer agent. In this embodiment, the kit may comprise a cell line expressing NOL3 and/or a compound for use in treating the cell line. Furthermore, the instructions can instruct the end user of the kit that a compound that reduces the level of NOL3 expression may be identified as an anti-cancer agent.

Preferably, the kit is designed for use with a human subject, such as a human subject suffering from cancer. Examples of cancers that are embodied by the present invention, include but are not limited to breast, brain, ovarian, colorectal, gastric, prostate, testicular, uterine, cervical, pancreatic, skin, colon, stomach, esophagus, bladder, lung, and small cell lung cancer. In one embodiment, the subject suffers from a glioma; for example, an astrocytoma, ependymoma, oligodendroglioma, mixed glioma, and glioblastoma multiforme. In another embodiment, the subject suffers from a carcinoma; for example, ovarian carcinoma, breast carcinoma, prostate carcinoma, colorectal carcinoma, and small cell lung carcinoma. In another embodiment, the subject suffers from a hematologic malignancy; for example, acute leukemia, chronic leukemia, multiple myeloma, or lymphoma.

This invention is further illustrated by the following examples, which should not be construed as limiting. The contents of all references, patents and published patent applications cited throughout this application are incorporated herein by reference.

EXAMPLES

Example 1: PDGFR and IAP Inhibition Synergistically Inhibits Glioma Cell Growth

It has been proposed that cancer cells exist in a state of dynamic tension with a constant burden of pro-apoptotic signals counterbalanced by heightened expression of anti-apoptotic proteins. The IAPs constitute a final blockade of apoptosis through sequestration of caspase-3, -7, and -9 (FIG. 1A). Upon mitochondrial permeabilization, release of Smac/DIABLO into the cytoplasm results in binding to, and inactivation of, IAPs. Since IAPs are overexpressed in gliomas, it is possible that blockade of IAPs alone may be sufficient to shift the balance towards apoptosis (FIG. 1A). The small molecule LBW242 binds to the BIR3 domain of IAPs, and blocks their ability to sequester caspases. To confirm that LBW242 does in fact effectively function as a Smac mimetic, a FRET based competition assay that measured the ability of LBW242 to compete with Smac for binding to the BIR3 domain of XIAP was performed. LBW242 inhibited the interaction of full-length Smac to XIAP in a well-behaved sigmoidal dose-response relationship (FIG. 1B). To confirm the functional significance of the binding of LBW242 to IAPs, the effect of LBW242 binding on caspase activity in a cell-free system was assessed. In an assay in which the activity of caspase-9 was blocked by recombinant XIAP-BIR3, increasing doses of LB W242 resulted in caspase-9 activation with subsequent activation of caspase-3 and cleavage of a fluorogenic substrate (FIG. 1C).

Figure 1E:
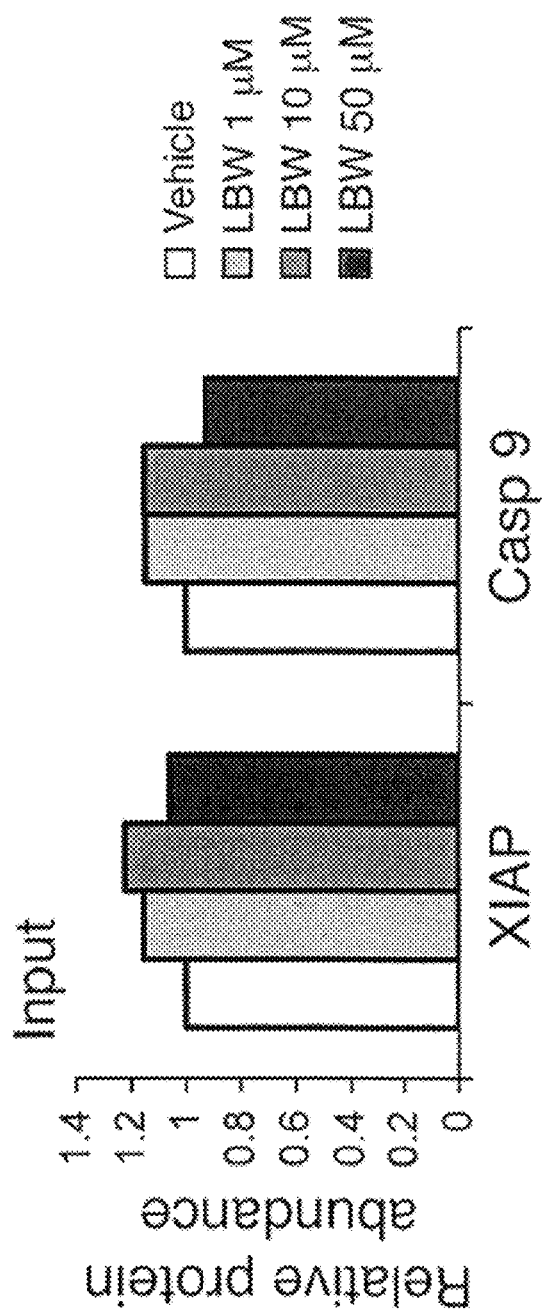
FIG. 1E depicts densitometric analysis of overall cellular levels of XIAP and caspase-9 after treatment with the indicated concentration of LBW242 relative to vehicle control.

Next, the effects of LBW242 in intact cells were assessed. LN827 glioma cells were exposed to LBW242 for 4 hours, and then endogenous caspase-9 was immunoprecipitated from whole cell extracts. Although LBW242 did not have any effect on the overall levels of caspase-9, or XIAP (FIGS. 1, D and E), the abundance of endogenous XIAP bound to caspase-9 was reduced in cells treated with LBW242 (FIGS. 1, D and F). These results establish the cellular permeability of LBW242 and the ability of LBW242 to disrupt endogenous binding of IAPs to caspase-9 in intact cells.

Figure 1G:
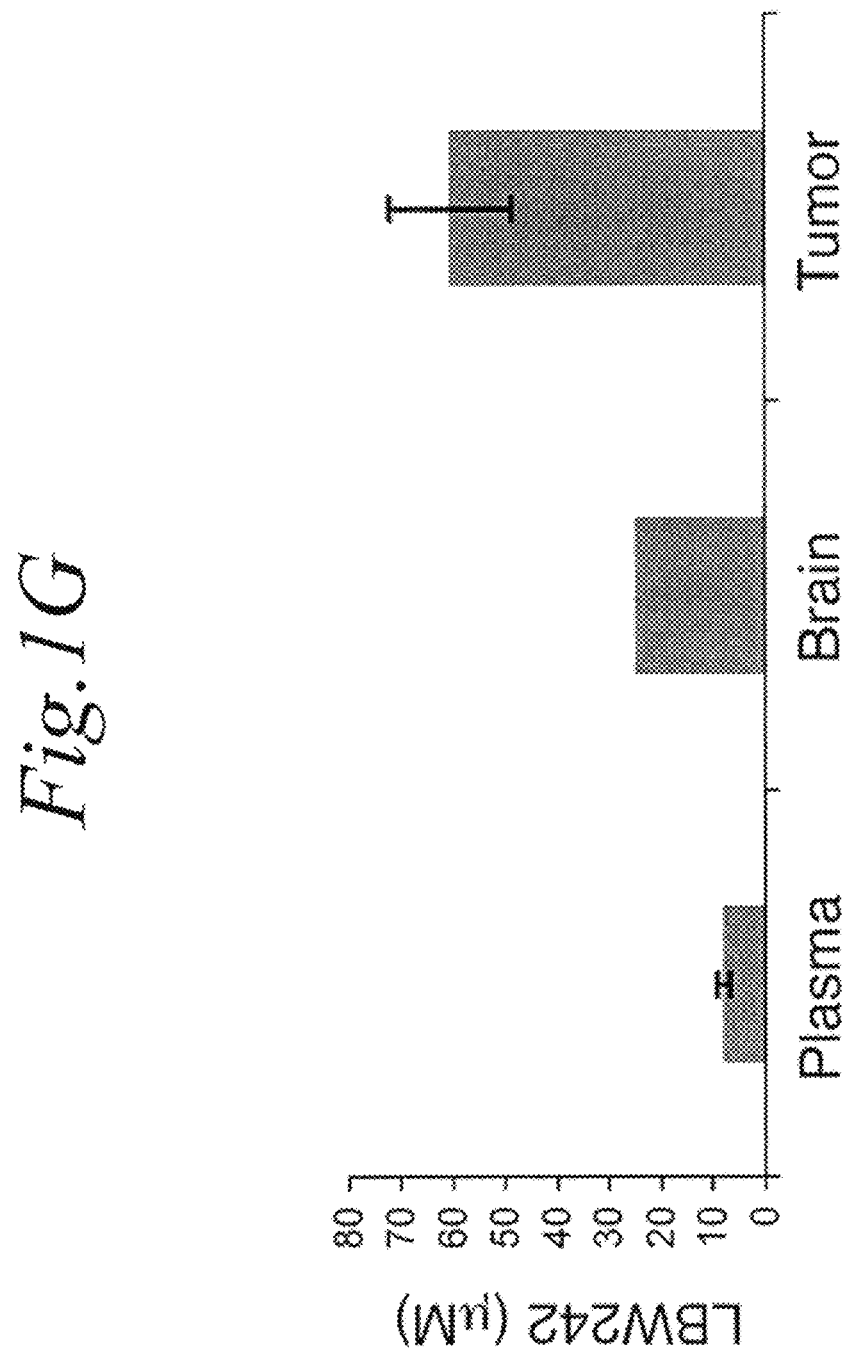
FIG. 1G: depicts a graph showing the concentration of LBW242 in plasma, brain and tumor of 3 SK—OV-3 tumor-bearing nude mice after 14 days of daily parenteral dosing of LBW242 (50 mg/kg).

To determine the achievable tissue concentrations of LBW242 in the in vivo setting, we administered LBW242 parenterally to mice at a dose of 50 mg/kg/d. After 14 days of daily dosing, LBW242 achieved a long-term steady-state concentration that exceeded 60 in tumors (FIG. 1G). For treatment of intracranial tumors, the blood-brain barrier (BBB) is an impediment to drug bioavailability. It was determined that LBW242 was able to cross even the intact BBB and achieve tissue concentrations of approximately 25 µM in normal brain (FIG. 1G). The BBB is at least partially disrupted within brain tumors, suggesting that achievable brain tumor levels exceed 25 µM.

The effect of the representative IAP inhibitor LBW242 on glioma cell proliferation was assessed, and no effect on the growth of U87 cells (FIG. 1H) or LN827 cells (data not shown) was observed with LBW242 as a single agent at concentrations of up to 50 µM. Since in vivo steady-state tissue levels of LBW242 exceed 25-60 µM (FIG. 1G), since there were no stand-alone effects on glioma growth up to 50 µM, and since caspase activity was most efficiently reversed in vitro at 50 µM concentrations, we used an exemplary concentration of 50 µM for all subsequent experiments.

Figure 2A:
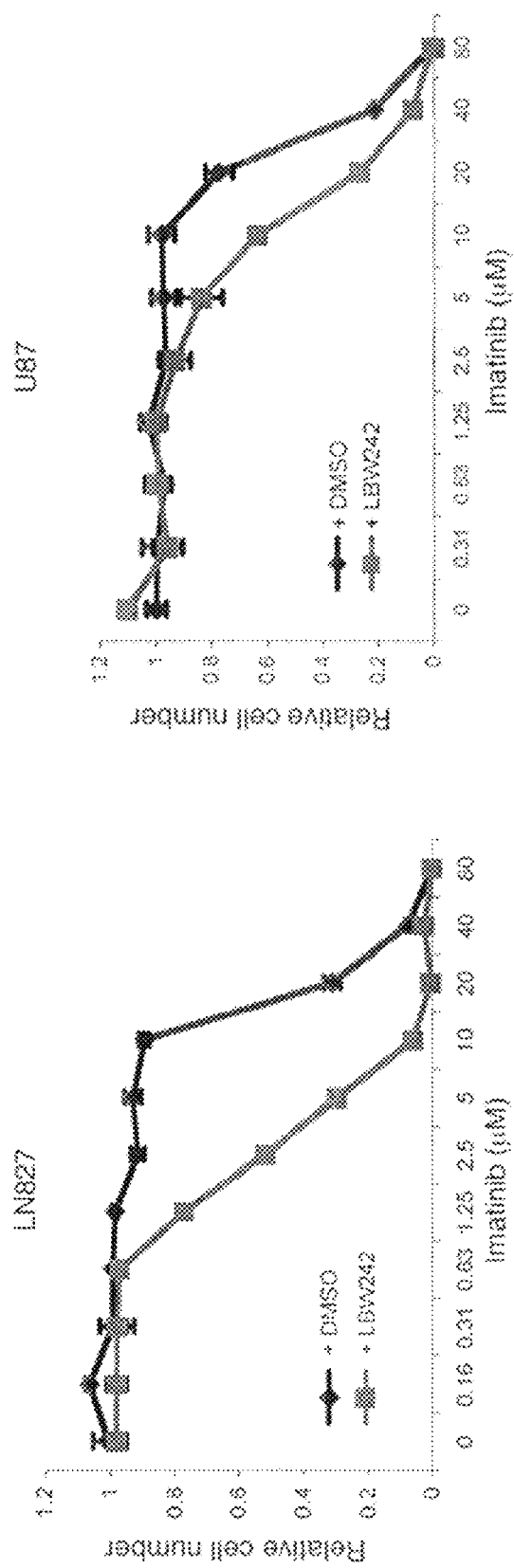
FIG. 2A: depicts a graph showing the treatment of LN827 and U87 cells with LBW242 and imatinib.
Figure 2B:
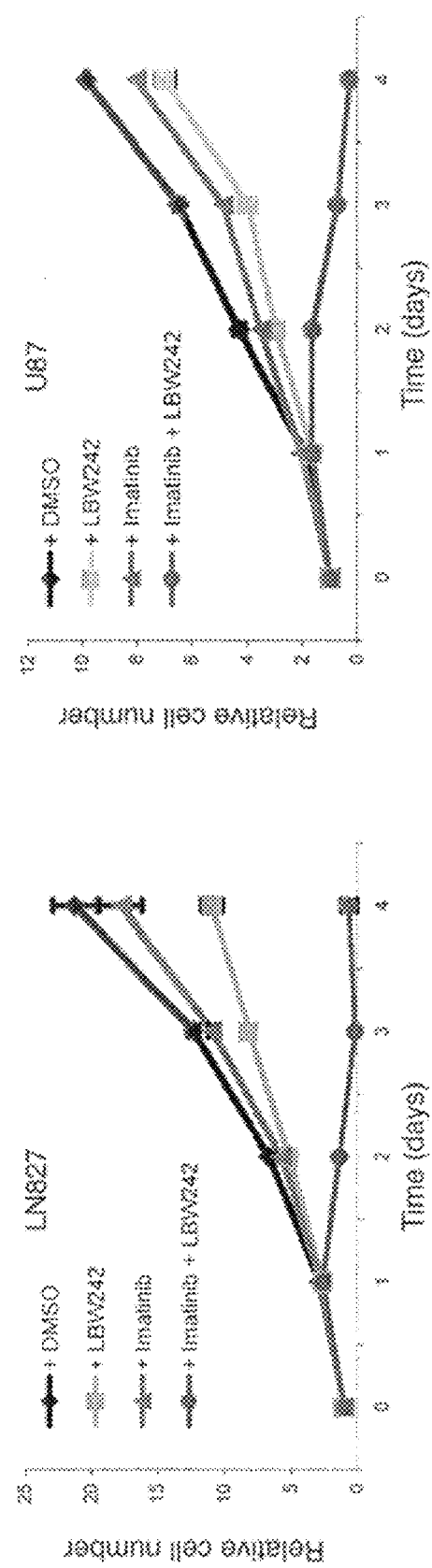
FIG. 2B: depicts a graph showing the effect of treatment with LBW242 and imatinib on cell growth over time in LN827 and U87 cells.

Although IAP inhibition had no stand-alone activity, it was hypothesized that apoptosis might be achieved by simultaneously increasing pro-apoptotic signals. Since PDGFR has a well-established role in gliomagenesis, and since withdrawal of growth factor signaling is pro-apoptotic in many systems (Klein et al., 2005) the combined effects of IAP and PDGFR inhibition on cell growth was assessed. As a single agent, imatinib inhibited cell growth at doses>10 μM. The addition of LBW242, which had no effect on cell growth alone, resulted in a shift in the imatinib dose-response curve towards increased sensitization in LN827 and U87 cells (FIG. 2A). Over four days of treatment, only mild cytostasis was apparent in cells treated with either imatinib or LBW242 alone, compared to frank cell death observed in cells treated with both agents (FIG. 2B).

Next, the effect of the small molecule kinase inhibitor, imatinib, on the inhibition of PDGFR was examined. While treatment with imatinib had no effect on the overall abundance of PDGFR, the activation state of PDGFR was almost completely abolished by imatinib at 2.5 uM in LN827 cells (FIG. 2C). When administered as mono-therapy, inhibition of LN827 cell growth was observed at imatinib concentrations>20 μM (FIG. 2A). In contrast, the synergistic effects on cell growth when imatinib was combined with LBW242 was observed at imatinib concentrations of approximately 1.25-2.5 μM (FIG. 2A). The correlation of dosages causing PDGFR inhibition and synergistic inhibition of tumor growth suggests that the response seen occurs due to inhibition of PDGFR. LBW242 had no effect on PDGFR abundance or activity (FIG. 2C), suggesting that the synergistic effects of the combination are not due to LBW242 potentiating the inhibitory effects of imatinib on PDGFR activation.

Figure 2D:
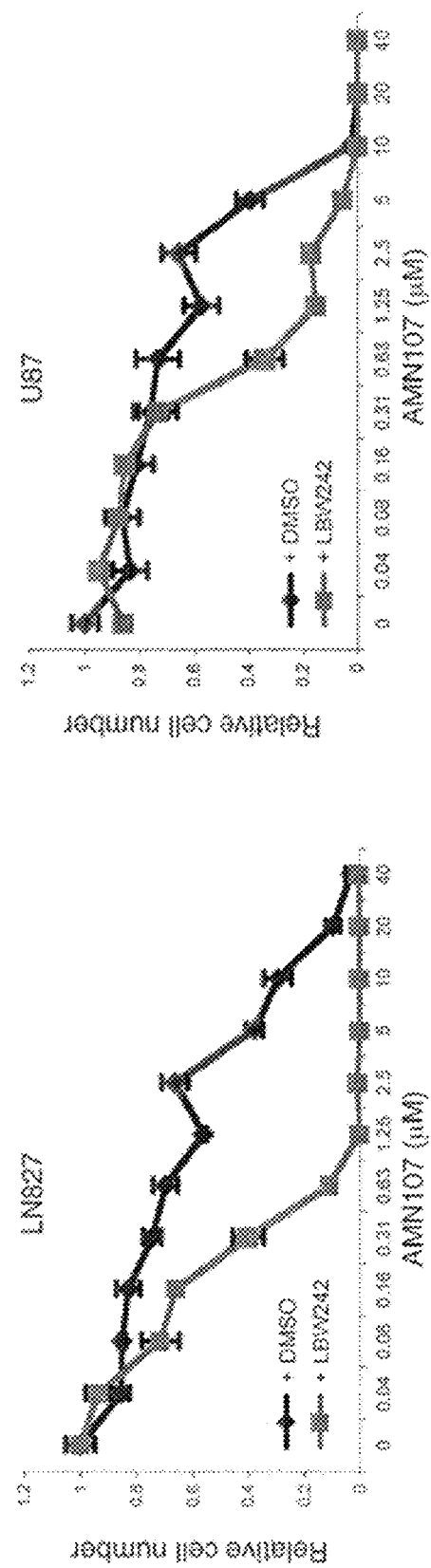
FIG. 2D: depicts a graph showing the effect of LBW242 and AMN107 on cell growth in LN827 and U87 cells.

To further confirm that the observed synergy resulted from PDGFR inhibition, the combination of IAP inhibitor LBW242 with an alternative PDGFR kinase inhibitor AMN107 (Weisberg et al., Cancer Cell. 2005 February; 7(2):129-41) was also tested (FIG. 2D). A synergistic inhibition of cell growth was again apparent with the combination treatment. Similar results were also seen when LBW242 was tested in combination with the PDGFR inhibitor dasatinib. Together, these results demonstrate that inhibition of IAPs in cancer cells, e.g., glioma cells, has little stand-alone activity, but inhibition of IAPs acts synergistically with inhibition of PDGFR, which is known to play a key role in gliomagenesis. Stand-alone activity was observed with imatinib alone, but only at concentrations>10 fold above that required for PDGFR inhibition, suggesting that "off-target" inhibition of other kinases contributes to this single agent activity.

Figure 3A:
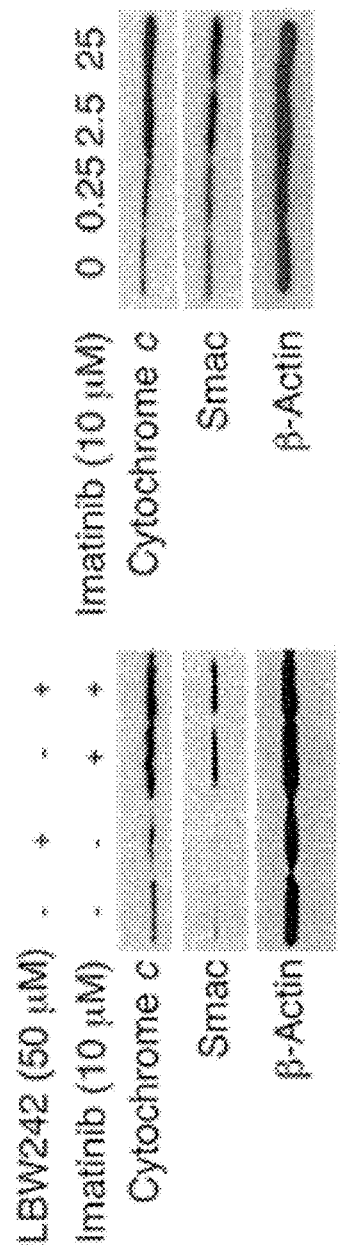
FIG. 3A: depicts an immunoblot showing the effect of treatment with imatinib and/or LBW242 on the release of cytoplasmic cytochrome c and Smac/Diablo in LN827 cells.

Example 2: Imatinib Activates the Intrinsic Apoptosis Pathway in Cancer Cells, but Apoptosis Requires Concomitant Blockade of IAPs Given the established role for PDGFR in gliomas, and in light of the above results, it was hypothesized that PDGFR inhibition may be producing a pro-apoptotic signal that was counteracted by downstream anti-apoptotic proteins. Multiple upstream pro-apoptotic signals converge at the level of the mitochondria, resulting in mitochondrial outer membrane permeabilization (MOMP) and release of the pro-apoptotic mediators cytochrome c and Smac/Diablo (FIG. 1A). It was therefore assessed whether imatinib induced MOMP by measuring cytoplasmic levels of cytochrome c and Smac/Diablo in cells following imatinib treatment. In LN827 cells, imatinib at 10 μM, which has no effect on cell growth (FIGS. 2A and B), led to a significant increase in both cytoplasmic cytochrome c and Smac/Diablo (FIG. 3A). Consistent with its mechanism of action, the IAP inhibitor LBW242 had no appreciable effect on cytochrome c or Smac/Diablo levels, either as a single agent or in combination with imatinib (FIG. 3A). The concentration of imatinib at which MOMP was observed was 2.5 μM (FIG. 3A), which was coincident with the concentration at which PDGFR activity was inhibited (FIG. 2C), and where synergistic killing with LBW242 was observed (FIG. 2A) in LN827 cells.

Figure 3B:
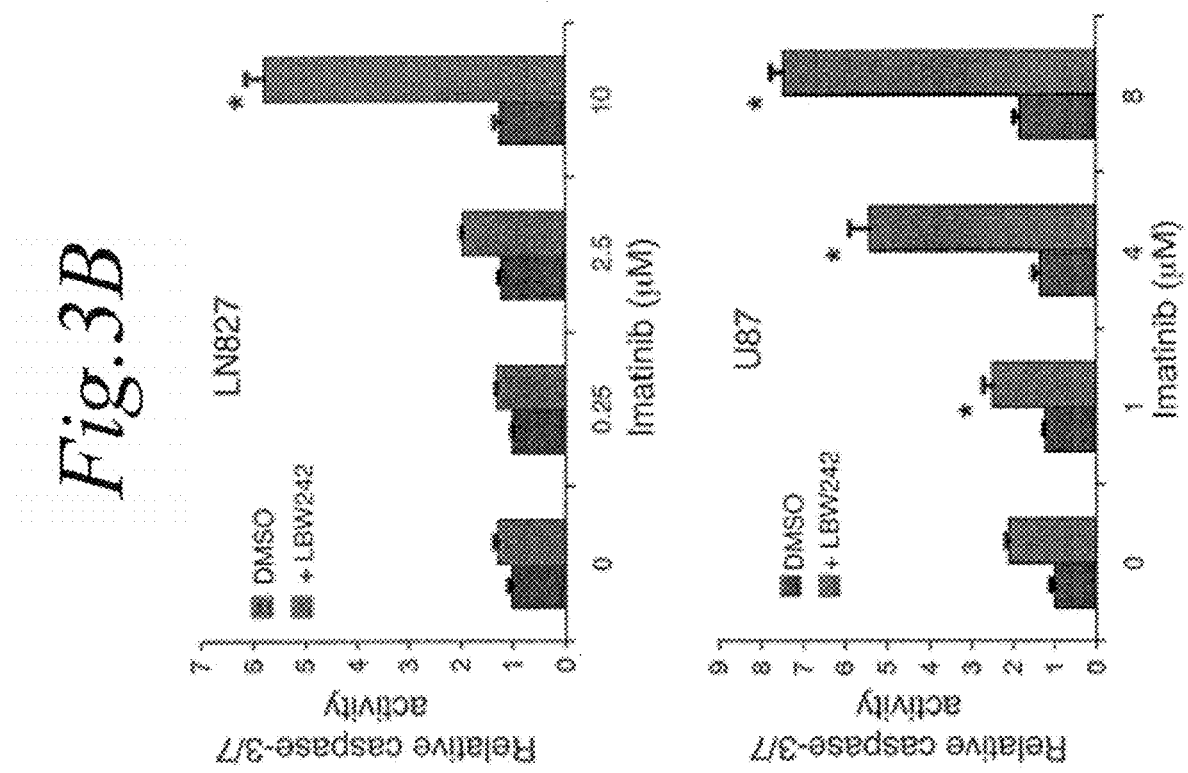
FIG. 3B: depicts a graph showing the effects of imatinib and LBW242 on the activation of caspase 3/7.
Figure 3C:
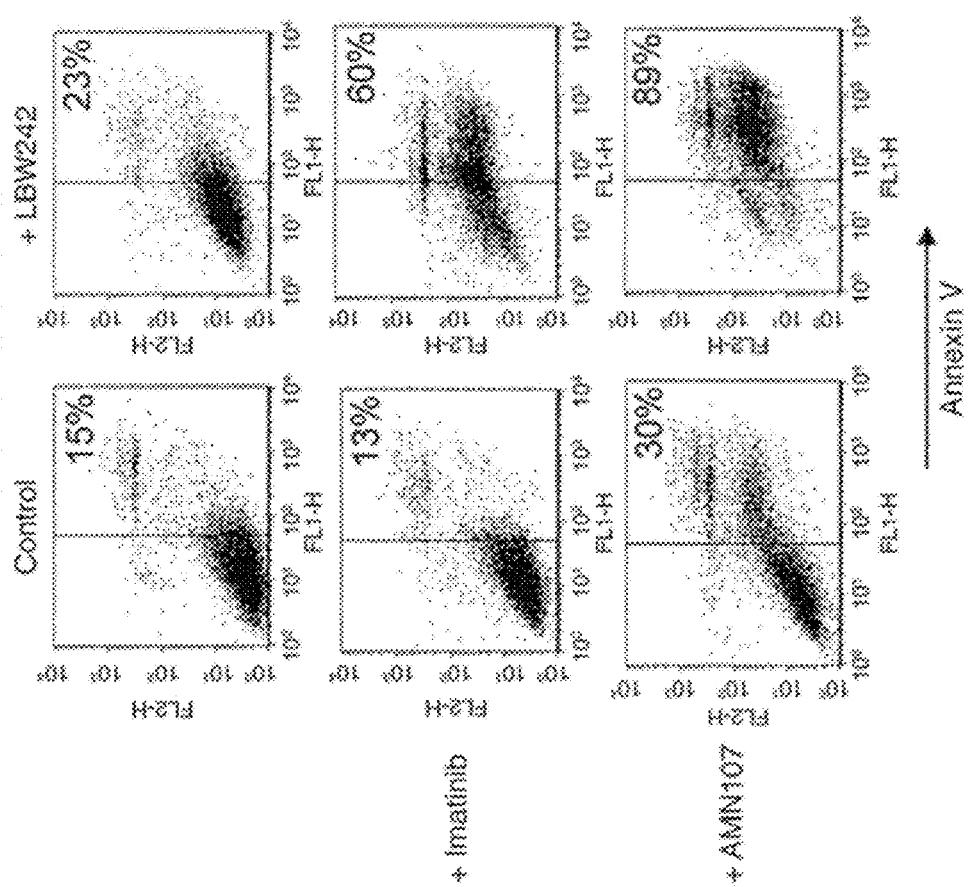
FIG. 3C: depicts graphs showing the effect of LBW242 in combination with or without imatinib or AMN107 on cellular apoptosis, cells positive for annexin V are to the right of the divider.

Although imatinib induced MOMP (FIG. 3A), there was no activation of caspase 3 or 7 when cells were treated with imatinib alone (FIG. 3B). In contrast, the addition of the IAP inhibitor LBW242 with imatinib resulted in significant activation of caspase 3/7 activity (FIG. 3B). To determine if the synergistic activation of caspase 3/7 activity resulted in apoptosis, the number of apoptotic cells staining positive with Annexin-V was measured. PDGFR inhibition with imatinib alone and IAP inhibition with LBW242 alone caused minimal change in basal apoptotic level, however, the combination of imatinib and LBW242 resulted in synergistic induction of apoptosis (FIG. 3C). A small increase in apoptosis was apparent with PDGFR inhibitor AMN107 alone, but again the addition of IAP inhibitor LBW242 resulted in the majority of tumor cells undergoing apoptosis (FIG. 3C).

Together, these results establish that imatinib activates the apoptosis cascade and MOMP, but that caspase 3 and 7 are not activated unless the activity of IAPB is simultaneously blocked. The combination of PDGFR and IAP inhibition produces synergistic induction of apoptosis.

Figure 4A:
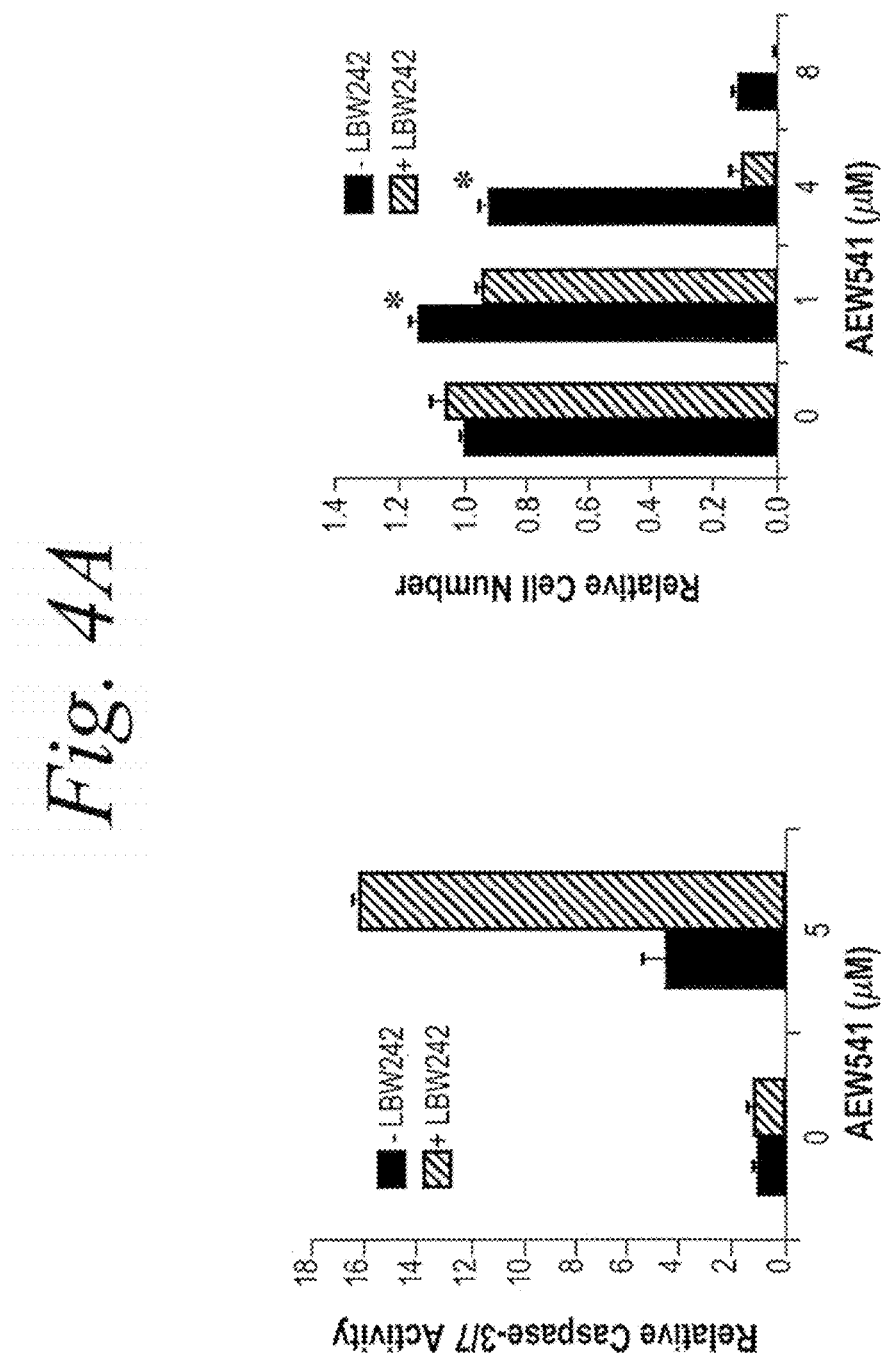
FIG. 4A: depicts two graphs showing the effect of LBW242 and AEW541 on cell growth and caspase activation.
Figure 4B:
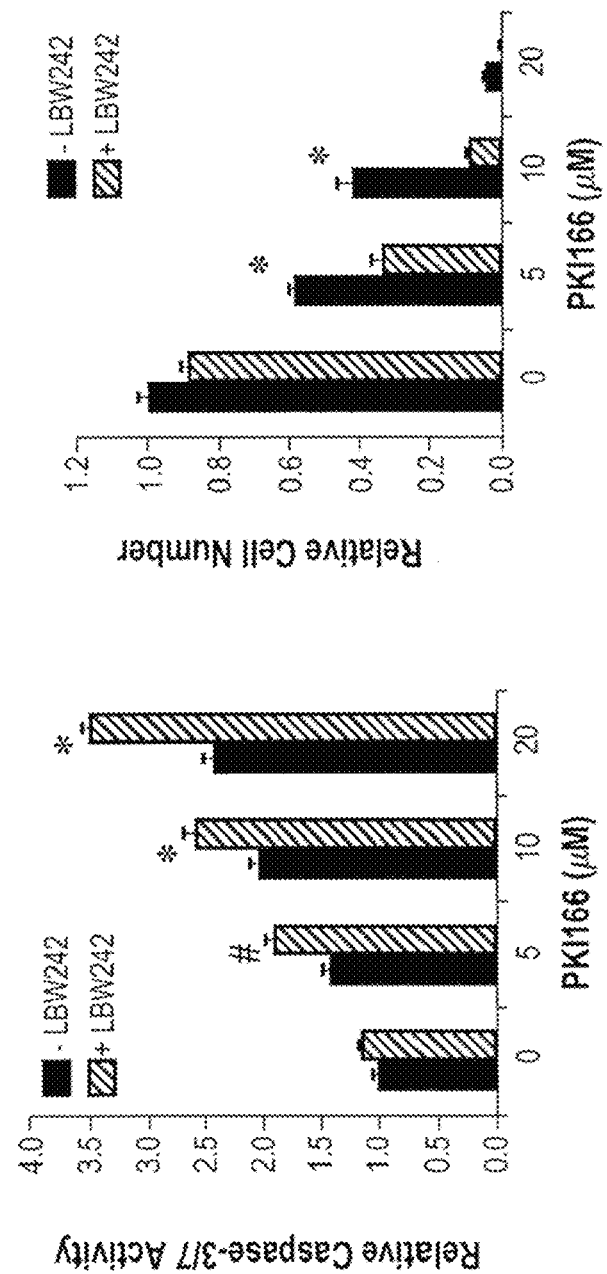
FIG. 4B: depicts two graphs showing the effect of PKI166 and LBW242 on cell growth and caspase activation.

Example 3: Receptor-Tyrosine Kinase (RTK) and IAP Inhibition Activates Caspases and Suppresses Tumor Growth Independent of Akt Several RTKs have been implicated in gliomagenesis, therefore it was hypothesized that the synergistic effects of PDGFR and IAP inhibition could be generalized to other growth factor receptors. First we assessed the combination of IAP inhibition and blockade of the growth factor receptor IGF-1R with NVP-AEW541, a highly specific IGF-1R kinase inhibitor (Garcia-Echeverria et al., 2004). The combination of AEW541 and LBW242 led to caspase 3/7 activation and synergistically inhibited tumor cell growth (FIG. 4A). Next we tested blockade of the growth factor receptor EGFR with the dual EGFR and HER2 kinase inhibitor PKI166 (Bruns et al., 2000). PKI166 as a single agent had a pro-apoptotic effect, resulting in increased levels of caspase 3/7 activation. The addition of IAP inhibition, however, led to enhanced caspase 3/7 activation and a correlative enhanced inhibition of glioma cell proliferation (FIG. 4B). This effect is likely more pronounced in primary tumors in vivo, as it is known that glioma cells reduce EGFR overexpression in culture (Ishii et at 1999).

Figure 4D:
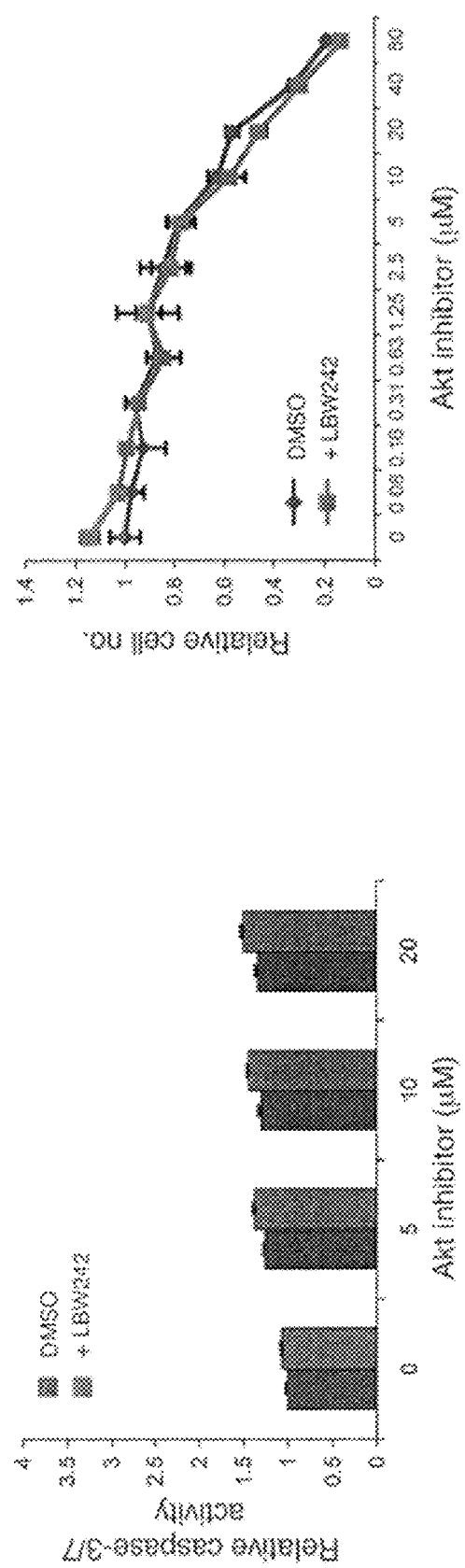
FIG. 4D: depicts two graphs showing the effects of an Akt inhibitor (triciribine) and LBW242 on caspase-3/7 activation.

Because PDGFR, EGFR and IGF-1R all activate Akt, and since Akt provides key anti-apoptotic signals, we asked whether the demonstrated induction of apoptosis and inhibition of cell growth occur secondarily to Akt inactivation. As shown in FIG. 4C, Akt is tonically phosphorylated in LN827 cells. Administration of imatinib with or without the IAP inhibitor LBW242 did not inhibit Akt phosphorylation, nor did it inhibit the downstream phosphorylation of Bad (FIG. 4C). Furthermore, the combination of LBW242 and the specific Akt inhibitor triciribine, did not demonstrate any notable synergistic effect on either caspase 3/7 activation or tumor cell proliferation (FIG. 4D). Thus the synergy between growth factor inhibition and IAP inhibition occurs independently of a change in Akt status.

Figure 4F:
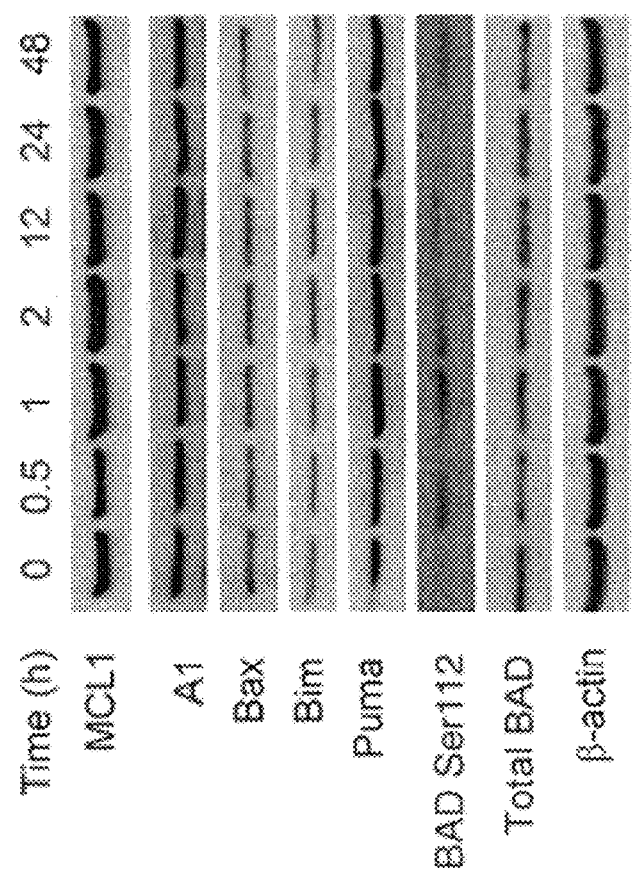
FIG. 4F: depicts a Western blot showing that treatment of LN827 cells with imatinib did not affect the expression of anti- or pro-apoptotic members of the BCL-2 family of proteins.

Alternative mechanisms by which growth factor inhibition may lead to activation of the apoptotic pathway and mitochondrial permeabilization in tumor cells, e.g., gliomas, were also tested. Because Erk 1/2 is another downstream target of growth factor receptors, Erk 1/2 phosphorylation status was measured, and it was determined that treatment with imatinib did not inhibit phosphorylation of Erk 1/2 (FIG. 4E). It was next investigated whether treatment with imatinib led to a change in expression of a number of anti- or pro-apoptotic members of the BCL-2 family of proteins. A significant change in expression was not observed for any of the proteins tested (FIG. 4F).

Example 4: Growth Factor Receptor Inhibition with Imatinib Downregulates Expression of NOL3, a Protein that is Overexpressed in Cancer Cells To comprehensively assess the effect of growth factor inhibition on a broad number of pro- and anti-apoptotic mediators, mRNA expression was assessed using a 96-well quantitative RT-PCR microarray (Alikhani et al., 2005). Treatment with imatinib 10 μM resulted in a significant change in the expression of only one gene tested: NOL3 (Table 1). Imatinib was found to downregulate NOL3 in 7 individual multi-well screens. NOL3 encodes Nucleolar Protein 3 (Apoptosis Repressor with CARD domain (ARC)), which is known to be highly expressed in normal cardiac, skeletal and neurological tissue (Hong et at., 2003; Koseki et at., 1998). An independent quantitative RT-PCR analysis confirmed that imatinib significantly reduced NOL3 mRNA expression (FIG. 5A). Western blot confirmed that the reduction in NOL3 transcription over time leads to a correlative decrease in NOL3 protein levels, but not of other anti-apoptotic proteins (FIG. 5B).

Figure 5D:
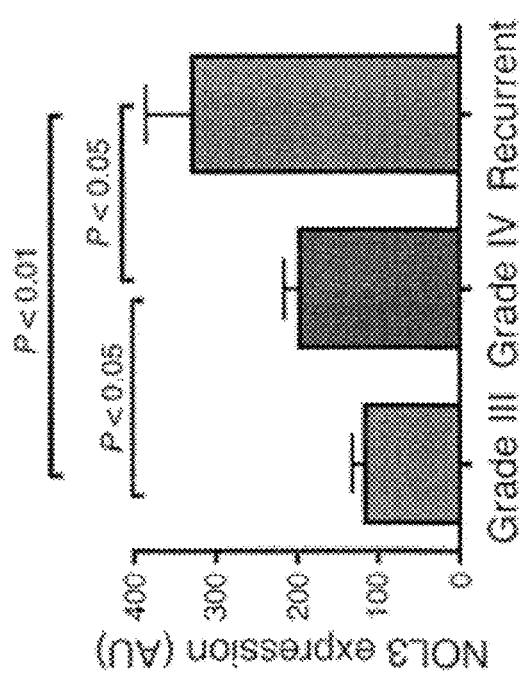
FIG. 5D: depicts a graph showing a comparison of the expression levels of NOL3 mRNA in grade III, grade IV, and recurrent high-grade gliomas.
Figure 5E:
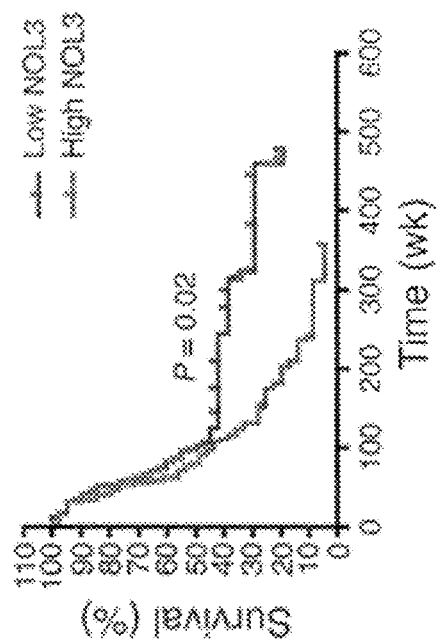
FIG. 5E: depicts a graph showing the correlation between high NOL3 expression in tumor specimens and inferior patient survival.
Figure 5G:
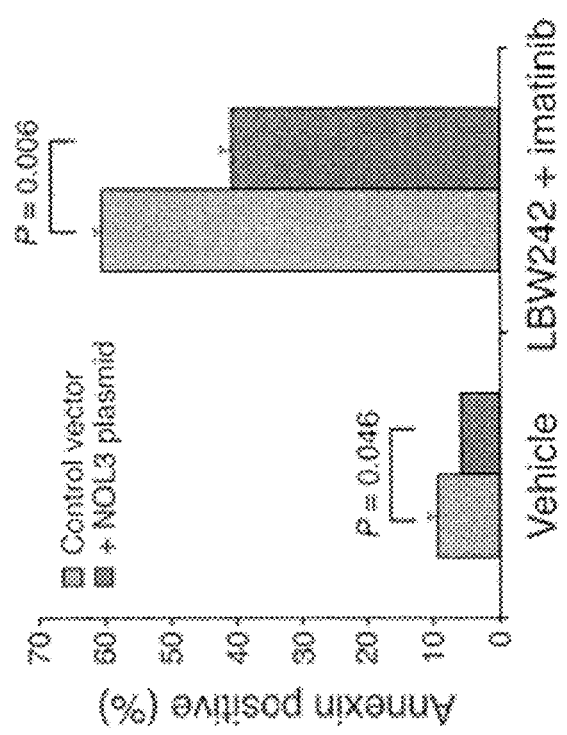
FIG. 5G: depicts a graph showing the effects of LBW242 and imatinib on apoptosis in cells expressing a plasmid carrying NOL3 or a control plasmid.

To validate the clinical relevance of NOL3 in cancer, the expression of NOL3 was evaluated in malignant glioma using mRNA expression data (Phillips et al., 2006; Sun et al., 2006). This analysis found that NOL3 was significantly overexpressed in malignant gliomas when compared with normal brain tissue (FIG. 5C). Evaluation of NOL3 expression in subsets of malignant glioma specimens revealed increasing expression with worsening grade of tumor (FIG. 5D). Similarly, high expression of NOL3 in tumor specimens correlated with inferior patient survival (FIG. 5E).

Table 1 depicts data obtained from mRNA microanalysis for expression of genes in the apoptotic pathway. Data represents the average gene expression levels for 3 separate samples treated with or without 10 μM imatinib for 36 hours.

TABLE 1

RNA Microarray Analysis

| Symbol | Well | AVG $C_t$ without normalization | | $2^{-\Delta C_t}$ | | Fold Difference | T-TEST | Fold Up- or Down-Regulation |
|---|---|---|---|---|---|---|---|---|
| | | Test Sample | Control Sample | Test Sample | Control Sample | Test Sample/ Control Sample | p value | Test Sample/ Control Sample |
| ABL1 | A01 | 28.19 | 25.31 | 5.2E-03 | 1.1E-02 | 0.48 | 0.0796 | -2.09 |
| AKT1 | A02 | 25.93 | 23.21 | 2.5E-02 | 4.7E-02 | 0.53 | 0.0812 | -1.89 |
| APAF1 | A03 | 29.60 | 27.96 | 1.9E-03 | 1.7E-03 | 1.12 | 0.1378 | 1.12 |
| BAD | A04 | 32.50 | 29.81 | 2.6E-04 | 4.8E-04 | 0.54 | 0.1288 | -1.84 |
| BAG1 | A05 | 28.24 | 26.39 | 5.0E-03 | 5.1E-03 | 0.97 | 0.1801 | -1.03 |
| BAG3 | A06 | 28.52 | 26.84 | 4.1E-03 | 3.8E-03 | 1.09 | 0.1965 | 1.09 |
| BAG4 | A07 | 28.26 | 27.23 | 4.9E-03 | 2.9E-03 | 1.71 | 0.1687 | 1.71 |
| BAK1 | A08 | 31.60 | 29.32 | 4.8E-04 | 6.7E-04 | 0.72 | 0.1411 | -1.39 |
| BAX | A09 | 25.10 | 23.80 | 4.4E-02 | 3.1E-02 | 1.43 | 0.2034 | 1.43 |
| BCL10 | A10 | 26.83 | 25.69 | 1.3E-02 | 8.3E-03 | 1.59 | 0.2257 | 1.59 |
| BCL2 | A11 | 31.28 | 30.53 | 6.1E-04 | 2.9E-04 | 2.08 | 0.4084 | 2.08 |
| BCL2A1 | A12 | 35.00 | 35.00 | 4.6E-05 | 1.3E-05 | N/A | N/A | 3.50 |
| BCL2L1 | B01 | 26.30 | 25.41 | 1.9E-02 | 1.0E-02 | 1.89 | 0.4089 | 1.89 |
| BCL2L10 | B02 | 35.00 | 35.00 | 4.6E-05 | 1.3E-05 | N/A | N/A | 3.50 |
| BCL2L11 | B03 | 33.80 | 32.89 | 1.1E-04 | 5.7E-05 | 1.86 | 0.1340 | 1.86 |
| BCL2L2 | B04 | 29.65 | 27.32 | 1.9E-03 | 2.7E-03 | 0.70 | 0.1334 | -1.44 |
| BCLAF1 | B05 | 26.55 | 25.09 | 1.6E-02 | 1.3E-02 | 1.27 | 0.1262 | 1.27 |
| BFAR | B06 | 26.30 | 24.61 | 1.9E-02 | 1.8E-02 | 1.09 | 0.1478 | 1.09 |
| BID | B07 | 25.78 | 23.34 | 2.7E-02 | 4.3E-02 | 0.65 | 0.0784 | -1.55 |
| BIK | B08 | 35.00 | 35.00 | 4.6E-05 | 1.3E-05 | N/A | N/A | 3.50 |
| BIRC1 | B09 | 35.00 | 35.00 | 4.6E-05 | 1.3E-05 | N/A | N/A | 3.50 |
| BIRC2 | B10 | 33.60 | 31.51 | 1.2E-04 | 1.5E-04 | 0.82 | 0.0520 | -1.22 |
| BIRC3 | B11 | 33.63 | 31.83 | 1.2E-04 | 1.2E-04 | 1.01 | 0.1117 | 1.01 |
| BIRC4 | B12 | 26.54 | 25.52 | 1.6E-02 | 9.4E-03 | 1.72 | 0.2803 | 1.72 |
| BIRC6 | C01 | 26.95 | 25.33 | 1.2E-02 | 1.1E-02 | 1.14 | 0.1393 | 1.14 |
| BIRC8 | C02 | 35.00 | 35.00 | 4.6E-05 | 1.3E-05 | N/A | N/A | 3.50 |
| BNIP1 | C03 | 30.08 | 27.77 | 1.4E-03 | 2.0E-03 | 0.71 | 0.0992 | -1.42 |
| BNIP2 | C04 | 25.58 | 24.18 | 3.1E-02 | 2.4E-02 | 1.32 | 0.1720 | 1.32 |
| BNIP3 | C05 | 23.58 | 21.46 | 1.3E-01 | 1.6E-01 | 0.81 | 0.0667 | -1.24 |
| BNIP3L | C06 | 23.67 | 21.96 | 1.2E-01 | 1.1E-01 | 1.07 | 0.0379 | 1.07 |
| BRAF | C07 | 30.89 | 29.90 | 7.9E-04 | 4.5E-04 | 1.77 | 0.2579 | 1.77 |
| CARD4 | C08 | 33.59 | 31.80 | 1.2E-04 | 1.2E-04 | 1.01 | 0.1548 | 1.01 |
| CARD6 | C09 | 29.58 | 28.29 | 2.0E-03 | 1.4E-03 | 1.44 | 0.2363 | 1.44 |
| CARD8 | C10 | 29.39 | 28.13 | 2.2E-03 | 1.5E-03 | 1.46 | 0.1865 | 1.46 |
| CASP1 | C11 | 29.17 | 27.56 | 2.6E-03 | 2.3E-03 | 1.15 | 0.1185 | 1.15 |
| CASP10 | C12 | 31.12 | 29.84 | 6.8E-04 | 4.7E-04 | 1.44 | 0.1684 | 1.44 |
| CASP14 | D01 | 35.00 | 35.00 | 4.6E-05 | 1.3E-05 | N/A | N/A | 3.50 |
| CASP2 | D02 | 27.33 | 24.98 | 9.4E-03 | 1.4E-02 | 0.69 | 0.0730 | -1.45 |
| CASP3 | D03 | 27.37 | 24.92 | 9.1E-03 | 1.4E-02 | 0.64 | 0.0881 | -1.55 |
| CASP4 | D04 | 25.49 | 25.25 | 3.4E-02 | 1.1E-02 | 2.97 | 0.7013 | 2.97 |
| CASP5 | D05 | 35.00 | 35.00 | 4.6E-05 | 1.3E-05 | N/A | N/A | 3.50 |

TABLE 1-continued

RNA Microarray Analysis

| Symbol | Well | AVG C$_t$ without normalization | | 2$^{-\Delta C_t}$ | | Fold Difference | | Fold Up- or Down-Regulation |
|---|---|---|---|---|---|---|---|---|
| | | Test Sample | Control Sample | Test Sample | Control Sample | Test Sample/ Control Sample | T-TEST p value | Test Sample/ Control Sample |
| CASP6 | D06 | 28.55 | 26.88 | 4.0E−03 | 3.7E−03 | 1.10 | 0.1367 | 1.10 |
| CASP7 | D07 | 28.54 | 26.02 | 4.0E−03 | 6.6E−03 | 0.61 | 0.1135 | −1.64 |
| CASP8 | D08 | 30.98 | 29.58 | 7.4E−04 | 5.6E−04 | 1.32 | 0.1070 | 1.32 |
| CASP9 | D09 | 30.71 | 28.86 | 9.0E−04 | 9.3E−04 | 0.97 | 0.1561 | −1.03 |
| CD40 | D10 | 28.85 | 27.18 | 3.3E−03 | 3.0E−03 | 1.11 | 0.1995 | 1.11 |
| CD40LG | D11 | 35.00 | 35.00 | 4.6E−05 | 1.3E−05 | N/A | N/A | 3.50 |
| CFLAR | D12 | 26.61 | 28.20 | 1.5E−02 | 1.5E−03 | 10.54 | 0.6743 | 10.54 |
| CIDEA | E01 | 33.18 | 32.74 | 1.6E−04 | 6.3E−05 | 2.58 | 0.6905 | 2.58 |
| CIDEB | E02 | 35.00 | 35.00 | 4.6E−05 | 1.3E−05 | N/A | N/A | 3.50 |
| CRADD | E03 | 30.15 | 28.26 | 1.3E−03 | 1.4E−03 | 0.94 | 0.1088 | −1.06 |
| DAPK1 | E04 | 32.47 | 30.71 | 2.7E−04 | 2.6E−04 | 1.03 | 0.1567 | 1.03 |
| DFFA | E05 | 25.52 | 24.17 | 3.3E−02 | 2.4E−02 | 1.37 | 0.1909 | 1.37 |
| FADD | E06 | 25.55 | 23.63 | 3.2E−02 | 3.5E−02 | 0.93 | 0.1479 | −1.08 |
| FAS | E07 | 26.37 | 25.35 | 1.8E−02 | 1.1E−02 | 1.72 | 0.2207 | 1.72 |
| FASLG | E08 | 35.00 | 35.00 | 4.6E−05 | 1.3E−05 | N/A | N/A | 3.50 |
| GADD45A | E09 | 25.76 | 24.43 | 2.8E−02 | 2.0E−02 | 1.39 | 0.2036 | 1.39 |
| HRK | E10 | 35.00 | 35.00 | 4.6E−05 | 1.3E−05 | N/A | N/A | 3.50 |
| IGF1R | E11 | 27.41 | 26.77 | 8.9E−03 | 3.9E−03 | 2.24 | 0.4110 | 2.24 |
| LTA | E12 | 35.00 | 35.00 | 4.6E−05 | 1.3E−05 | N/A | N/A | 3.50 |
| LTBR | F01 | 26.40 | 25.44 | 1.8E−02 | 9.9E−03 | 1.81 | 0.1970 | 1.81 |
| MCL1 | F02 | 26.33 | 24.55 | 1.9E−02 | 1.8E−02 | 1.02 | 0.2555 | 1.02 |
| NOL3 | F03 | 30.71 | 26.52 | 9.0E−04 | 4.7E−03 | 0.19 | 0.0589 | −5.21 |
| PYCARD | F04 | 33.99 | 31.55 | 9.3E−05 | 1.4E−04 | 0.65 | 0.0011 | −1.55 |
| RIPK2 | F05 | 29.98 | 27.94 | 1.5E−03 | 1.8E−03 | 0.85 | 0.1470 | −1.17 |
| TNF | F06 | 33.81 | 32.77 | 1.0E−04 | 6.2E−05 | 1.70 | 0.1793 | 1.70 |
| TNFRSF10A | F07 | 33.61 | 32.19 | 1.2E−04 | 9.2E−05 | 1.31 | 0.1995 | 1.31 |
| TNFRSF10B | F08 | 25.87 | 24.51 | 2.6E−02 | 1.9E−02 | 1.36 | 0.2139 | 1.36 |
| TNFRSF11B | F09 | 31.81 | 29.48 | 4.2E−04 | 6.0E−04 | 0.70 | 0.0690 | −1.44 |
| TNFRSF1A | F10 | 31.11 | 29.63 | 6.8E−04 | 5.4E−04 | 1.26 | 0.3894 | 1.26 |
| TNFRSF21 | F11 | 28.12 | 26.49 | 5.4E−03 | 4.8E−03 | 1.13 | 0.1069 | 1.13 |
| TNFRSF25 | F12 | 31.87 | 29.16 | 4.0E−04 | 7.5E−04 | 0.53 | 0.0928 | −1.87 |
| TNFRSF7 | G01 | 34.76 | 33.97 | 5.4E−05 | 2.7E−05 | 2.03 | 0.0490 | 2.03 |
| TNFRSF9 | G02 | 30.89 | 27.62 | 7.9E−04 | 2.2E−03 | 0.36 | 0.0077 | −2.77 |
| TNFSF10 | G03 | 34.68 | 32.97 | 5.8E−05 | 5.3E−05 | 1.08 | 0.0104 | 1.08 |
| TNFSF7 | G04 | 27.02 | 24.87 | 1.2E−02 | 1.5E−02 | 0.79 | 0.0955 | −1.26 |
| TNFSF8 | G05 | 35.00 | 35.00 | 4.6E−05 | 1.3E−05 | N/A | N/A | 3.50 |
| TP53 | G06 | 26.32 | 24.49 | 1.9E−02 | 1.9E−02 | 0.99 | 0.0696 | −1.01 |
| TP53BP2 | G07 | 30.38 | 29.19 | 1.1E−03 | 7.4E−04 | 1.53 | 0.3833 | 1.53 |
| TP73 | G08 | 34.67 | 33.80 | 5.8E−05 | 3.0E−05 | 1.92 | 0.0513 | 1.92 |
| TRADD | G09 | 26.11 | 24.66 | 2.2E−02 | 1.7E−02 | 1.28 | 0.1791 | 1.28 |
| TRAF2 | G10 | 28.27 | 26.74 | 4.9E−03 | 4.0E−03 | 1.22 | 0.2224 | 1.22 |
| TRAF3 | G11 | 26.17 | 24.81 | 2.1E−02 | 1.5E−02 | 1.36 | 0.1938 | 1.36 |
| TRAF4 | G12 | 27.10 | 25.86 | 1.1E−02 | 7.4E−03 | 1.49 | 0.1860 | 1.49 |
| 18SrRNA | H01 | 11.70 | 9.82 | 4.7E+02 | 5.0E+02 | 0.95 | 0.2526 | −1.05 |
| HPRT1 | H02 | 28.09 | 25.31 | 5.5E−03 | 1.1E−02 | 0.51 | 0.0615 | −1.95 |
| RPL13A | H03 | 26.46 | 24.63 | 1.7E−02 | 1.7E−02 | 0.98 | 0.1298 | −1.02 |
| GAPDH | H04 | 18.29 | 17.07 | 4.9E+00 | 3.3E+00 | 1.50 | 0.1850 | 1.50 |
| ACTB | H05 | 18.41 | 17.08 | 4.5E+00 | 3.2E+00 | 1.39 | 0.1238 | 1.39 |
| ACTB | H06 | 20.79 | 20.13 | 8.7E−01 | 3.9E−01 | 2.22 | 0.0214 | 2.22 |
| ACTB | H07 | 22.67 | 23.06 | 2.4E−01 | 5.1E−02 | N/A | 0.2580 | 4.60 |
| ACTB | H08 | 24.76 | 23.73 | 5.6E−02 | 3.2E−02 | 1.71 | 0.4045 | 1.71 |
| ACTB | H09 | 26.04 | 24.88 | 2.3E−02 | 1.5E−02 | 1.57 | 0.4852 | 1.57 |
| ACTB | H10 | 25.39 | 23.14 | 3.6E−02 | 4.9E−02 | 0.74 | 0.2515 | −1.36 |
| ACTB | H11 | 32.54 | 31.98 | 2.5E−04 | 1.1E−04 | 2.38 | 0.7092 | 2.38 |
| ACTB | H12 | 35.00 | 35.00 | 4.6E−05 | 1.3E−05 | N/A | N/A | 3.50 |

Example 5: NOL3 is an Important Mediator of the Synergy Between Growth Factor Receptor Inhibition and IAP Inhibition It was then investigated whether the effect of imatinib on NOL3 expression is an important mediator of the observed synergy between growth factor receptor inhibition (e.g., mediated by imatinib) and IAP inhibition (e.g., mediated by LBW242). NOL3 was ectopically expressed in LN827 cells (FIG. 5F), and the effect on induction of apoptosis by imatinib and LBW242 was assessed. Transfection with NOL3 led to a marginal decrease in basal levels of apoptosis but had a far more significant impact on the proapoptotic effects of treatment with LBW242 and imatinib, with a 30% reduction in the number of cells undergoing apoptosis when compared with control cells (FIG. 5O).

Figure 5I:
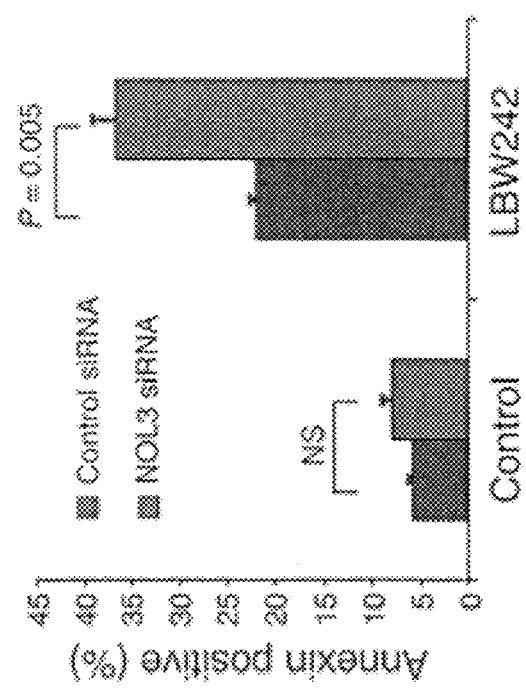
FIG. 5I: depicts a graph showing the combined effect of NOL3 knockdown and treatment with LBW242 on cellular apoptosis.

To further test the importance of NOL3 expression to IAP inhibitor-imatinib synergy, we assessed whether decreasing NOL3 expression alone was sufficient to sensitize cells to LBW242. siRNA knockdown of NOL3 in LN827 cells led to decreased protein abundance (FIG. 5H). While NOL3 depletion alone did not significantly increase apoptosis (FIG. 5I), depletion of NOL3 combined with LBW242 resulted in a significant increase in cellular apoptosis (FIG.

Figure 5J:
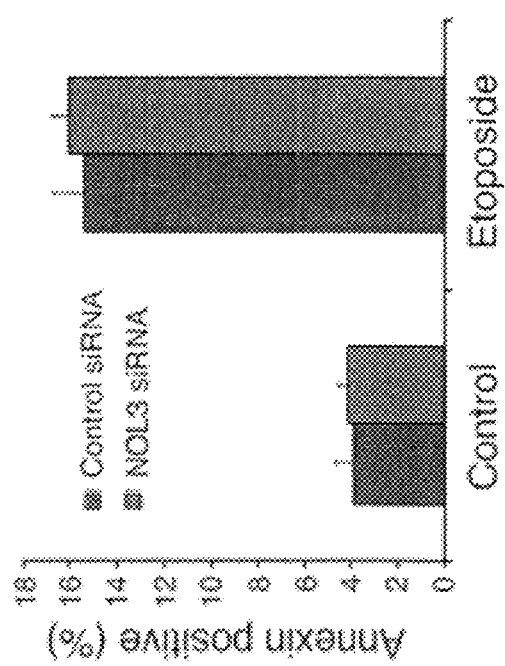
FIG. 5J: depicts a graph showing the combined effect of NOL3 knockdown and treatment with Etoposide on cellular apoptosis.

5I). In contrast, NOL3 depletion had no effect on the induction of apoptosis by etoposide (FIG. 5J). Taken together, these results show that a reduction in NOL3 expression is necessary for the observed synergy between imatinib and the IAP inhibitor LBW242, and further that reduced NOL3 expression is sufficient to sensitize cells to the pro-apoptotic effects of IAP inhibitor treatment.

Figure 6B:
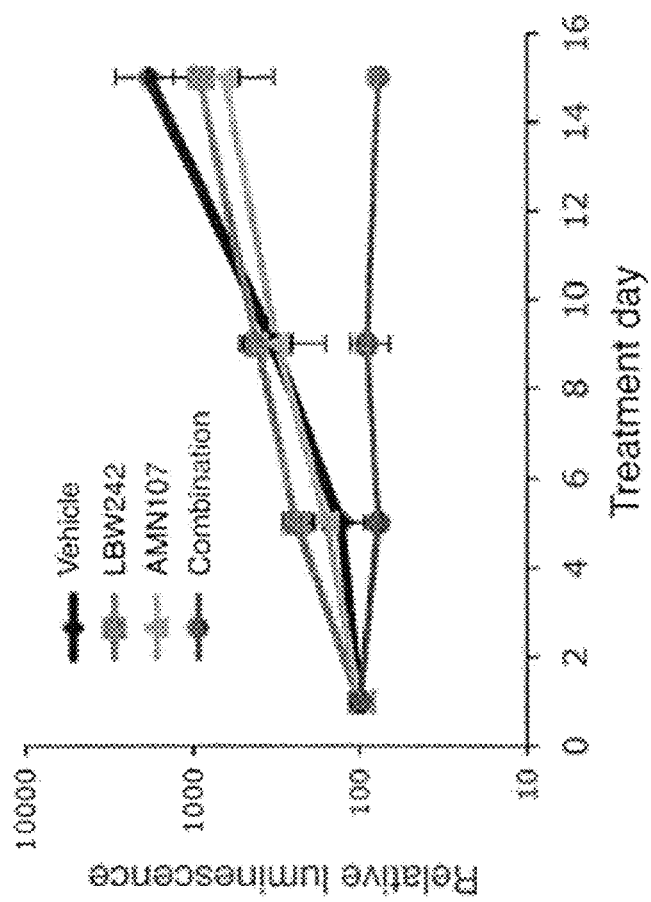
FIG. 6B: depicts a graph showing tumor burden in mice treated with vehicle, AMN107, LBW242 or AMN107 and LBW242.

Example 6: Growth Factor Receptor Inhibition Synergizes with IAP Inhibition to Suppress Tumor Growth In Vivo The combination of growth factor inhibition and IAP inhibition was tested in an orthotopic glioma model. LN827 cells were stereotactically implanted into the brains of mice. Tumor burden was serially followed using bioluminescence imaging. Animals with established tumors, characterized by logarithmically increasing tumor burden, were divided into treatment cohorts. One group was treated with AMN107 at 100 mg/kg per day by oral gavage; one group was treated with LBW242 at 50 mg/kg twice per day by oral gavage; one group was treated with vehicle; and one group was treated with the combination of LBW242 and AMN107. Consistent with the in vitro studies, monotherapy with either AMN107 or LBW242 alone had no appreciable effect on tumor growth (FIG. 6A and FIG. 6B). In contrast, animals treated with both AMN107 and LBW242 had complete cessation of tumor growth (FIG. 6A and FIG. 6B). These results establish that combined inhibition of growth factor receptors, e.g., PDGFR, and IAPs produces synergistic anti-tumor efficacy in vivo.

Figure 6C:
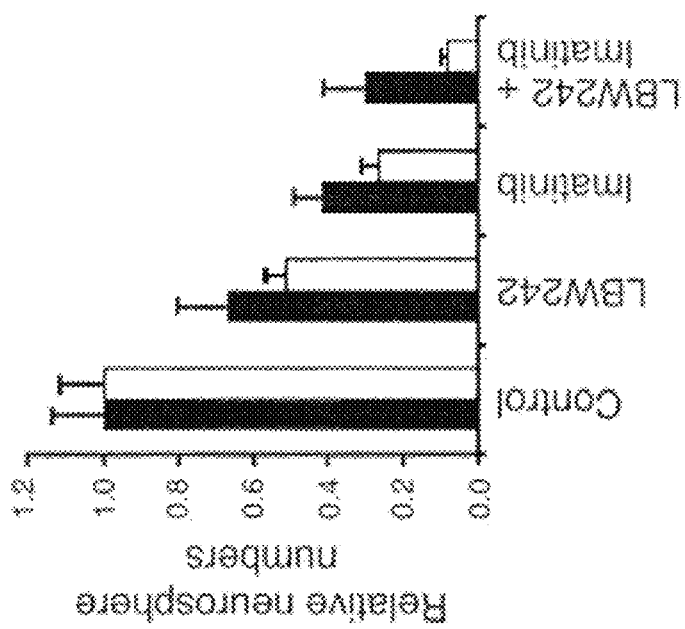
FIG. 6C: depicts a graph showing the effects of LBW242 and/or imatinib in primary patient-derived glioma neurosphere cultures.

Example 7: Combination Treatment of Primary Human Glioma Neurospheres Supports Synergistic Activity of LBW242 and Imatinib The treatment combination was assayed in primary human glioma tumor neurospheres. In neurospheres derived from 2 different patients with GBM, LBW242 and imatinib had stand-alone activity, and in combination they had additive effects in decreasing overall neurosphere numbers (FIG. 6C). To further confirm this finding, the combinatorial index of imatinib plus LBW242 was calculated in a total of 5 neurosphere cultures and 2 adherent cell lines. The effect was additive or synergistic in all but one of the cell cultures tested (Table 2).

TABLE 2

Combinatorial index for treatment with LBW242 plus imatinib in glioma cells

| Cells | Expected survival proportion | Observed survival proportion | Combinatorial index |
| --- | --- | --- | --- |
| Primary hBT69 | 0.065 | 0.07 | 1.07 (additive) |
| Primary hBT74 | 0.306 | 0.147 | 0.48 (synergy) |
| Primary hBT78 | 0.18 | 0.29 | 1.61 (antagonism) |
| Primary hBT79 | 0.16 | 0.08 | 0.59 (synergy) |
| Primary hBT85 | 0.29 | 0.121 | 0.41 (synergy) |
| LN827 | 0.88 | 0.06 | 0.07 (synergy) |
| U87 | 1.08 | 0.63 | 0.58 (synergy) |

The combinatorial indices for LBW242 and imatinib were expressed as the ratio of observed/expected cells surviving, where the expected result was calculated as the proportion of surviving cells following treatment with LBW242 alone multiplied by the proportion of cells following treatment with imatinib alone.

The morphological appearance of some neurospheres treated with LBW242 in combination with imatinib suggested aggregates of dead cells (FIG. 6D). To specifically assess induction of apoptosis within these neurospheres, lysates from treated neurospheres were analyzed with an antibody specific for the activated form of caspase-3. Consistent with the data derived from glioma cell lines, there was no appreciable caspase-3 activation by imatinib or LBW242 alone, and minimal activation by AMN107 alone (FIG. 6E). However, marked activation of caspase-3 was apparent when either imatinib or AMN107 was combined with LBW242 (FIG. 6E). To determine whether the same synergistic effect on primary glioma neurospheres could be recapitulated in the in vivo setting, we orthotopically implanted stem cell-enriched neurosphere cultures of primary human glioma cells intracranially in nude mice. After establishing tumors for 12 days, animals were divided into cohorts that were treated with vehicle, AMN107, LBW242, or a combination of AMN107 and LBW242, as described above. All animals treated with either vehicle or single agents died within 60 days. However, 3 of 7 mice treated in the combination arm remained alive and well at 125 days follow-up, with no evidence of either disease or treatment toxicity (FIG. 6F). The survival benefit at 60 days or more was highly statistically significant (P=0.01, 2-tailed Fisher's exact test). Taken together, these results support the synergistic activity of PDGFR and IAP inhibition in both in vitro and in vivo models derived from glioma cell lines and primary human glioblastoma samples.

Figure 9:
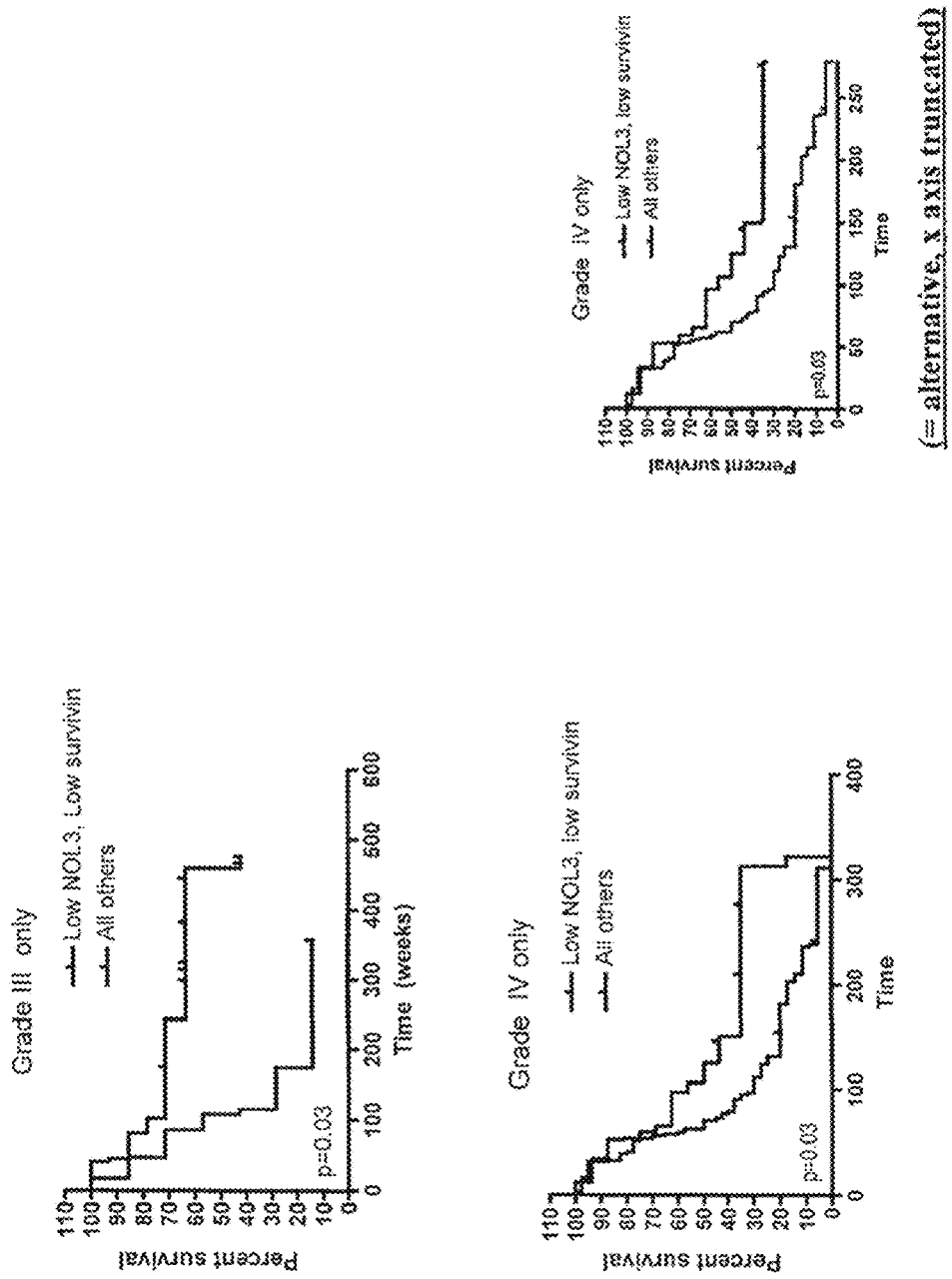
FIG. 9: depicts graphs showing that the combination of NOL3 and survivin levels results in a significant difference in survival in both Grade III and IV gliomas.

Example 8: NOL3 Expression Level Combined with IAP Expression Level in Patient Samples Predicts Clinical Outcome Based on the finding that modulation of NOL3 expression and IAP activity induces a potent anti-tumor effect, it was next investigated whether the combination of IAP expression and NOL3 expression levels has an important impact on clinical outcomes. The effect on patient survival of NOL3 expression in combination with expression levels of the IAP survivin was assessed in an mRNA expression dataset (Phiilips et al, 2006) (FIG. 7). This analysis indicated that high-grade glioma patients whose tumors had low levels of both NOL3 and survivin had significantly longer survival than those with either high levels of NOL3 alone, high levels of survivin alone, or high levels of both. The estimated 3 year survival was 63% (95% CI 41-85%) for patients with low levels of NOL3 and survivin, versus 24% (95% CI 13-35%) for all others, with a median survival of 322 versus 72 weeks. As higher expression of NOL3 occurs in tumors of higher grade it was possible that the tumor grade accounted for the difference in survival. To examine this possibility, the same comparison was performed following stratification of patients by histological grade. Neither NOL3 (FIG. 8A) nor survivin (FIG. 8B) levels resulted in a significant difference in survival when assessed individually in stratified patient groups. However, the combination of both low NOL3 and low survivin levels led to significantly improved survival for both patients with either grade III tumors (median survival 460 versus 108 weeks, p=0.035) or for patients with grade IV tumors (median survival 115 versus 66 weeks, p=0.028) (FIG. 9). Thus the combination of NOL3 and survivin expression appears to confer a prognostic effect more significant than that resulting from histological grade alone.

Example 9: Synthesis of the IAP Inhibitors of the Invention

Described below is a synthesis procedure for LBW 242 (N-[1-cyclohexyl-2-oxo-2-(6-phenethyl-octahydro-pyrrolo[2,3-c]pyridin-1-yl)-ethyl]-2-methylamino-propionamide).

Analogous synthesis procedures can be used to prepare the other IAP inhibitors of the invention.

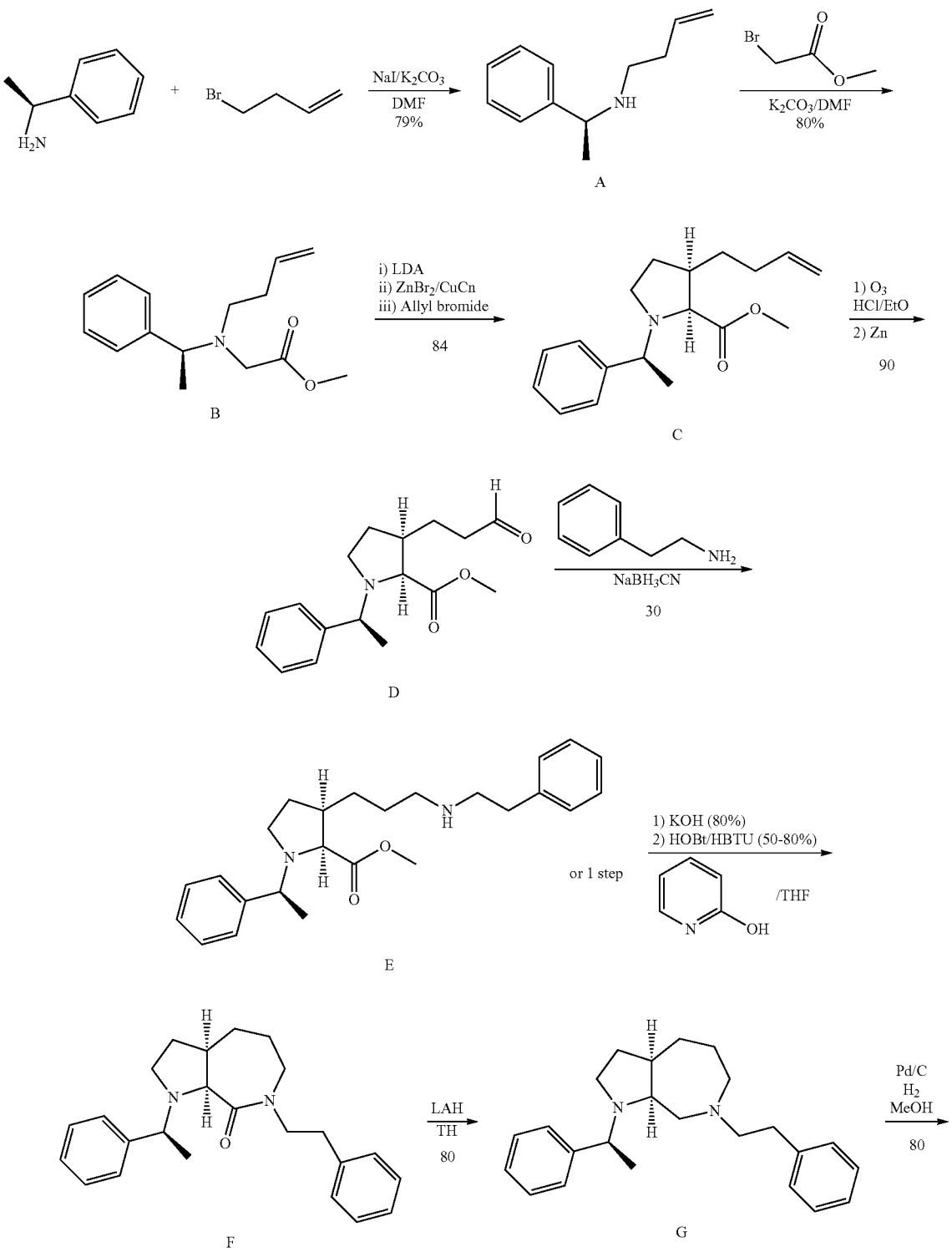

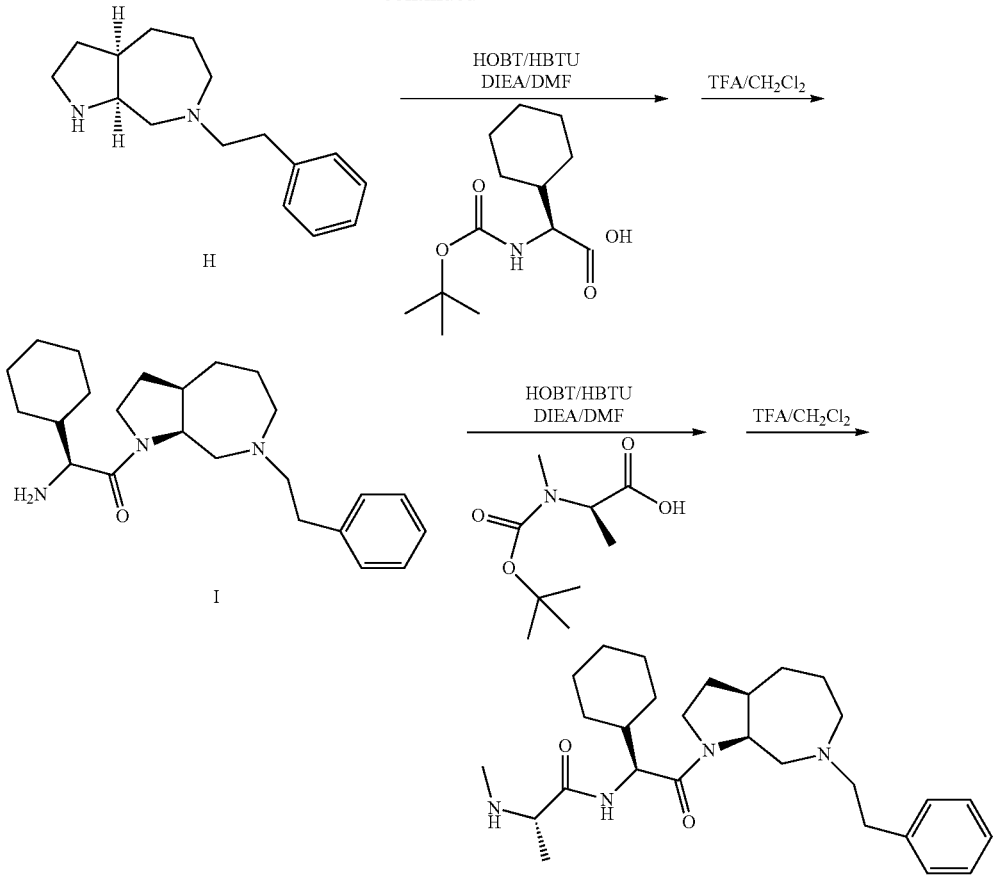

But-3-enyl-((S)-1-phenyl-ethyl)-amine (A)

To a solution of S—(−)-1-phenyl ethylamine (15.75 g, 130 mmol) in 150 mL of DMF at 0° C. is added K$_2$CO$_3$ (53.9 g, 390 mmol) in small portions. After stirring at 0° C. for 10 min, 4-bromobutene (13.5 g, 100 mmol) is added dropwise and followed by NaI (58.5 g, 390 mmol) in small portions. The reaction mixture, a white suspension, is heated to 95° C. and stirred overnight/16 hrs. The solution is cooled to RT and diluted with 200 mL of ether, and washed with 3×100 ml of water. The organic layer is dried over Na$_2$SO$_4$ and concentrated. The crude product is purified by distillation (65~70° C. under high vacuum) to yield a colorless liquid (13.5 g, 76.7%).

[But-3-enyl-((S)-1-phenyl-ethyl)-amino]-acetic acid ethyl ester (B)

To a solution of But-3-enyl-((S)-1-phenyl-ethyl)-amine (6.37 g, 36.4 mmol) in 150 mL of DMF at 0° C. is added K$_2$CO$_3$ (10.0 g, 72.8 mmol) in small portions. After stirring at 0° C. for 10 min, ethylbromoacetate (8.35 g, 54.6 mmol) is added slowly. The reaction mixture, a white suspension, is stirred at r.t. overnight/16 hrs. The solution is diluted with 200 mL of ether, and washed with 3×100 ml of water. The crude product is purified by chromatography (hexane/CH2Cl2: 50/50) to give a pale liquid (8.5 g, 94.5%).

(2S,3R)-3-But-3-enyl-1-((S)-1-pheny l-ethyl)-pyrrolidine-2-carboxylic acid ethyl ester (C)

To a solution of diisopropylamine (3.6 g, 35.7 mmol) in THF (80 mL) at −40° C. is added BuLi (14.28 mL, 35.7 mmol, 2.5 M in hexane) slowly. The solution is warmed to 0° C. and stirred for 30 min to form an LDA solution. The LDA solution is cooled to −70° C. and added to a solution of [But-3-enyl-((S)-1-phenyl-ethyl)-amino]-acetic acid ethyl ester (7.8 g, 29.8 mmol) in THF (80 mL) slowly at −70° C. The light yellowish reaction solution is stirred at −20° C. for 30 min to become a deep yellow solution, and then cooled to −70° C. To the solution is added ZnBr$_2$ (16.76 g, 74.5 mmol) in ether (50 mL) dropwise at −70° C. After stirring at RT for 1.5 hrs, the reaction solution is cooled to 0° C. and added a solution of CuCN (3.47 g, 38.74 mmol) and LiCl (3.29 g, 77.48 mmol) in THF (80 ml) slowly. After stirring at 0° C. for 10 min, allyl bromide (7.26 g, 60 mmol) is added dropwise to the reaction solution, and warmed very slowly to r.t. After stirring overnight at r.t., the reaction is quenched by addition of 60 mL of saturated NH$_4$Cl and extracted with 3×150 mL of ether. The combined organic layers are concentrated. The crude product is purified by chromatography (hexane/EtOAc: 85/15) to give a colorless liquid (7.4 g, 82.6%). (ZnBr$_2$ is dried at 150° C. under high vacuum for 1 hour before use.)

(2S,3R)-1-((2E,4Z)—(S)-1)2-Dimethyl-hexa-2,4-dienyl)-3-(3-oxo-propyl) pyrrolidine-2-carboxylic acid ethyl ester (D)

(2S,3R)-3-But-3-enyl-1-((S)-1-phenyl-ethyl)-pyrrolidine-2-carboxylic acid ethyl ester (1.0 g, 3.32 mmol) is dissolved in EtOH (10 mL) with HCl (0.5 mL, 37%), and cooled to −70° C. Ozone gas is bubbled though the solution for about 10 min or until the solution is turned very light blue color. The nitrogen gas is bubbled though the solution for 15 min to remove excess ozone in the solution. To the cool solution is added Zn dust (0.43 g. 6.6 mmol) and HCl (0.5 mL, 37%), and stirred at r.t. for 20 min. After filtration the solution is diluted with 50 mL of CH2Cl2 and washed with saturated NaHCO$_3$ (10 mL) and 2×20 ml of water. After dried and concentrated, a colorless liquid (1.0 g) is obtained without further purification for next step reaction.

(2S,3R)-3-(3-Phenethylamino-propyl)-1-((S)-1-phenyl-ethyl)-pyrrolidine-2-carboxylic acid ethyl ester (E)

To a solution of (2S,3R)-1-((2E,4Z)—(S)-1,2-Dimethyl-hexa-2,4-dienyl)-3-(3-oxo-propyl) pyrrolidine-2-carboxylic acid ethyl ester (1. g, crude) in EtOH (IO mL) is added phenethylamine (0.44 g, 3.65 mmol) at r.t. After stirring at r.t. for 30 min, NaBH$_3$CN (0.3 g, 4.87 mmol) is added in one portion. After stirring at r.t. for 1.5 Hrs, the reaction solution is diluted with 50 mL of ether and washed with 20 mL of brine. The ether layer is concentrated and the crude product is purified by chromatography (CH$_2$Cl$_2$/MeOH: 97/3) to give a pale liquid (405 mg, 30.0%).

(3aS57aS)-6-Phenethyl-1-((S)-1-phenyl-ethyl)-octahydro-pyrrolo[2,3-c]pyridin-7-one (F)

(2S,3R)-3-(3-Phenethylamino-propyl)-1-((S)-1-phenylethyl)-pyrrolidine-2-carboxylic acid ethyl ester (340 mg, 0.83 mmol) is dissolved in 20 mL of MeOH/KOH/H$_2$O (10 mL/5 g/5 mL). After stirring at 80° C. for 2 hrs, the solution is cooled to 0° C. and neutralized by addition of HCl (37%) to pH=5. After concentration the crude product is dissolved in 1 mL of CH$_2$Cl$_2$, and filtered through a short silica gel plug and eluted with CH2Cl2/MeOH (93/7) to give a pale glassy solid (250 mg, 78.9%) as the acid.

To a solution (0.05-0.1 M) of acid (1 equivalent) in DMF at r.t. is added diisopropylethylamine (5 equivalents). After stirring at r.t. for 20 min, a solution (0.05-0.1 M) of HOBT (1.2 equivalents) and HBTU (1.2 equivalents) in DMF is added to the reaction mixture, and continued to be stirred for 1.5 h (or monitored by TLC). The reaction solution is diluted with ether (1×5~10 times by volume of the solution), and washed with water (twice X3 by volume of the solution). The combined organic solution is concentrated. The crude product is diluted with CH2Cl2 and dried over Na2SO4, and purified by chromatography (CH2Cl2/MeOH:97/3) to give pure product (70-95% yield).

Procedure for Compound F Using 2-Hydroxyl Pyridine:

A solution of (2S,3R)-3-(2-Phenethylamino-ethyl)-1-((S)-1-phenyl-ethyl)-pyrrolidine-2 carboxylic acid methyl ester (400 mg, 1.05 mmol) and 2-hydroxyl pyridine (100 mg, 1.05 mmol) in THF (10 mL) is stirred at 40° C. for 24 hrs. The reaction is diluted with 50 mL of ether and washed with 2×120 mL of water. After dried and concentrated to give a pale liquid (350 mg) without further purification for next step reaction.

(3aR,8aS)-7-Phenethyl-1-((S)-1-phenyl-ethyl)-decahydro-pyrrolo[2,3-c]a zepine (G)

To a solution (0.02M) of lactam (1 equivalent) in THF at −20° C. is added a solution (0.02M) of LiAlH$_4$ (2 equivalent) in THF slowly. After stirring at r.t. for 1.5 hrs, the solution is diluted with ether (1×5 times by volume of the solution) and washed with water (twice 2 times by volume of the solution), dried and concentrated. The crude product is purified by chromatography (CH$_2$Cl$_2$/MeOH:97/3) to give product (yield 70-90%).

(3aR,8aS)-7-Phenethyl-decahydro-pyrrolo[2,3-c] azepine (H)

A solution/suspension of reactant (<1 g) and Pd 10% on carbon (20% by weight) in MeOH (10 mL, with 2 drops of acetic acid) in a 1000 ml round flask is vigorously stirred at r.t. under hydrogen gas (at atmosphere pressure) from a balloon for 4-8 hrs. After degassed by house vacuum for 10 min, the reaction mixture is filtered to remove catalyst and concentrated. The crude product is diluted with CH$_2$Cl$_2$/ H$_2$O (8/2, reasonable amount) and neutralized with 10% NH4OH to pH=7-8. After dried and concentrated to give product (80%—quantitative yield) without purification for the next step reaction.

LBW 242:

Prepared from compound H using the scheme described below:

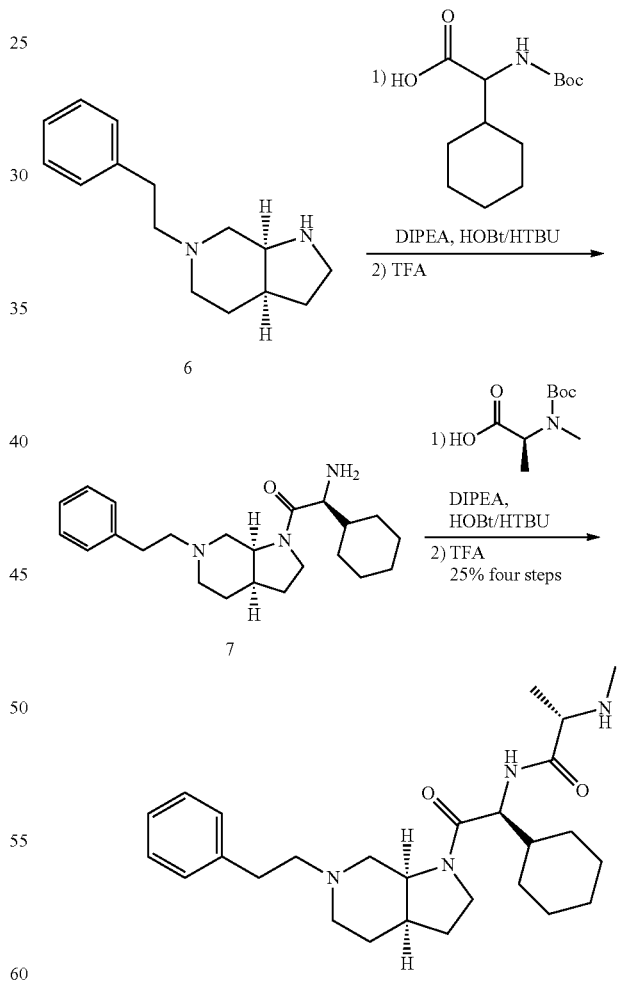

Compound (7):

To a solution of 6 in dichloromethane (25 mL) is added sequentially diisopropylethylamine (4.17 mL, 24 mmol), t-Boc-L-cyclohexylglycine (1.54 g, 6 mmol), and a solution of 0.45 M HOBt/HBTU in DMF (16 mL, 7.19 mmol). The mixture is stirred overnight at room temperature, then diluted with EtOAc (200 mL) and washed sequentially with 1 M aq. citric acid (50 mL), water (50 mL), aq. Sat. NaHCO$_3$ (50 mL) and brine (2×50 mL). The organic layer is dried and concentrated under vacuum. The residue is purified by flash chromatography (silica gel; Hexane/EtOAc 1:9) to provide a yellow oil. The yellow oil is dissolved in dichloromethane (20 mL), TFA (10 mL) is added and the mixture is stirred at room temperature for 3 h. The mixture is concentrated and the residue is dissolved in dichloromethane (100 mL) and neutralized with saturated sodium bicarbonate. The solution is extracted with dichloromethane (3×50 mL). The organic extracts are combined, dried and concentrated under vacuum to provide 1.75 g (79% two steps) of the title compound which is used in next step without further purification or characterization.

LBW 242:

To a solution of 7 (1.75 g, 4.74 mmol) in dichloromethane (25 mL) is added sequentially diisopropylethylamine (3.30 mL, 19 mmol), t-Boc-N-methyl-L-alanine (0.97 g, 4.74 mmol), and a solution of 0.45 M HOBt/HBTU in DMF (13 mL, 5.691 mmol). The mixture is stirred overnight at room temperature. The mixture is diluted with EtOAc (200 mL) and washed sequentially with 1 M citric acid (50 mL), water (50 mL), aq. Sat. NaHCO3 (50 mL) and brine (2×50 mL). The organic layer is dried and concentrated under vacuum. The residue is dissolved in dichloromethane (20 mL), TFA (10 ml) is added and the mixture is stirred at room temperature for 3 hours. The mixture is concentrated and the residue is dissolved in dichloromethane (100 mL) and neutralized with saturated sodium bicarbonate. The solution is extracted with dichloromethane (3×50 mL). The organic extracts are combined, dried and concentrated under vacuum. The residue is purified by HPLC (C-18 silica gel, 20% CH3CN/H2O in 0.5% TFA) to provide 1 g (36% two steps) of the title compound as TFA salt.

EQUIVALENTS

The invention has been described herein with reference to certain examples and embodiments only. No effort has been made to exhaustively describe all possible examples and embodiments of the invention. Indeed, those of skill in the art will appreciate that various additions, deletions, modifications and other changes may be made to the above-described examples and embodiments, without departing from the intended spirit and scope of the invention as recited in the following claims. It is intended that all such additions, deletions, modifications and other changes be included within the scope of the following claims.

What is claimed:

1. A method of treating a glioma in a subject, the method comprising:
    administering a therapeutically effective amount of a receptor tyrosine kinase inhibitor and a therapeutically effective amount of an IAP inhibitor to the subject having the glioma when a level of NOL3 expression in the subject's glioma is higher than a reference level of NOL3 expression in a reference sample, wherein the IAP inhibitor is a compound of formula (II)

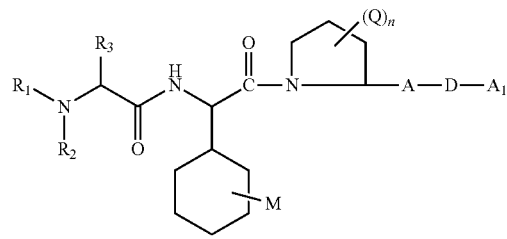

or pharmaceutically acceptable salts thereof, wherein
$R_1$ is H or $C_1$-$C_4$ alkyl;
$R_2$ is H or $C_1$-$C_4$-alkyl;
$R_3$ is H or $C_1$-$C_4$ alkyl;
A is 5- or 6-membered heteroaryl containing 1-4 ring heteroatoms selected from the group consisting of nitrogen, oxygen, and sulfur, the heteroaryl being unsubstituted or substituted with lower alkyl, amino, or halo;
D is O, C(O), or NCH$_3$;
$A_1$ is phenyl or 5- or 6-membered heteroaryl containing 1-4 ring heteroatoms selected from the group consisting of nitrogen, oxygen, and sulfur, the phenyl and the heteroaryl being unsubstituted or substituted with halogen;
M is H; and
n is 0.

2. The method of claim 1 further comprising measuring the level of NOL3 expression in the subject's glioma.

3. The method of claim 2, wherein measuring the level of NOL3 expression comprises measuring NOL3 mRNA expression or measuring NOL3 polypeptide expression.

4. The method of claim 1, wherein the glioma is an astrocytoma, an ependymoma, an oligodendroglioma, a mixed glioma, or glioblastoma multiforme.

5. The method of claim 1, wherein the IAP inhibitor is (S)—N—((S)-1-Cyclohexyl-2-{(S)-2-[4-(4-fluoro-benzoyl)-thiazol-2-yl]-pyrrolidin-1-yl}-2-oxo-ethyl)-2-methyl-aminopropionamide, or a pharmaceutically acceptable salt thereof.

6. The method of claim 5, wherein the receptor tyrosine kinase inhibitor is selected from imatinib, AMN107, AEW541, and PKI166.

7. A method of increasing apoptosis of a glioma in a subject, the method comprising: administering a therapeutically effective amount of a receptor tyrosine kinase inhibitor and a therapeutically effective amount of an IAP inhibitor to the subject having the glioma when a level of NOL3 expression in the subject's glioma is higher than a reference level of NOL3 expression in a reference sample, wherein the IAP inhibitor is a compound of formula (II)

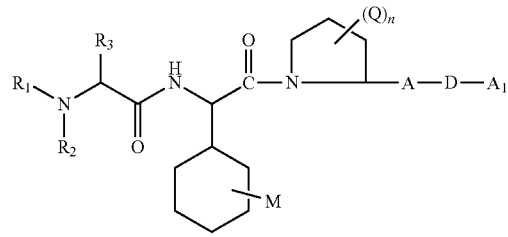

or pharmaceutically acceptable salts thereof, wherein
$R_1$ is H or $C_1$–$C_4$ alkyl;
$R_2$ is H or $C_1$–$C_4$-alkyl;
$R_3$ is H or $C_1$–$C_4$alkyl; 0
A is 5- or 6-membered heteroaryl containing 1-4 ring heteroatoms selected from the group consisting of nitrogen, oxygen, and sulfur, the heteroaryl being unsubstituted or substituted with lower alkyl, amino, or halo;
D is O, C(O), or $NCH_3$;
$A_1$ is phenyl or 5- or 6-membered heteroaryl containing 1-4 ring heteroatoms selected from the group consisting of nitrogen, oxygen, and sulfur, the phenyl and the heteroaryl being unsubstituted or substituted with halogen;
M is H; and
n is 0.

8. The method of claim 7 further comprising measuring the level of NOL3 expression in the subject's glioma.

9. The method of claim 8, wherein measuring the level of NOL3 expression comprises measuring NOL3 mRNA expression or measuring NOL3 polypeptide expression.

10. The method of claim 7, wherein the glioma is an astrocytoma, an ependymoma, an oligodendroglioma, a mixed glioma, or glioblastoma multiforme.

11. The method of claim 7, wherein the IAP inhibitor is (S)—N—((S)-1-Cyclohexyl-2-{(S)-2-[4-(4-fluoro-benzoyl)-thiazol-2-yl]-pyrrolidin-1-yl}-2-oxo-ethyl)-2-methyl-aminopropionamide, or a pharmaceutically acceptable salt thereof.

12. The method of claim 11, wherein the receptor tyrosine kinase inhibitor is selected from imatinib, AMN107, AEW541, and PKI166.

13. A method of increasing apoptosis of a glioma in a subject, the method comprising: administering a therapeutically effective amount of NOL3 siRNA and a therapeutically effective amount of an IAP inhibitor to the subject having the glioma when a level of NOL3 expression in the subject's glioma is higher than a reference level of NOL3 expression in a reference sample, wherein the IAP inhibitor is a compound of formula (II)

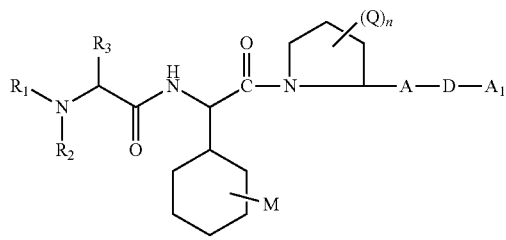

or pharmaceutically acceptable salts thereof, wherein
$R_1$ is H or $C_1$–$C_4$ alkyl;
$R_2$ is H or $C_1$–$C_4$-alkyl;
$R_3$ is H or $C_1$–$C_4$alkyl;
A is 5- or 6-membered heteroaryl containing 1-4 ring heteroatoms selected from the group consisting of nitrogen, oxygen, and sulfur, the heteroaryl being unsubstituted or substituted with lower alkyl, amino, or halo;
D is O, C(O), or $NCH_3$;
$A_1$ is phenyl or 5- or 6-membered heteroaryl containing 1-4 ring heteroatoms selected from the group consisting of nitrogen, oxygen, and sulfur, the phenyl and the heteroaryl being unsubstituted or substituted with halogen;
M is H; and
N is 0.

14. The method of claim 13 further comprising measuring the level of NOL3 expression in the subject's glioma.

15. The method of claim 14, wherein measuring the level of NOL3 expression comprises measuring NOL3 mRNA expression or measuring NOL3 polypeptide expression.

16. The method of claim 13, wherein the glioma is an astrocytoma, an ependymoma, an oligodendroglioma, a mixed glioma, or glioblastoma multiforme.

17. The method of claim 13, wherein the IAP inhibitor is (S)—N—((S)-1-Cyclohexyl-2-{(S)-2-[4-(4-fluoro-benzoyl)-thiazol-2-yl]-pyrrolidin-1-yl}-2-oxo-ethyl)-2-methyl-aminopropionamide, or a pharmaceutically acceptable salt thereof.

* * * * *